(12) United States Patent
Nuccio et al.

(10) Patent No.: US 6,979,732 B1
(45) Date of Patent: Dec. 27, 2005

(54) POLYNUCLEOTIDE COMPOSITIONS ENCODING S-ADENOSYL-L-METHIONINE:PHOSPHOETHANOLAMINE N-METHYLTRANSFERASE AND METHODS FOR MODULATING LIPID BIOSYNTHESIS IN PLANTS

(75) Inventors: Michael L. Nuccio, Melrose, FL (US); Andrew D. Hanson, Gainesville, FL (US); Susan A. Henry, Pittsburgh, PA (US)

(73) Assignees: University of Florida, Gainesville, FL (US); Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/525,885

(22) Filed: Mar. 15, 2000

(51) Int. Cl.[7] ............................ C07H 21/04; C12N 1/20
(52) U.S. Cl. ................. 536/23.2; 435/252.3; 435/235.1
(58) Field of Search ............................. 536/23.2, 23.6; 435/69.1, 71.1, 471, 235.1, 419, 252.3

(56) References Cited

PUBLICATIONS

Van de Loo et al, "An oleate 12–hydroxylase from Ricinus communis L. is a fatty acyl desaturase homolog", Jul. 1995, Proc. Natl. Acad. vol. 92, pp. 6743–6747.*
Broun et al., "Catalytic Plasticity of Fatty Acid .Modification Enzymes Underlying Chemical Diversity of Plant Lipids", Nov. 1998, Science vol. 282, pp. 1315–1317.*
Doerks et al, "Protein annotation: detective work for function prediction", Jun. 1998, TIG, vol. 14 No. 6, pp. 248–250.*
Smith et al, The challenges of genome sequence annotation or "The devil is in the detail", Nov. 1997, Nature Biotechnology vol. 15, pp. 1222–1223.*
Brenner, "Errors in genome annotation", Apr. 1999, TIG, vol. 15, No. 4, pp. 132–133.*
Bork, Go hunting in sequence databases but watch out for the traps, Oct. 1996, vol. 12, No. 10, pp. 425–427.*
Smith et al., "Phosphocholine synthesis in spinach: Characterization of phosphoethanolamine N–methyltransferase," *Physiolgia Plantarum*, 108:286–94, Mar. 2000.
Database, Swall Online, Accession No. Q41587, Nov. 1996.
Database, Swall Online, Accession No. Q23552, Nov. 1996.
Database, EM_EST Online, AC/ID AI731819, Jun. 1999.
Database, EM_PLN Online, AC AJ234432, Oct. 1998.
Weretilnyk et al., "Enzymes of Choline Synthesis in Spinach," *Plant Physiol.*, 109:1085–91, 1995.
Nuccio et al., "The endogenous choline supply limits glycine betaine synthesis in transgenic tobacco expressing choline monooxygenase," *The Plant Journal*, 16:487–96, 1998.
Nuccio, et al., "cDNA cloning of phosphoethanolamine N–methyltransferase from spinach by complementation in *Schizosaccharomyces pombe* characterization of the recombinant enzyme." *J. Biol. Chem.*, 275(19):14095–14101, 2000.

14717 Lambda–PRL2 *Arabidopsis thaliana* cDNA clone 175H22T7, mRNA sequence, Genbank Database Accession No. H36195, Dec. 30, 1997.
ATTS5901 Ors–B *Arabidopsis thaliana* cDNA 5', mRNA sequence, Genbank Datatbase Accession No. F19862, Feb. 23, 1996.
EST281481 tomato callus, TAMU *Lycopersicon esculentum* cDNA clone cLEC34P17, mRNA sequence, Genbank Datatbase Accession No. AW035649, Sep. 15, 1999.
Hanson et al., "Metabolic engineering of choline and glycine betaine synthesis," *Zia Symposium III, Engineering and Quantifying Metabolism in Plants*, New Mexico State University, Las Cruces, New Mexico, Jan. 7–8, 2000.
Kanipes, "analysis of the phospholipid methyltransferases in the fission yeast, *Schizosaccharomyces pombe*," Ph.D. Thesis, Carnegie Mellon University, Mellon College of Science, Pittsburg, PA, 1997.
Nuccio et al., "The endogenous choline supply limits glycine betaine synthesis in transgenic tobacco expressing choline monooxygenase," *The Plant Journal*, 16(4):487–496, 1998.
Nuccio, "Choline monooxygenase and phosphoethanolamine N–methyltransferase: Installing the glycine betaine synthesis pathway in tobacco," *Zia Symposium III, Engineering and Quantifying Metabolism in Plants*, New Mexico State University, Las Cruces, New Mexico, Jan. 7–8, 2000.
Rhodes and Hanson, "Quaternary ammonium and tertiary sulfonium compounds in higher plants," *Annu. Rev. Plant Physiol Plant Mol. Biol.*, 44:357–384, 1993.
Smith, "Purification and characterization of S–adenosyl–L–Methionine: Phosphoethanolamine N–Methyltransferase from spinach," M.S. Thesis, McMaster University, Hamilton, Ontario, 1995.
*Spinacia oleracea* phosphoethanolamine N–methyltransferase (PEAMT) mRNA, complete cds., Genbank Database Accession No. AF237633, Apr. 3, 2000.
Nuccio, et al., "cDNA cloning of phosphoethanolamine N–methyltransferase from spinach by complementation in *Schizosaccharomyces pombe* and characterization of the recombinant enzyme." *J. Biol. Chem.*, 275(19):14095–14101, 2000.

* cited by examiner

*Primary Examiner*—Elizabeth F. McElwain
(74) *Attorney, Agent, or Firm*—Williams, Morgan & Amerson, P.C.

(57) ABSTRACT

Disclosed are compositions and methods for increasing the nutritional value of plants and plant parts. In illustrative embodiments PEAMT and ΔPEAMT polynucleotide and polypeptide compositions are disclosed as well as their use in modulating the levels of lipid compounds, and particularly, regulating the level of phosphatidylcholine, and its precursors in plants and seeds derived therefrom. Also disclosed are methods for modulating the level of glycine betaine and choline-O-sulfate in cells, and increasing the tolerance of transformed plants to osmotic and cryogenic stress.

16 Claims, 10 Drawing Sheets

FIG. 3

SEQUENCE LISTING

```
<160> NUMBER OF SEQ ID NOS: 8

<210> SEQ ID NO 1
<211> LENGTH: 2235
<212> TYPE: DNA
<213> ORGANISM: Spinacia oleracea

<400> SEQUENCE: 1
cattcatttg aagcgtggaa gtagtagttt tgtggtagag tgaatttgat actcctactg      60
ctcatgcggc agagaggcag ggcttcgaac cgtagatcca ggacttttc tcgttctcgc     120 attgccattg agggtcacta atacttttaa ctatctcctt cttttttcttt cccacaattt    180
```

```
ctgcgttttc acgcacatta atctcaccta ttttctagct tcttcatttt ctcaatcaat    240
ctctcgtgtt attatggccg cttcagctat gggagtgttg caagagagag aggtgttcaa    300
gaaatactgg attgaacact ctgttgattt gactgttgag gctatgatgc ttgattcaca    360
agcttcagat cttgacaaag tggagcgacc tgaggtactt tccatgcttc caccttatga    420
aggaaagtct gtcttagaac tcggtgctgg tattggtcgt tttactggtg aattggccga    480
gaaagctagc caggtcatcg ctctggattt cattgagagt gttataaaga agaatgaaag    540
cataaatggg cattacaaaa atgtgaagtt tatgtgtgct gatgtgacat ctccaagtct    600
caacatttca ccaaattccg tggatatcat attctccaat tggctactca tgtatctttc    660
tgatgaagag gttgagcgtc tggttgaaag gatgttgaaa tggttgaagc caggaggata    720
cattttcttc agagaatctt gttttcatca atcaggagat cacaagcgca aaagcaatcc    780
aacccactac cgtgaaccta ggttctacac caagatcttc aaagaatgcc atatgcaaga    840
tgattctggg aactcctatg agctctccct aattggctgc aaatgtattg gagcttatgt    900
caaaagcaag aagaatcaga accagataag ctggttatgg cagaaagttg attcagagga    960
tgacaagggg ttccagcgat tcttggattc tagtcaatac aagtttaaca gcatactgcg   1020
ttatgagcgt gtatttggtc ctggttatgt tagtaccgga ggactcgaaa caaccaagga   1080
gtttgtatca aagcttgact tgaagcctgg ccagaaggtc ctagatgtgg ttgtggcat   1140
aggtggaggt gattttttaca tggcagagaa ctatgatgtt gaggttgttg gaattgatct   1200
ctccattaat atgatttctt tgccccttga gcgctcaatt ggcctcaaat gtgctgttga   1260
gtttgaggtg gcagattgca ccaagaaaga ttaccctgaa aactcttttg atgtcatcta   1320
cagccgtgat accattctgc atattcagga caaacctgct ttatttagat ccttccacaa   1380
atggttgaaa cctggaggca agttcttat tagtgactac tgtaagagtg ctggtacacc   1440
ttcagctgaa tttgctgcat acatcaggca gaggggatat gatctccacg atgtgaaggc   1500
atatggcaag atgcttaaag atgctggatt cgttgaggtt attgctgaga ataggactga   1560
ccagttcatt caagttctgc agaaggaact agatgctctt gaacaggaga aggatgactt   1620
cattgatgat ttctctgagg aggattataa cgacatagtt gatggttgga aggccaagtt   1680
ggtgaggact acagagggtg agcaacaatg gggtttgttc attgccaaga aaatgtgaag   1740
aatgagctgg tgaaagcagc acggtgcctt tttctagtat tagtttatca atgtatttc    1800
agttcatgga ctgtatatgc aaaatctacc aataagctgt gagttgcaaa ctgaaagatg   1860
atttcttata gtcacttctg aattagcaca agcagtgaag ttcgcataag aaactgaagg   1920
gaactcatgg agttgcagac gaaatcatca aaacggcaga acccactctc tatatagaga   1980
tctagtggtt aagttatgtg ttttgtacat tttccgttcc aagttcactc aatcttacca   2040
tcataatatc accgcttta cttctttata tggtggattg aagtcgaaac tctttgttag   2100
taatgtgtat tagtttgttg aaagtggaac ttgcaacaca cttattcaca agtgtgtagg   2160
gaaatatgga ttttgtatta gtatgtactg cacttagttg ttaaaaggat acttcctacg   2220
ttttcttctg ttgca                                                   2235
```

<210> SEQ ID NO 2
<211> LENGTH: 494
<212> TYPE: PRT
<213> ORGANISM: Spinacia oleracea

<400> SEQUENCE: 2

```
Met Ala Ala Ser Ala Met Gly Val Leu Gln Glu Arg Glu Val Phe Lys
 1               5                  10                  15

Lys Tyr Trp Ile Glu His Ser Val Asp Leu Thr Val Glu Ala Met Met
                 20                  25                  30

Leu Asp Ser Gln Ala Ser Asp Leu Asp Lys Val Glu Arg Pro Glu Val
             35                  40                  45

Leu Ser Met Leu Pro Pro Tyr Glu Gly Lys Ser Val Leu Glu Leu Gly
         50                  55                  60

Ala Gly Ile Gly Arg Phe Thr Gly Glu Leu Ala Glu Lys Ala Ser Gln
 65                  70                  75                  80

Val Ile Ala Leu Asp Phe Ile Glu Ser Val Ile Lys Lys Asn Glu Ser
                 85                  90                  95

Ile Asn Gly His Tyr Lys Asn Val Lys Phe Met Cys Ala Asp Val Thr
                100                 105                 110

Ser Pro Ser Leu Asn Ile Ser Pro Asn Ser Val Asp Ile Ile Phe Ser
             115                 120                 125

Asn Trp Leu Leu Met Tyr Leu Ser Asp Glu Glu Val Glu Arg Leu Val
         130                 135                 140

Glu Arg Met Leu Lys Trp Leu Lys Pro Gly Gly Tyr Ile Phe Phe Arg
145                 150                 155                 160

Glu Ser Cys Phe His Gln Ser Gly Asp His Lys Arg Lys Ser Asn Pro
                165                 170                 175

Thr His Tyr Arg Glu Pro Arg Phe Tyr Thr Lys Ile Phe Lys Glu Cys
                180                 185                 190

His Met Gln Asp Asp Ser Gly Asn Ser Tyr Glu Leu Ser Leu Ile Gly
             195                 200                 205

Cys Lys Cys Ile Gly Ala Tyr Val Lys Ser Lys Asn Gln Asn Gln
210                 215                 220

Ile Ser Trp Leu Trp Gln Lys Val Asp Ser Glu Asp Lys Gly Phe
225                 230                 235                 240

Gln Arg Phe Leu Asp Ser Ser Gln Tyr Lys Phe Asn Ser Ile Leu Arg
             245                 250                 255

Tyr Glu Arg Val Phe Gly Pro Gly Tyr Val Ser Thr Gly Gly Leu Glu
             260                 265                 270

Thr Thr Lys Glu Phe Val Ser Lys Leu Asp Leu Lys Pro Gly Gln Lys
         275                 280                 285

Val Leu Asp Val Gly Cys Gly Ile Gly Gly Asp Phe Tyr Met Ala
         290                 295                 300

Glu Asn Tyr Asp Val Glu Val Val Gly Ile Asp Leu Ser Ile Asn Met
305                 310                 315                 320

Ile Ser Phe Ala Leu Glu Arg Ser Ile Gly Leu Lys Cys Ala Val Glu
             325                 330                 335

Phe Glu Val Ala Asp Cys Thr Lys Lys Asp Tyr Pro Glu Asn Ser Phe
             340                 345                 350

Asp Val Ile Tyr Ser Arg Asp Thr Ile Leu His Ile Gln Asp Lys Pro
             355                 360                 365

Ala Leu Phe Arg Ser Phe His Lys Trp Leu Lys Pro Gly Gly Lys Val
         370                 375                 380

Leu Ile Ser Asp Tyr Cys Lys Ser Ala Gly Thr Pro Ser Ala Glu Phe
385                 390                 395                 400

Ala Ala Tyr Ile Arg Gln Arg Gly Tyr Asp Leu His Asp Val Lys Ala
             405                 410                 415

Tyr Gly Lys Met Leu Lys Asp Ala Gly Phe Val Glu Val Ile Ala Glu
```

```
                420                 425                 430
Asn Arg Thr Asp Gln Phe Ile Gln Val Leu Gln Lys Glu Leu Asp Ala
        435                 440                 445

Leu Glu Gln Glu Lys Asp Asp Phe Ile Asp Asp Phe Ser Glu Glu Asp
    450                 455                 460

Tyr Asn Asp Ile Val Asp Gly Trp Lys Ala Lys Leu Val Arg Thr Thr
465                 470                 475                 480

Glu Gly Glu Gln Gln Trp Gly Leu Phe Ile Ala Lys Lys Met
                485                 490
```

```
<210> SEQ ID NO 3
<211> LENGTH: 1120
<212> TYPE: DNA
<213> ORGANISM: Spinacia oleracea

<400> SEQUENCE: 3
cattcatttg aagcgtggaa gtagtagttt tgtggtagag tgaatttgat actcctactg      60
ctcatgcggc agagaggcag ggcttcgaac cgtagatcca ggactttttc tcgttctcgc     120
attgccattg agggtcacta atacttttaa ctatctcctt cttttctttt cccacaattt     180
ctgcgttttc acgcacatta atctcaccta ttttctagct tcttcatttt ctcaatcaat     240
ctctcgtgtt attatggccg cttcagctat gggagtgttg caagagagag aggtgttcaa     300
gaaatactgg attgaacact ctgttgattt gactgttgag gctatgatgc ttgattcaca     360
agcttcagat cttgacaaag tggagcgacc tgaggtactt ccatgcttc caccttatga      420
aggaaagtct gtcttagaac tcggtgctgg tattggtcgt tttactggtg aattggccga     480
gaaagctagc caggtcatcg ctctggattt cattgagagt gttataaaga agaatgaaag     540
cataaatggg cattacaaaa atgtgaagtt tatgtgtgct gatgtgacat ctccaagtct     600
caacatttca ccaaattccg tggatatcat attctccaat tggctactca tgtatctttc     660
tgatgaagag gttgagcgtc tggttgaaag gatgttgaaa tggttgaagc caggaggata     720
catttcttc agagaatctt gttttcatca atcaggagat cacaagcgca aaagcaatcc     780
aacccactac cgtgaaccta ggttctacac caagatcttc aaagaatgcc atatgcaaga     840
tgattctggg aactcctatg agctctccct aattggctgc aaatgtattg gagcttatgt     900
caaaagcaag aagaatcaga accagataag ctggttatgg cagaaagttg attcagagga    960
tgacaagggg ttccagcgat tcttggattc tagtcaatac aagtttaaca gcatactgcg   1020
ttatgagcgt gtatttggtc ctggttatgt tagtaccgga ggactcgaaa caaccaagga   1080
gtttgtatca aagcttgact gaagcctgg atccccggg                            1120
```

```
<210> SEQ ID NO 4
<211> LENGTH: 289
<212> TYPE: PRT
<213> ORGANISM: Spinacia oleracea

<400> SEQUENCE: 4

Met Ala Ala Ser Ala Met Gly Val Leu Gln Glu Arg Glu Val Phe Lys
  1               5                  10                  15

Lys Tyr Trp Ile Glu His Ser Val Asp Leu Thr Val Glu Ala Met Met
                 20                  25                  30

Leu Asp Ser Gln Ala Ser Asp Leu Asp Lys Val Glu Arg Pro Glu Val
            35                  40                  45

Leu Ser Met Leu Pro Pro Tyr Glu Gly Lys Ser Val Leu Glu Leu Gly
        50                  55                  60
```

-continued

```
Ala Gly Ile Gly Arg Phe Thr Gly Glu Leu Ala Glu Lys Ala Ser Gln
 65                  70                  75                  80

Val Ile Ala Leu Asp Phe Ile Glu Ser Val Ile Lys Lys Asn Glu Ser
                 85                  90                  95

Ile Asn Gly His Tyr Lys Asn Val Lys Phe Met Cys Ala Asp Val Thr
            100                 105                 110

Ser Pro Ser Leu Asn Ile Ser Pro Asn Ser Val Asp Ile Ile Phe Ser
        115                 120                 125

Asn Trp Leu Leu Met Tyr Leu Ser Asp Glu Glu Val Glu Arg Leu Val
130                 135                 140

Glu Arg Met Leu Lys Trp Leu Lys Pro Gly Gly Tyr Ile Phe Phe Arg
145                 150                 155                 160

Glu Ser Cys Phe His Gln Ser Gly Asp His Lys Arg Lys Ser Asn Pro
                165                 170                 175

Thr His Tyr Arg Glu Pro Arg Phe Tyr Thr Lys Ile Phe Lys Glu Cys
            180                 185                 190

His Met Gln Asp Asp Ser Gly Asn Ser Tyr Glu Leu Ser Leu Ile Gly
        195                 200                 205

Cys Lys Cys Ile Gly Ala Tyr Val Lys Ser Lys Asn Gln Asn Gln
210                 215                 220

Ile Ser Trp Leu Trp Gln Lys Val Asp Ser Glu Asp Lys Gly Phe
225                 230                 235                 240

Gln Arg Phe Leu Asp Ser Ser Gln Tyr Lys Phe Asn Ser Ile Leu Arg
                245                 250                 255

Tyr Glu Arg Val Phe Gly Pro Gly Tyr Val Ser Thr Gly Gly Leu Glu
            260                 265                 270

Thr Thr Lys Glu Phe Val Ser Lys Leu Asp Leu Lys Pro Gly Ile Pro
        275                 280                 285

Gly
```

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 5
ctcgagatct g                                                          11

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 6
tcgacagatc tcgag                                                      15

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

```
<400> SEQUENCE: 7 ctcgtgcca                                                                    9

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence:  SYNTHETIC
      OLIGONUCLEOTIDE

<400> SEQUENCE: 8
gatctggcac gag                                                              13
```

POLYNUCLEOTIDE COMPOSITIONS ENCODING S-ADENOSYL-L-METHIONINE:PHOSPHOETHANOLAMINE N-METHYLTRANSFERASE AND METHODS FOR MODULATING LIPID BIOSYNTHESIS IN PLANTS

The United States government has certain rights in the present invention pursuant to Grant number 98-35100-6149 from the United States Department of Agriculture, and Grant number GM19629 from the National Institutes of Health.

1.0 BACKGROUND OF THE INVENTION

1.1 Field of the Invention

The present invention relates to the genetic manipulation of plants, particularly to methods and compositions for altering the lipid content in plants and seed. Also provided are compositions and methods for the preparation of transgenic plants that over-express a PEAMT polypeptide.

1.2 Description of Related Art

Flowering plants are unusual in how they synthesize choline (Cho) moieties. In leaves and other vegetative tissues, the first and committing step is N-methylation of phosphoethanolamine (P-EA) to give phosphomonomethylethanolamine (P-MME), and the subsequent N-methylations occur at the phosphobase level, the phosphatidyl base level, or both, depending on the species (Datko and Mudd, 1988a; 1988b; Rhodes and Hanson, 1993) (FIG. A). For example, in spinach and sugar beet leaves, essentially all flux through the last two methylations is at the phosphobase level (Hanson and Rhodes, 1983; Summers and Weretilnyk, 1993), whereas in soybean cells it is at the Ptd-base level (Datko and Mudd, 1988a). In contrast, Cho synthesis in the bacterium *Rhodobacter sphaeroides*, in fingi, and in mammalian liver proceeds solely via the sequential methylation of phosphatidylethanolamine (Ptd-EA) (Vance et al., 1997; Kanipes and Henry, 1997; Arondel et al., 1993). Nerve tissues have a phosphobase methylation route as well as a phosphatidylbase route, but the first methylation appears not to be restricted to the phosphobase level (Mukherjee et al., 1995; Andriamampanry et al., 1991).

The initial methylation of P-EA in plants is catalyzed by S-adenosyl-L-methionine:phosphoethanolamine N-methyltransferase (PEAMT), which has been detected in all species tested (Datko and Mudd, 1988b; Summers and Weretilnyk, 1993; Nuccio et al., 1998). PEAMT was recently purified 5,400-fold from spinach leaves, giving a preparation containing several polypeptides (Smith et al., 1999). This preparation catalyzed methylation of P-MME and phosphodimethylethanolamine (P-DME) as well as P-EA, and these activities co-purified in a constant ratio through the three last steps in the procedure (Smith et al., 1999). These data suggest that PEAMT could be trifunctional, but do not rule out a duo or trio of similar N-methyltransferases that act on different phosphobases. Pathways involving one, two or three N-methyltransferases all have precedents. In *R. sphaeroides* and liver a single Ptd-EA N-methyltransferase mediates all three methylations (Vance et al., 1997; Arondel et al., 1993) whereas in *Saccharomyces cerevisiae* and *Schizosaccharomyces pombe* there are two enzymes, one mediating the first methylation of Ptd-EA and another mediating primarily the last two (Kanipes and Henry, 1997). The phosphobase pathway in nerve tissues has three separate N-methyltransferases (Mukherjee et al., 1995).

Certain plants (e.g., spinach, sugar beet) use large amounts of Cho to produce the osmoprotectant glycine betaine (GlyBet) via the pathway Cho→betaine aldehyde→GlyBet (Rhodes and Hanson, 1993). Because GlyBet accumulation contributes to resistance to salinity and drought stress, there has been much interest in engineering GlyBet synthesis in plants that do not naturally produce it (Nuccio et al., 1999). However, when enzymes for Cho oxidation to GlyBet are expressed in such plants (e.g., tobacco, canola), they accumulate little GlyBet, apparently in part because their endogenous Cho supply is inadequate (Nuccio et al., 1998; Huang et al., 1999). This has focused attention on the pathway of Cho biosynthesis and its regulation (Nuccio et al., 1999).

Biochemical and physiological evidence shows that the PEAMT-mediated step is a control point in the biosynthesis of Cho moieties, and that at least two mechanisms are involved. One is feedback inhibition: PEAMT activity in crude Lemna extracts (Mudd and Datko, 1989a; 1989b) and purified spinach preparations (Smith et al, 1999) is inhibited by P-Cho, and $^{14}C$ tracer data for sugar beet leaf tissue indicate that this occurs in vivo (Hanson and Rhodes, 1983). Another mechanism may be regulation of PEAMT gene expression. The de novo synthesis of Cho in Lemna, soybean and carrot cells is suppressed by exogenous Cho, and this suppression is accompanied by a decrease in extractable PEAMT activity (Mudd and Datko, 1989a; 1989b). Conversely, salinization in spinach, which increases the consumption of Cho in GlyBet synthesis, causes an increase in PEAMT activity (Weretilnyk et al., 1995). Direct evidence that flux through the PEAMT step limits the synthesis of Cho moieties in viva comes from tobacco engineered to convert Cho to GlyBet; supplying MME or DME increases the flux to Cho and GlyBet but supplying EA does not (Nuccio et al., 1998).

1.3 Deficiencies in the Prior Art

A goal of plant breeding has been to modulate the lipid content in plant seeds, and to alter the levels of various plant oils. Despite the importance of PEAMT as the committing step in the biogenesis of Cho moieties, it has not been cloned or unambiguously characterized with respect to the reaction(s) it catalyzes. Nor has any other plant N-methyltransferase participating in Cho biogenesis been cloned.

2.0 SUMMARY OF THE INVENTION

The present invention overcomes these and other limitations inherent in the prior art by providing compositions and methods for increasing the nutritional value of plants. Methods are also provided particularly for modulating the levels of cellular intermediates, such as phosphoethanolamine, phosphomonomethylethanolamine, phosphodimethylethanolamine, phosphocholine, phosphatidyl choline, choline, glycine betaine, and choline-O-sulfate in plants, plant tissues, and seeds. Methods are also disclosed for altering the lipid content in transformed plants cells expressing one or more of these polynucleotide constructs, in a transgenic plant, and in the seed, tissues, and cells derived from such a transgenic plant.

Disclosed are novel amino acid sequences comprising S-adenosyl-L-methionine:phosphoethanolamine N-methyltransferase (PEAMT) polypeptides, and the polynucleotides that encode these enzymes. Also disclosed are novel amino acid sequences comprising a truncated S-adenosyl-L-methionine:phosphoethanolamine N-methyltransferase (ΔPEAMT) polypeptide, and the polynucleotide that encodes this enzyme. Also disclosed are methods of identifying PEAMT- and ΔPEAMT-specific polypeptide and polynucleotide compositions, methods for preparing recombinant host cells, vectors, virus, and expression constructs, and methods for making transgenic plants that over-express PEAMT- and ΔPEAMT-specific genes. These compositions find particular use in modulating the levels of phosphocholine, phosphatidyl choline, and their precursors in plant cells, tissues, fruits and seeds.

The invention provides an isolated polynucleotide that: (a) encodes a polypeptide having PEAMT activity and that comprises an at least 27 contiguous amino acid sequence from SEQ ID NO:2; (b) encodes a polypeptide having PEAMT activity and at least about 75% sequence identity with the amino acid sequence of SEQ ID NO:2; (c) comprises an at least 26 contiguous nucleotide sequence from SEQ ID NO:1; or (d) hybridizes to the sequence of from position 254 to 1735 of SEQ ID NO: 1, or that hybridizes to the complement thereof, under stringent hybridization conditions.

Preferably the isolated polynucleotide comprises a sequence region that encodes a polypeptide having an at least 28 or 29 contiguous amino acid sequence from SEQ ID NO:2, although longer contiguous sequences such as at least 30, at least 31, at least 33, at least 35, or at least 37 or more contiguous amino acid sequence from SEQ ID NO:2 are also contemplated to be particularly preferred. In illustrative embodiments, the isolated polynucleotide comprises a sequence region that encodes a polypeptide comprising the sequence of SEQ ID NO:2.

The invention further provides an isolated polynucleotide that: (a) encodes a polypeptide having ΔPEAMT activity and that comprises an at least 27 contiguous amino acid sequence from SEQ ID NO:4; (b) encodes a polypeptide having ΔPEAMT activity and at least about 75% sequence identity with the amino acid sequence of SEQ ID NO:4; (c) comprises an at least 26 contiguous nucleotide sequence from SEQ ID NO:3; or (d) hybridizes to the sequence of SEQ ID NO:3, or that hybridizes to the complement thereof, under stringent hybridization conditions.

Preferably the isolated ΔPEAMT polynucleotide comprises a sequence region that encodes a polypeptide having an at least 28 or 29 contiguous amino acid sequence from SEQ ID NO:4, although longer contiguous sequences such as at least 30, at least 31, at least 33, at least 35, or at least 37 or more contiguous amino acid sequence from SEQ ID NO:4 are also contemplated to be particularly preferred. In illustrative embodiments, the isolated ΔPEAMT polynucleotide comprises a sequence region that encodes a polypeptide comprising the sequence of SEQ ID NO:4.

The isolated polynucleotides of the invention preferably comprise a sequence region that encodes a polypeptide having PEAMT or ΔPEAMT activity and at least about 70%, 75%, 78%, or 80% or greater sequence identity with the amino acid sequence of SEQ ID NO:2 or SEQ ID NO:4. More preferably, the polypeptides have at least about 85%, about 90%, about 95% or about 98% sequence identity with the amino acid sequence of SEQ ID NO:2 or SEQ ID NO:4.

Preferred polynucleotides of the present invention typically will comprise an at least 31 contiguous nucleotide sequence from SEQ ID NO: 1 or SEQ ID NO:3, although longer contiguous nucleotide sequences from SEQ ID NO:1 or SEQ ID NO: 3, such as about 33, about 35, about 37, about 39, about 40, about 45, about 50, about 55 or more contiguous nucleotide sequence from SEQ ID NO:1 or SEQ ID NO:3, are also highly preferred. In fact, the PEAMT- and ΔPEAMT-encoding polynucleotides may comprise all or substantially all of the nucleotide sequence of SEQ ID NO: 1 or SEQ ID NO:3.

Preferred polynucleotide compositions of the present invention typically will comprise a sequence region that hybridizes to the sequence of from position 254 to 1735 of SEQ ID NO: 1 or to the sequence of SEQ ID NO:3, under stringent hybridization conditions. Such stringent hybridizations are well known to those of skill in the art, as are the methods for obtaining and identifying polynucleotides that hybridize to a selected target sequence. For example, as described hereinbelow, stringent hybridization conditions comprising a salt concentration of from about 0.02 M to about 0.15 M, and a temperature of from about 50° C. to about 70° C. are particularly preferred.

A further embodiment of the present invention concerns an isolated polynucleotide that comprises: (a) a sequence region that consists of at least 26 contiguous nucleotides that have the same sequence as, or are complementary to, at least 26 contiguous nucleotides of SEQ ID NO: 1 or SEQ ID NO:3; or (b) a sequence region of from 26 to about 10000 nucleotides in length that hybridizes to the nucleic acid segment of SEQ ID NO:1 or SEQ ID NO:3; or the complement thereof, under hybridization conditions comprising a salt concentration of from about 0.02 M to about 0.15 M, and a temperature of from about 50° C. to about 70° C. Such polynucleotides may range in size from on the order of about 100 to about 11,000 nucleotides in length, with intermediate ranges such as from about 1000 to about 9,000 nucleotides in length, or from about 2000 to about 7,000 nucleotides in length, or from about 4000 to about 6000 nucleotides in length being particular preferred.

Preferred polynucleotide compositions will typically comprise an RNA, a PNA, or a DNA segment, as described hereinbelow. Such compositions may be comprised within a recombinant vector such as a plasmid, cosmid, phage, phagemid, baculovirus, bacterial artificial chromosome, or yeast artificial chromosome vector. Likewise, the disclosed polynucleotides may be comprised within a recombinant virus or virion. It may be operably linked to a promoter, and particularly to a heterologous promoter such as a plant-expressible constitutive, inducible, or tissue-specific promoter. Exemplary plant-expressible promoters include those listed herein in Table 1, Table 2, and Table 3, and include such well known promoters as corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, ALS, ubiquitin, globulin 1, cruciferin, napin, β-conglycinin, phaseolin, γ zein, or the S-E9 small subunit RuBP carboxylase promoter.

Such polynucleotides may be used, for example, in preparing a recombinant vector, a transgenic plant, or a recombinant polypeptide composition. Such polynucleotide compositions may also be used as a probe for screening a plant nucleic acid library to identify a gene encoding a polypeptide having PEAMT or ΔPEAMT activity. Alternatively, their sequence information may be used in the preparation of a target sequence probe to employ a computer-based algorithm to search a computerized database of sequences such as genomic, or expressed sequence tags, cDNAs, and the like to identify a gene encoding a polypeptide having PEAMT or ΔPEAMT activity.

The recombinant vectors of the present invention may also be used in producing a transformed plant cell or plant tissue, a pluripotent plant cell, or a transgenic plant that expresses a polypeptide having PEAMT or ΔPEAMT activity.

In a related embodiment, the invention provides a host cell that comprises such a recombinant vector that has at least a first heterologous expression unit comprising a PEAMT- or a ΔPEAMT-encoding polynucleotide. Such a host cell may be a bacterial cell such as an *Escherichia*, *Salmonella* or *Agrobacterium* cell, or alternatively, may be an eukaryotic cell, such as a plant cell. Alternatively, the polynucleotide may be comprised within a virus, virion, or viral vector. Exemplary recombinant vectors described in Example 1 have been designated pREP3-PEAMT and pREP3-ΔPEAMT, which encode PEAMT and ΔPEAMT polypeptides, respectively.

The invention also provides an isolated polypeptide encoded by the disclosed PEAMT polynucleotides. Such polypeptides preferably comprise an at least 27, 28, 29, 30, 31, 32 33, 34, 35, 36, 37, 38, 39, or 40 contiguous amino acid sequence from SEQ ID NO:2 or SEQ ID NO:4, and preferably share at least about 65%, about 70%, about 75%, about 80%, about 85%, about 90%, about 95%, or about 99% or higher sequence identity with the amino acid sequence of SEQ ID NO:2 or SEQ ID NO:4, which encode PEAMT and ΔPEAMT polypeptides, respectively.

Such polypeptides may be used in the preparation of an antibody that specifically binds to a PEAMT or a ΔPEAMT polypeptide, using the immunological methods described hereinbelow. The PEAMT- or ΔPEAMT-specific antibody compositions so produced that specifically binds to the disclosed PEAMT and ΔPEAMT polypeptides also represent an important embodiment of the present invention. Such antibodies may be suitably packaged in an immunodetection kit, along with an immunodetection reagent, and instructions for using the antibody in methods such as ELISAs and other immunoaffinity methodologies to detect the presence of PEAMT polypeptides in a target sample, such as in a plant or leaf extract.

The invention also provides nucleic acid detection kits that typically comprise in suitable container means, at least a first isolated nucleic acid segment comprising a PEAMT or a ΔPEAMT-encoding polynucleotide, a detection reagent, and instructions for using the PEAMT- or ΔPEAMT-specific nucleic acid segment to detect other PEAMT/ΔPEAMT sequences or to use as probes or primers for related and DNA sequencing methodologies and the like.

Compositions are also provided by the invention that comprise: (a) a PEAMT- or a ΔPEAMT-specific polynucleotide, (b) a PEAMT or a ΔPEAMT polypeptide, (c) a PEAMT- or a ΔPEAMT-specific antibody, (d) a recombinant vector, (e) virus, or (f) host cell that expresses a PEAMT or a ΔPEAMT polynucleotide or polypeptide.

The invention further provides a transgenic plant that comprises: (a) a heterologous nucleic acid segment that comprises a PEAMT or a ΔPEAMT polynucleotide; (b) a transformed host cell that expresses a PEAMT or a ΔPEAMT polypeptide; (c) a recombinant virus that expresses a PEAMT or a ΔPEAMT polypeptide; or (d) a recombinant vector that encodes a PEAMT or a ΔPEAMT polypeptide.

The transgenic plant preferably has stably incorporated into its genome a heterologous nucleic acid segment that comprises a PEAMT or a ΔPEAMT polynucleotide, wherein the polynucleotide is operably linked to a promoter that expresses the polynucleotide in the cells and tissues of the transgenic plant. Such transgenic plants are preferably monocotyledonous or dicotyledonous plants, such as grains, trees, legumes, fibers, vegetables, fruits, berries, nuts, citrus, grasses, cacti, succulents, flowers, or other ornamental plants.

Exemplary plants include, but are not limited to, corn, rice, millet, tobacco, alfalfa, soybean, bean, sorghum, pea, *Brassica*, safflower, potato, coconut, palm, pumpkin, squash, poppy, sesame, peanut, cocoa, coffee, tomato, flax, sugar beets, canola, sunflower, cotton, kapok, wheat, oat, barley, walnut, pecan, almond, and rye.

The invention further discloses and claims progeny of any generation of such transgenic plant, as well as the seed of any generation of such transgenic plants, and seed of any generation, offspring, or subsequent progeny of such transgenic plants. Particularly encompassed by the invention are seeds, nuts, legumes, and the like, that have an increased level of lipid, relative to untransformed plants of the same species that do not contain one or more exogenously provided PEAMT- or ΔPEAMT-encoding transgenes. Such seeds are particularly preferred for animal foodstuffs, as well as those having increased protein and nutrition content suitable for human consumption.

The invention also provides hereinbelow methods for detecting a PEAMT- or a ΔPEAMT-encoding polynucleotide in a sample. Such a method typically involves the steps of: (a) contacting a population of polynucleotides suspected of encoding a PEAMT or a ΔPEAMT polypeptide with at least a first labeled PEAMT/ΔPEAMT polynucleotide, under conditions effective to allow hybridization of substantially complementary nucleic acids; and (b) detecting the hybridized complementary nucleic acids so formed.

A method is also provided for detecting a PEAMT or a ΔPEAMT polypeptide in a biological sample. This method typically involves contacting a biological sample suspected of containing a PEAMT or a ΔPEAMT polypeptide with a labeled PEAMT- or ΔPEAMT-specific antibody, under conditions effective to allow the formation of immune complexes, and detecting the immune complexes so formed.

The invention also provides a method of identifying a gene encoding a plant PEAMT polypeptide. The method generally involves expressing a plurality of plant polynucleotides suspected of encoding a plant PEAMT polypeptide in a polupion of Schizosaccharomyces pombe cho2$^-$, cells, and selecting at least a first cell from said population that is capable of growth on a minimal medium comprising ethanolamine under conditions effective for the growth of the cell, where growth of a cell is indicative of the cell's containing a PEAMT-encoding polynucleotide. Such complementation methods are described in detail hereinbelow in Example 1.

A method is also provided for increasing the amount of a PEAMT or a ΔPEAMT polypeptide in a plant cell. This method typically involves expressing in such a plant cell a biologically effective amount of a PEAMT- or a ΔPEAMT-specific polynucleotide. The term "biologically effective amount" will be understood by the skilled artisan to mean an amount of the polynucleotide composition that is effective to produce the desired phenotypic trait in the resulting transformed plant cell, i.e. an increased level or amount of PEAMT/ΔPEAMT polypeptide or PEAMT/ΔPEAMT enzymatic activity in the cell when compared to a similar untransformed or "wild-type" plant cell.

A method of increasing the level of a compound selected from the group consisting of phosphatidylcholine, phosphocholine, choline, choline-O-sulfate and glycine betaine in a plant cell is also provided by the invention. This method generally comprises, expressing in a suitable plant cell a biologically effective amount of a PEAMT or a ΔPEAMT polynucleotide. Such an effective amount will be recognized by the skilled artisan as an amount necessary to alter, increase, or improve the level or extent of one or more of the choline metabolites in the plant cells and plant tissues. This method is particularly useful for increasing the level of or altering the lipid content of the cells, fruits, seeds, and tissues of the transformed plant, and for modulating the tolerance of the plant to osmotic or cryogenic stress.

This method provides means for modulating the biosynthesis of phosphatidylcholine, phosphocholine, choline, or metabolites thereof, such as, but not limited to, glycine betaine or choline-O-sulfate in a plant, increasing the lipid level or altering the lipid compositions of plant cells, or improving the overall nutritional value of the plant for consumption by animals and/or humans.

Using the PEAMT compositions of the invention, it is possible to regulate the level of one or more cellular lipids in a transformed host cell expressing these compositions. This method provides means for modulating the biosynthesis of the osmoprotecting and cryoprotecting compounds of a cell such as glycine betaine and choline-O-sulfate. Such methods may further involve transforming the cell with an additional nucleic acid construct that encodes an enzyme involved in glycine betaine or choline-O-sulfate biosynthesis. Such enzymes may include for example, choline monooxygenase, choline oxidase, or choline dehydrogenase. The method may further comprise altering the level of the PEAMT precursors, phosphoethanolamine and/or ethanolamine to provide greater intracellular pools of the substrate for the PEAMT enzyme. The transformation of selected plants with one or more genetic constructs encoding choline monooxygenase, choline oxidase, or choline dehydrogenase may be required when the plant lacks such enzymes, as is the case with plants such as potatoes and rice. Also, it may be desirable to augment the level of one or more of these glycine betaine biosynthetic enzymes in plants that natively expres one or more of such enzymes. This may be the case when transforming crops such as barley, corn, and sugar beets.

An exemplary method may further comprise the steps of growing the transformed plant under conditions effective for obtaining seeds from the plant, and collecting the seeds so produced by the transformed plant. This method is particularly desirable for the recovery of high-nutritional value seeds, grains, nuts, flours, and the like. The method is particularly desirable for the recovery of seeds having altered lipid content, or an altered distribution of the lipids native to the seed of the particular species from which the seed was obtained, when compared to an unmodified seed of the same species. The method may also further comprise the step of (e) transforming the plant cell with one or more additional polynucleotides that encode one or more phosphatidylcholine biosynthesis enzymes, such as one or more enzymes in the pathway for phosphocholine synthesis, to further increase in the cells and tissues of the plant the level of phosphatidylcholine, or to otherwise alter the lipid content of the cells. Increasing the amount of phosphatidylcholine or altering the lipid content of plant seed, may be achieved by further growing such a transgenic plant, under conditions effective to produce seed and then obtaining the seed produced from the plant.

2.1 Polypeptide Compositions

In a first embodiment, the invention provides polypeptides, peptides and proteins that comprise all, substantially all, or portions of a PEAMT or a ΔPEAMT enzyme. Highly preferred PEAMT polypeptides are those that comprise an at least about 27, an at least about 28, an at least about 29, an at least about 30, an at least about 31, or an at least about 32 or more contiguous amino acid sequence from SEQ ID NO:2, and that have PEAMT enzymatic activity when expressed in a suitable plant host cell cultured under the appropriate conditions for such enzymatic activity. Likewise, PEAMT polypeptides that comprise an at least about 33 or 34 or 35 or 36 contiguous amino acid sequence from SEQ ID NO:2, and that have PEAMT enzymatic activity when expressed in a suitable plant host cell are also contemplated to be particularly useful in the methods disclosed herein.

Highly preferred ΔPEAMT polypeptides are those that comprise an at least about 27, an at least about 28, an at least about 29, an at least about 30, an at least about 31, or an at least about 32 or more contiguous amino acid sequence from SEQ ID NO:4, and that have ΔPEAMT enzymatic activity when expressed in a suitable plant host cell cultured under the appropriate conditions for such enzymatic activity. Likewise, ΔPEAMT polypeptides that comprise an at least about 33 or 34 or 35 or 36 contiguous amino acid sequence from SEQ ID NO:4, and that have ΔPEAMT enzymatic activity when expressed in a suitable plant host cell are also contemplated to be particularly useful in the methods disclosed herein.

In certain circumstances, it may be desirable to employ PEAMT or ΔPEAMT polypeptides that are even more homologous to the sequences disclosed in SEQ ID NO:2 or SEQ ID NO:4. In those embodiments, the PEAMT or ΔPEAMT polypeptides of the invention will preferably comprise a primary amino acid sequence that comprises an at least about 37, and at least about 38, an at least about 39, an at least about 40, an at least about 41, an at least about 42, an at least about 43, an at least about 44, an at least about 45, or an at least about 50 or so contiguous amino acid sequence selected from one or more of the sequences of SEQ ID NO:2 or SEQ ID NO:4. Likewise, in other embodiments, it may be desirable to employ PEAMT or ΔPEAMT polypeptides that are even more homologous to the sequences disclosed in SEQ ID NO:2 or SEQ ID NO:4. In those embodiments, the PEAMT or ΔPEAMT polypeptides of the invention will preferably comprise a primary amino acid sequence that comprises an at least about 55, and at least about 60, an at least about 65, an at least about 70, an at least about 75, or an at least about 80 or so contiguous amino acid sequence selected from one or more of the sequences of SEQ ID NO:2 or SEQ ID NO:4. In fact, when more highly homologous PEAMT or ΔPEAMT polypeptides are contemplated, those having an at least about 85, and at least about 90, an at least about 95, an at least about 100, an at least about 110, an at least about 120, an at least about 125, an at least about 130, an at least about 135, an at least about 140, an at least about 145, or an at least about 150, or so contiguous amino acid sequence selected from one or more of the sequences of SEQ ID NO:2 or SEQ ID NO:4 will be particularly preferred.

Shorter peptide and polypeptide sequences comprised with one or more of the disclosed PEAMT or ΔPEAMT proteins are also within the scope of the present invention. Such peptides may be utilized as described herein in the preparation of epitopes, or used as antigens for the generation of PEAMT- or ΔPEAMT-specific antibodies, or may even be used to screen antibody samples for species that specifically bind to a PEAMT/ΔPEAMT peptide motif. Such smaller peptides include, but are not limited to sequences that comprise at least 27 contiguous amino acids as set forth in SEQ ID NO:2 or SEQ ID NO:4. These peptides are particularly useful as probes for identifying polypeptides of the PEAMT/ΔPEAMT family that share conserved regions.

2.2 Polynucleotide Compositions

In a second embodiment, the invention concerns polynucleotides that encode the PEAMT and ΔPEAMT polypeptides of the present invention. For polynucleotides encoding PEAMT polypeptides, such sequences preferably comprise from at least about 27, to at least about 2100 or more contiguous nucleotides from SEQ ID NO:1. As such, polynucleotides that comprise at least about 30 to about 2000 or more contiguous nucleotides from SEQ ID NO: 1 are contemplated to be particularly preferred in the methods of the present invention. Similarly, polynucleotides that comprise at least about 40 to about 1800 or more contiguous nucleotides from SEQ ID NO:1 are also contemplated to be particularly preferred in the methods of the present invention, as are those polynucleotides that comprise at least about 50 to about 1600 or more contiguous nucleotides from SEQ ID NO:1, and those polynucleotides that comprise at least about 60 to about 1400 or more contiguous nucleotides from SEQ ID NO:1.

For polynucleotides encoding ΔPEAMT polypeptides, such sequences preferably comprise from at least about 27, to at least about 1100 or more contiguous nucleotides from SEQ ID NO:3. As such, polynucleotides that comprise at least about 30 to about 1000 or more contiguous nucleotides from any one of SEQ ID NO:3 are contemplated to be particularly preferred in the methods of the present invention. Similarly, polynucleotides that comprise at least about 40 to about 900 or more contiguous nucleotides from SEQ ID NO:3 are also contemplated to be particularly preferred in the methods of the present invention, as are those polynucleotides that comprise at least about 50 to about 800 or more contiguous nucleotides from SEQ ID NO:3, and those polynucleotides that comprise at least about 60 to about 700 or more contiguous nucleotides from SEQ ID NO:3.

Naturally, all intermediate contiguous sequences are contemplated to fall within the scope of the present invention. For example, polynucleotides that comprise at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 85, at least about 90, at least about 95, or at least about 100 or more contiguous nucleotides from SEQ ID NO:1 or SEQ ID NO:3 are contemplated to be particularly preferred in the methods of the present invention, and are contemplated to be particularly preferred polynucleotide compositions.

Likewise, PEAMT- and ΔPEAMT-encoding polynucleotides that comprise at least about 110, at least about 120, at least about 130, at least about 140, at least about 150, at least about 160, at least about 170, at least about 180, at least about 190, or at least about 200 or more contiguous nucleotides from SEQ ID NO: 1 or SEQ ID NO:3 are contemplated to be particularly preferred polynucleotide compositions. PEAMT-specific polynucleotides that comprise at least about 250, at least about 300, at least about 350, at least about 400, at least about 450, at least about 500, at least about 550, at least about 600, or more contiguous nucleotides from SEQ ID NO:1 or SEQ ID NO:3 are contemplated to be particularly preferred polynucleotide compositions.

When it is desirable to employ PEAMT- or ΔPEAMT-encoding polynucleotides that are significantly more homologous to the polynucleotide sequences disclosed herein, polynucleotide compositions may be selected that encode PEAMT- or ΔPEAMT-derived peptides that comprise at least about 650, at least about 700, at least about 750, at least about 800, at least about 850, at least about 900, at least about 950, at least about 1000, at least about 1050, at least about 1100 or more contiguous nucleotides from SEQ ID NO:1 or SEQ ID NO:3, and even those up to and including the full-length DNA sequence disclosed in SEQ ID NO:3 are contemplated to be particularly preferred polynucleotide compositions. Likewise, those sequences that comprise at least about 1200, about 1300, about 1400, about 1500, about 1600, about 1700, about 1800, about 1900, about 2000, about 2100, about 2200, and even those up to and including the full-length DNA sequence of SEQ ID NO:1 are also contemplated to be particularly preferred polynucleotide compositions.

Likewise, the PEAMT and ΔPEAMT polynucleotide compositions of the present invention also encompass those nucleic acid segments that encode a polypeptide having PEAMT or ΔPEAMT activity, and that comprise a nucleic acid sequence of at least about 7 or 8 contiguous amino acids from SEQ ID NO:2 or SEQ ID NO:4, respectively. In more preferred embodiments, the PEAMT and ΔPEAMT polypeptides of the present invention comprise an at least about 9 or 10 contiguous amino acid sequence from one of these full-length sequences, respectively. When it is desirable to identify PEAMT and ΔPEAMT polypeptides that are still more homologous to the disclosed sequences, one may wish to utilize PEAMT and ΔPEAMT polypeptides that comprise an at least about 11, about 12, about 13, or about 14 or more contiguous amino acid sequence from SEQ ID NO:2 or SEQ ID NO:4, respectively.

2.3 Compositons for Gene Detection, Amplification, and Sequencing

In related embodiments, the invention provides methods and compositions for detecting homologous PEAMT/ΔPEAMT-encoding polynucleotides and homologous PEAMT/ΔPEAMT polypeptides.

For detection and sequencing of polynucleotides, it is often desirable to isolate smaller polynucleotides for use as hybridization probes, synthesis or sequencing primers, and the like as described in detail herein. In such embodiments, shorter polynucleotide sequences are particularly desirable, including those that comprise a sequence of at least about 30 or 40 or 50 or so contiguous nucleotides from one or more of the DNA sequences disclosed in SEQ ID NO: 1 and SEQ ID NO:3. These sequences find particular utility as probes for screening clone banks, colony blots, or as computer homology search strings for identifying homologous polynucleotide sequences via computer-based algorithm homology searches. This is particularly important when it is desirable to screen a database of cDNA sequences, expressed sequence tags (ESTs) or genomic or chromosomal sequence databases.

For example, polynucleotides that comprise at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, or even at least about 60 or so nucleotides from one of the disclosed sequences are particularly suited for these embodiments.

2.4 Identification of Homologous PEAMT Polypeptides and Polynucleotides

In addition to the particular illustrative polypeptide and polynucleotide sequences disclosed herein, those having benefit of the present teaching are now also able to identify and characterize a wide variety of PEAMT and ΔPEAMT homologs and/or isozymes, as well as to identify, characterize, and sequence a variety of PEAMT/ΔPEAMT-encoding polynucleotides from a variety of plant species. In fact, the inventors contemplate that any plant-derived PEAMT/ΔPEAMT protein or peptide can be identified using the methods disclosed herein and may be obtained by using the immunological methods disclosed herein to obtain PEAMT/ΔPEAMT proteins and peptides from a variety of disparate species. Alternatively, the inventors contemplate that those of skill in the art having the benefit of the teachings disclosed herein will be able to identify PEAMT/ΔPEAMT-encoding polynucleotides either by comparison of one or more of the disclosed sequences to computer databases of plant EST sequences, and identification of highly homologous sequences, or alternatively, by traditional hybridization screening methods employing one or more labeled PEAMT- or ΔPEAMT-specific polynucleotide sequences to screen a population of target nucleic acids, such as e.g., a cDNA or other such genetic library, a colony or clone bank, or by screening individual isolates from particular plant species.

Because the inventors have successfully demonstrated the presence of PEAMT-specific polynucleotides and polypeptides in at least two plant genera (i.e. *Spinacia oleracea* and *Arabidopsis*), they contemplate the additional identification of related PEAMT and ΔPEAMT polypeptides and the gene sequences that encode them. In particular, the inventors contemplate the identification of PEAMT variants, homologs, and related sequences using one or more of the methods disclosed herein to identify a family of PEAMT sequences. Likewise, one of skill in the art will even be able to utilize the teachings of the present disclosure to identify other PEAMT-like polypeptides and polynucleotides, including those from related and from distantly-related plant species and to use these sequences in the preparation of transgenic plants having modified lipid content or altered PEAMT-dependent biosyntheses. By hybridization, immunological, and computer-based homology algorithms, the inventors further contemplate the identification and characterization of PEAMT-specific compositions from species that are not yet even described or characterized as possessing PEAMT activity.

In addition to the particular full-length PEAMT polypeptides disclosed in SEQ ID NO:2 and the ΔPEAMT sequence shown in SEQ ID NO:4, the inventors also contemplate the preparation and use of substantially fill-length sequences in certain embodiments. As such, polypeptides may be obtained that comprise from at least about 80% or so, and up to and including those having at least about 99% of the full-length PEAMT primary amino acid sequence as disclosed herein, and yet still possess significant PEAMT enzymatic activity in vitro and in vivo. In fact, "truncated" polypeptides or "near-full-length" or "substantially full-length" polypeptides are well known in the plant molecular biological arts to often possess all, or almost all of the enzymatic activity that the fill-length polypeptide possesses. In many embodiments, these slightly shorter polypeptide sequences may be desirable for use in many of the disclosed methods. This is particularly true, when the creation of "chimeric" polypeptides is desired, as well as in the creation of hybrid polypeptides that have, for example, the addition of a particular amino acid sequence to "target" the localization of the polypeptide to a particular cellular location, or to a particular region of the plant in which the polypeptide is expressed. For example, the preparation of a fusion protein that possesses both PEAMT activity, yet further comprises a sequence region that targets the peptide to a particular cellular region, such as the membrane, or to a particular organelle, etc. is often desirable. As such, truncated or fusion proteins that comprise only about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the primary amino acid sequence as disclosed in SEQ ID NO:2 or SEQ ID NO:4 are particularly embodied by the present invention.

In the same that a PEAMT polypeptide need not include the entire sequences as disclosed in SEQ ID NO:2 and SEQ ID NO:4 to be useful in the practice of the present methods, the primary amino acid sequence of a particular PEAMT polypeptide need not have complete sequence identity to either of the polypeptides disclosed in SEQ ID NO:2 and SEQ ID NO:4. In fact, the primary amino acid sequence of a particular PEAMT polypeptide need only comprise enough of the primary PEAMT sequence to substantially perform its enzymatic function in vivo or in situ. Owing to the nature of conservative amino acid replacement, indeed several amino acids may be changed, altered, mutagenized, or even deleted in the primary amino acid sequence of a particular PEAMT protein and yet still give rise to a functional PEAMT polypeptide which still possesses an enzymatic activity similar or identical to that of the native full-length PEAMTs disclosed in the following examples.

In fact, it is well known in the plant molecular biological arts that two polypeptides from different species may differ slightly, or even sometimes, substantially in their primary amino acid sequence, and yet, still possess the same biological activity. As such, homologous or "cognate" PEAMT polypeptides may be designed synthetically, site-specifically modified, or isolated from different biological sources, that possess similar PEAMT enzymatic activity, but yet share less than 100% identity at the primary amino acid level with one of the PEAMT sequences disclosed herein. In fact, such PEAMT homologous polypeptides may share approximately 60% or 65% sequence identity with one or more of the disclosed sequences herein. More homologous PEAMT sequences will include those polypeptides that are from about 70% to about 80% identical to either of the polypeptides of SEQ ID NO:2 or SEQ ID NO:4. Still more homologous PEAMT sequences will include those polypeptides that share from about 85% to about 95% sequence identity with one or more of the polypeptides disclosed in SEQ ID NO:2 or SEQ ID NO:4.

When highly homologous polypeptide are identified that possess PEAMT enzymatic activity, such as is often the case when polypeptides are obtained from closely-related species, cultivars, or hybrids, the PEAMT polypeptides identified may share about 96%, about 97%, about 98%, or even about 99% or more sequence identity with one or more of the sequences disclosed in SEQ ID NO:2 or SEQ ID NO:4. Naturally, all intermediate % identity values are contemplated to fall within the scope of the present disclosure. As such, polypeptides having about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, and those having about 98% primary amino acid sequence identity to the sequences disclosed in SEQ ID NO:2 or SEQ ID NO:4 are contemplated to be useful in the formulation of the methods and compositions of the present invention.

In preferred embodiments, the PEAMT polypeptides of the present invention comprise an at least about 7 or 8 contiguous amino acid sequence from SEQ ID NO:2 or SEQ ID NO:4. Likewise, the PEAMT compositions of the present invention also encompass those polypeptides that have PEAMT activity, and that comprise an amino acid sequence of at least about 9 or 10 contiguous amino acids from SEQ ID NO:2 or SEQ ID NO:4. In more preferred embodiments, the PEAMT polypeptides of the present invention comprise an at least about 11 or 12 contiguous amino acid sequence from one of these full-length sequences. When it is desirable to identify PEAMT polypeptides that are still more homologous to the disclosed sequences, one may wish to utilize PEAMT polypeptides that comprise an at least about 13 or 14 or 15 or 16 contiguous amino acid sequence from SEQ ID NO:2 or SEQ ID NO:4.

Highly preferred PEAMT polypeptides are those that comprise an at least about 17 or 18 or 19 or 20 contiguous amino acid sequence from SEQ ID NO:2 or SEQ ID NO:4, and that have PEAMT enzymatic activity when expressed in a suitable plant host cell cultured under the appropriate conditions for PEAMT expression and enzymatic activity. Likewise, PEAMT polypeptides that comprise an at least about 21 or 22 or 23 or 24 contiguous amino acid sequence from SEQ ID NO:2 or SEQ ID NO:4, and that have PEAMT enzymatic activity when expressed in a suitable plant host cell are also contemplated to be particularly useful in the methods disclosed herein.

In certain circumstances, it may be desirable to employ PEAMT polypeptides that are even more homologous to the sequences disclosed in SEQ ID NO:2 or SEQ ID NO:4. In those embodiments, the PEAMT polypeptides of the invention will preferably comprise a primary amino acid sequence that comprises an at least about 25, and at least about 30, an at least about 35, an at least about 40, an at least about 45, or an at least about 50 or so contiguous amino acid sequence selected from SEQ ID NO:2 or SEQ ID NO:4. Likewise, in other embodiments, it may be desirable to employ PEAMT polypeptides that are even more homologous to the sequences disclosed in SEQ ID NO:2 and SEQ ID NO:4. In those embodiments, the PEAMT polypeptides of the invention will preferably comprise a primary amino acid sequence that comprises an at least about 55, and at least about 60, an at least about 65, an at least about 70, an at least about 75, or an at least about 80 or so contiguous amino acid sequence selected from SEQ ID NO:2 or SEQ ID NO:4. In fact, when more highly homologous PEAMT polypeptides are contemplated, those having an at least about 85, and at least about 90, an at least about 95, an at least about 100, an at least about 110, an at least about 120, an at least about 125, an at least about 130, an at least about 135, an at least about 140, an at least about 145, or an at least about 150, or so contiguous amino acid sequence selected from SEQ ID NO:2 or SEQ ID NO:4 will be particularly preferred.

2.5 Recombinant Vectors

One important embodiment of the invention is a recombinant vector that comprises a nucleic acid segment encoding one or more of the novel polypeptides disclosed herein. Such a vector may be transferred to and replicated in a prokaryotic or eukaryotic host with bacterial cells being particularly preferred as prokaryotic hosts, and plant cells being particularly preferred as eukaryotic hosts. In preferred embodiments, the recombinant vector comprises a nucleic acid segment encoding the amino acid sequence of SEQ ID NO:2 or SEQ ID NO:4. Highly preferred nucleic acid segments are those which comprise an at least 31 basepair contiguous sequence from SEQ ID NO:1 or SEQ ID NO:3.

Another important embodiment of the invention is a transformed host cell that expresses one or more of these recombinant vectors. The host cell may be either prokaryotic or eukaryotic, and particularly preferred host cells are those that express the nucleic acid segment(s) comprising the recombinant vector that encodes one or more PEAMT polypeptides. Bacterial cells are particularly preferred as prokaryotic hosts, and plant cells are particularly preferred as eukaryotic hosts.

In accordance with the present invention, nucleic acid sequences include and are not limited to DNA, including and not limited to cDNA and genomic DNA, genes; RNA, including and not limited to mRNA and tRNA; PNAs (peptide nucleic acids), antisense sequences, nucleosides, and suitable nucleic acid sequences such as those set forth herein, as well as variants in the nucleic acid sequences such as alterations, deletions, mutations, and homologs capable of expressing the PEAMT polypeptides of the present invention.

As such the present invention also concerns DNA segments, that are free from total genomic DNA and that encode the novel PEAMT proteins disclosed herein. DNA segments encoding these peptide species may prove to encode proteins, polypeptides, subunits, functional domains, and the like of PEAMT-related or other non-related gene products. In addition these DNA segments may be synthesized entirely in vitro using methods that are well known to those of skill in the art.

As used herein, the term "DNA segment" refers to a DNA molecule that has been isolated free of total genomic DNA of a particular species. Therefore, a DNA segment encoding a PEAMT polypeptide or peptide refers to a DNA segment that contains PEAMT polypeptide coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified nucleic acid or gene sequence that encodes a PEAMT polypeptide refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a PEAMT polypeptide, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a PEAMT peptide or polypeptide species that includes within its amino acid sequence an amino acid sequence essentially as set forth in SEQ ID NO:2 or SEQ ID NO:4.

The term "a sequence essentially as set forth in SEQ ID NO:2 or SEQ ID NO:4" means that the sequence substantially corresponds to a portion of the sequence of SEQ ID NO:2 or SEQ ID NO:4, and has relatively few amino acids that are not identical to, or a biologically functional equivalent of, the amino acids of any of these sequences. The term "biologically functional equivalent" is well understood in the art and is further defined in detail herein (e.g., see Illustrative Embodiments).

Accordingly, sequences that have between about 65% and about 75% or between about 75% and about 85%, or more preferably between about 86% and about 90%, or even more preferably between about 91% or 92% or 93% and about 97% or 98% or 99% amino acid sequence identity or functional equivalence to the amino acids of SEQ ID NO:2 or SEQ ID NO:4, will be sequences that are "essentially as set forth in SEQ ID NO:2 or SEQ ID NO:4."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e. introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch encoding the peptide sequence disclosed in SEQ ID NO:2 or SEQ ID NO:4, or that are identical to or complementary to DNA sequences which encode the peptide disclosed in SEQ ID NO:2 or SEQ ID NO:4, and particularly the DNA segments disclosed in SEQ ID NO:1 or SEQ ID NO:3.

Highly preferred nucleic acid segments of the present invention comprise one or more PEAMT-encoding genes of the invention, or a portion of one or more PEAMT-encoding genes of the invention. For certain application, relatively small contiguous nucleic acid sequences are preferable, such as those which are about 14 or 15 or 16 or 17 or 18 or 19, or 20, or 21, or 22, or 23, or 24, or 25, or 26, or 27, or 28, or 29, or 30–50, 51–80, 81–100 or so nucleotides in length.

Alternatively, in some embodiments, and particularly those involving preparation of recombinant vectors, transformation of suitable host cells, and preparation of transgenic plant cell, longer nucleic acid segments are preferred, particularly those that include the entire coding region of one or more PEAMT-encoding genes. As such, the preferred segments may include those that are up to about 20,000 or so nucleotides in length, or alternatively, shorter sequences such as those about 19,000, about 18,000, about 17,000, about 16,000, about 15,000, about 14,000, about 13,000, about 12,000, 11,000, about 10,000, about 9,000, about 8,000, about 7,000, about 6,000, about 5,000, about 4,500, about 4,000, about 3,500, about 3,000, about 2,500, about 2,000, about 1,500, about 1,000, about 500, or about 200 or so base pairs in length. Of course, these numbers are not intended to be exclusionary of all possible intermediate lengths in the range of from about 20,000 to about 15 nucleotides, as all of these intermediate lengths are also contemplated to be useful, and fall within the scope of the present invention.

It will be readily understood that "intermediate lengths", in these contexts, means any length between the quoted ranges, such as 14, 15, 16, 17, 18, 19, 20, etc.; 21, 22, 23, 24, 25, 26, 27, 28, 29, etc.; 30, 31, 32, 33, 34, 35, 36 . . . etc.; 40, 41, 42, 43, 44 . . . etc., 50, 51, 52, 53 . . . etc.; 60, 61, 62, 63 . . . etc., 70, 80, 90, 100, 110, 120, 130 . . . etc.; 200, 210, 220, 230, 240, 250 . . . etc.; including all integers in the entire range from about 14 to about 10,000, including those integers in the ranges 200–500; 500–1,000; 1,000–2,000; 2,000–3,000; 3,000–5,000 and the like.

In a preferred embodiment, the nucleic acid segments comprise a sequence of from about 1800 to about 18,000 base pair in length, and comprise one or more genes that encode a PEAMT polypeptide as disclosed in SEQ ID NO:2 or SEQ ID NO:4, and particularly those polynucleotide sequences disclosed in SEQ ID NO:1 or SEQ ID NO:3.

It will also be understood that this invention is not limited to the particular nucleic acid sequences which encode peptides of the present invention, or which encode the amino acid sequence of SEQ ID NO:2 or SEQ ID NO:4, including the DNA sequences which are particularly disclosed in SEQ ID NO:1 and SEQ ID NO:3. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.6 Transformed Host Cells and Transgenic Plants

In one embodiment, the invention provides a transgenic plant having incorporated into its genome a transgene that encodes a contiguous amino acid sequence from SEQ ID NO:2 or SEQ ID NO:4. A further aspect of the invention is a transgenic plant having incorporated into its genome a transgene, that comprises an at least 27 basepair contiguous nucleic acid sequence from SEQ ID NO:1 or SEQ ID NO:3. Also disclosed and claimed are progeny of such a transgenic plant, as well as its seed, progeny from such seeds, and seeds arising from the second and subsequent generation plants derived from such a transgenic plant.

In yet another aspect, the present invention provides methods for producing a transgenic plant that expresses a nucleic acid segment encoding the novel PEAMT proteins of the present invention. The process of producing transgenic plants is well known in the art. In general, the method comprises transforming a suitable host cell with one or more DNA segments that contain one or more promoters operatively linked to a coding region that encodes one or more of the disclosed PEAMT proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant PEAMT expressed in a particular transgenic cell, the invention also provides for the expression of PEAMT-specific antisense mRNA. The use of antisense mRNA as a means of controlling or decreasing the amount of a given protein of interest in a cell is well known in the art.

Another aspect of the invention comprises a transgenic plant that expresses a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more PEAMT-encoding transgenes, either native, synthetically modified, or mutated. In some instances, more than one transgene will be incorporated into the genome of the transformed host plant cell. Such is the case when more than one PEAMT-encoding DNA segment is incorporated into the genome of such a plant. In certain situations, it may be desirable to have one, two, three, four, or even more PEAMT polypeptides (either native or recombinantly-engineered) incorporated and stably expressed in the transformed transgenic plant.

A preferred gene that may be introduced includes, for example, a PEAMT polypeptide-encoding a DNA sequence from plant origin, such as those illustrated herein, and particularly one or more of those comprising one or more amino acid sequences described in SEQ ID NO:2 or SEQ ID NO:4.

Means for transforming a plant cell and the preparation of a transgenic cell line are well known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed PEAMT polypeptides. These DNA constructs can further include structures such as promoters, enhancers, polylinkers, or even gene sequences that have positively- or negatively-regulating activity upon the particular genes of interest as desired. The DNA segment or gene may encode either a native or modified PEAMT polypeptide, which will be expressed in the resultant recombinant cells, and/or which will impart an improved phenotype to the regenerated plant, in this case, by altering or modulating the biosynthesis or lipid content in a transformed plant cell.

Such transgenic plants may be desirable for increasing lipid biosynthesis in a monocotyledonous or dicotyledonous plant, by incorporating into such a plant, a transgenic DNA segment encoding a PEAMT polypeptide. Particularly preferred plants include grains such as corn, wheat, millet, rye, rice, barley, and oats; legumes such as beans, soybeans, peas; tubers such as potatoes; fiber crops such as flax and cotton; turf and pasture grasses; tobacco, sunflower, safflower, canola, ornamental plants; shrubs; trees; vegetables, berries, citrus, fruits, cacti, succulents, and other commercially-important crops including garden, floral, and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PEAMT transgene(s) stably incorporated into its genome, and such progeny plants will inherit the traits afforded by the introduction of a stable transgene in Mendelian fashion. All such transgenic plants having incorporated into their genome transgenic DNA segments encoding one or more PEAMT polypeptides or polypeptides are aspects of this invention. Particularly preferred transgenes for the practice of the invention include nucleic acid segments comprising one or more PEAMT gene(s).

2.7 Recombinant Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a PEAMT polypeptide or peptide in its natural environment.

Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology; for example, see Sambrook et al., 1989. The promoters employed may be constitutive, or inducible, and can be used under the appropriate conditions to direct high level expression of the introduced DNA segment, such as is advantageous in modulating lipid biosynthesis or lipid composition of a cell expressing such genetic constructs. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of PEAMT peptides or epitopic core regions, such as may be used to generate anti-PEAMT antibodies, also falls within the scope of the invention. DNA segments that encode peptide antigens of about 8, 9, 10, 11, 12, 13, 14, 15, 16, 17, 18, 19, 20 or so amino acids, and up to and including those of about 25, 30, 35, 40, 45, 50, 55, 60, 65, 70, or 75 or so amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequence from SEQ ID NO:2 or SEQ ID NO:4.

Preferably for recombinant protein expression, the polynucleotide comprises at least a first heterologous promoter that directs the expression of the encoded polypeptide in the host cell. The polypeptide may be operably linked to one or more targeting sequences or signal peptides to permit expression of the polypeptide product in a particular cellular location or cell type.

In one embodiment, the invention encompasses a method of using a nucleic acid segment of the present invention that encodes a PEAMT polypeptide. The method generally comprises the steps of: (a) preparing a recombinant vector in which an -encoding nucleic acid segment is positioned under the control of a promoter, (b) introducing the recombinant vector into a host cell; (c) culturing the host cell under conditions effective to allow expression of the polypeptide encoded by the sequence; and (d) obtaining the expressed protein or peptide.

A wide variety of ways are available for introducing a suitable nucleic acid segment into the microorganism or eukaryotic host under conditions that allow for stable maintenance and expression of the nucleic acid segment that encodes the polypeptide. One can provide for DNA constructs that include the transcriptional and translational regulatory signals for expression of the PEAMT sequence, the sequence under their regulatory control and a DNA sequence homologous with a sequence in the host organism, whereby integration will occur, and/or a replication system that is functional in the host, whereby integration or stable maintenance will occur.

The transcriptional initiation signals will preferably include at least a first promoter and at least a first transcriptional initiation start site. In some instances, it may be desirable to provide for regulative expression of the enzyme, where expression of the polypeptide will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a polypeptide, but upon release into the environment, expression would begin. Other techniques may employ a specific nutrient medium in the laboratory, which inhibits the expression of the polypeptide, where the nutrient medium in the environment would allow for expression of the polypeptide. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a nucleotide sequence involving a marker, where the second nucleotide sequence may be joined to the toxin expression construct during introduction of the nucleotide into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores may be introduced into the host along with the structural gene expressing the toxin. In this manner, the enhanced expression of a siderophore may provide for a competitive advantage for the PEAMT-producing host, so that it may effectively compete with the wild-type microorganisms and stably occupy a niche in the environment.

Where no functional replication system is present, the construct will also include a sequence of at least 50 basepairs (bp), preferably at least about 100 bp, more preferably at least about 1000 bp, and usually not more than about 2000 bp of a sequence homologous with a sequence in the host. In this way, the probability of legitimate recombination is enhanced, so that the gene will be integrated into the host and stably maintained by the host. Desirably, the PEAMT gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, *cyanobacteria*, algae, fungi, and the like. Various transcriptional regulatory regions include the regions associated with the trp gene, lac gene, gal gene, the $\lambda_L$ and $\lambda_R$ promoters, the tac promoter, the naturally-occurring promoters associated with the δ-endotoxin gene, where functional in the host. See for example, U.S. Pat. Nos. 4,332,898; 4,342,832; and 4,356,270 (each of which is specifically incorporated herein by reference). The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system that is functional in the host. The replication system may be derived from the chromosome, an episomal element normally present in the host or a different host, or a replication system from a virus that is stable in the host. A large number of plasmids are available, such as pBR322, pACYC184, RSF1010, pRO1614, and the like. See for example, Olson et al. (1982); Bagdasarian et al. (1981), Baum et al., 1990, and U.S. Pat. Nos. 4,356,270; 4,362,817; 4,371,625, and 5,441,884, each incorporated specifically herein by reference.

The PEAMT sequence can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for enzymatic activity. If desired, unwanted or ancillary DNA sequences may be selectively removed from the recombinant bacterium by employing site-specific recombination systems, such as those described in U.S. Pat. No. 5,441,884 (specifically incorporated herein by reference).

In accordance with the present invention, nucleic acid sequences include and are not limited to DNA, including and not limited to cDNA and genomic DNA, genes; RNA, including and not limited to mRNA and tRNA; antisense sequences, PNAs (peptide nucleic acids), nucleosides, and suitable nucleic acid sequences such as those set forth herein, as well as alterations in the nucleic acid sequences including alterations, deletions, mutations, and homologs capable of expressing the PEAMT polypeptides and peptide fragments of the present invention.

As such the present invention also concerns DNA segments, that are free from total genomic DNA and that encode the novel plant-derived polypeptides disclosed herein. DNA segments encoding these peptide species may prove to encode proteins, polypeptides, subunits, functional domains, and the like of PEAMT-related or other non-related gene products. In addition these DNA segments may be synthesized entirely in vitro using methods that are well known to those of skill in the art.

As used herein, the term "DNA segment" refers to a DNA molecule that has been isolated free of total genomic DNA of a particular species. Therefore, a DNA segment encoding a PEAMT polypeptide or peptide refers to a DNA segment that contains PEAMT coding sequences yet is isolated away from, or purified free from, total genomic DNA of the species from which the DNA segment was obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified PEAMT polypeptide-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a plant PEAMT polypeptide, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where PEAMT or ΔPEAMT protein expression is concerned. The addition of terminal sequences particularly applies to nucleic acid sequences that may, for example, include various non-coding sequences flanking either of the 5' or 3' portions of the PEAMT or ΔPEAMT coding region or may include various internal sequences, ie., introns, which are known to occur within eukaryotic genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Highly preferred nucleic acid segments of the present invention comprise one or more PEAMT-encoding polynucleotide sequences of the invention, or a portion of one or more such sequences. For certain application, relatively small contiguous nucleic acid sequences are preferable, such as those which are about 14 or 15 or 16 or 17 or 18 or 19, or 20, or 30–50, 51–80, 81–100 or so nucleotides in length. Alternatively, in some embodiments, and particularly those involving preparation of recombinant vectors, transformation of suitable host cells, and preparation of transgenic plant cell, longer nucleic acid segments are preferred, particularly those that include the entire coding region of one or more PEAMT- or ΔPEAMT-encoding nucleic acid segments. As such, the preferred segments may include those that are up to about 20,000 or so nucleotides in length, or alternatively, shorter sequences such as those about 19,000, about 18,000, about 17,000, about 16,000, about 15,000, about 14,000, about 13,000, about 12,000, about 11,000, about 10,000, about 9,000, about 8,000, about 7,000, about 6,000, about 5,000, about 4,500, about 4,000, about 3,500, about 3,000, about 2,500, about 2,000, about 1,500, about 1,000, about 500, or about 200 or so base pairs in length. Of course, these numbers are not intended to be exclusionary of all possible intermediate lengths in the range of from about 20,000 to about 15 nucleotides, as all of these intermediate lengths are also contemplated to be useful, and fall within the scope of the present invention. It will be readily understood that "intermediate lengths", in these contexts, means any length between the quoted ranges, such as 14, 15, 16, 17, 18, 19, 20, etc.; 21, 22, 23, 24, 25, 26, 27, 28, 29, etc.; 30, 31, 32, 33, 34, 35, 36 . . . etc.; 40, 41, 42, 43, 44 . . . etc., 50, 51, 52, 53 . . . etc.; 60, 61, 62, 63 . . . etc., 70, 80, 90, 100, 110, 120, 130 . . . etc.; 200, 210, 220, 230, 240, 250 . . . etc.; including all integers in the entire range from about 14 to about 10,000, including those integers in the ranges 200–500; 500–1,000; 1,000–2,000; 2,000–3,000; 3,000–5,000 and the like.

In a preferred embodiment, the nucleic acid segments comprise a sequence of from about 31 to about 3500 base pairs or so in length, and comprise at least a first sequence region that encodes all, or substantially all of a plant-derived PEAMT or ΔPEAMT polypeptide.

Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.9 Methods for Making Transgenic Plants

In a further embodiment, the invention provides transgenic plant cells, transgenic plants, progeny, and seeds having stably incorporated into their genome at least a first transgene that encodes a PEAMT or ΔPEAMT polypeptide that comprises at least a 27-amino acid contiguous sequence from SEQ ID NO:2 or SEQ ID NO:4. Exemplary transgenic plants are those having stably incorporated into their genome a selected nucleic acid sequence that comprises at least a first trangene that comprises at least a 26-basepair contiguous nucleic acid sequence from SEQ ID NO:1 or SEQ ID NO:3.

The progeny or offspring of such a transgenic plant, as well as its fruit, nuts, and/or seed, progeny from such fruit, nuts, and/or seeds, as well as all fruits, nuts and/or seeds arising from the second and all subsequent generation plants derived from such a parental transgenic plant, plant tissue or transformed plant host cell also represent important aspects of the present invention.

The invention also discloses and claims host cells, both native, and genetically engineered, which express the novel PEAMT-encoding sequence to produce polypeptides having PEAMT enzymatic activity.

Methods of using such cells to produce polypeptides and peptides are also disclosed. Such methods generally involve culturing the host cell under conditions effective to produce a PEAMT polypeptide or peptide, and obtaining the polypeptide so produced from said cell.

In yet another aspect, the present invention provides methods for producing a transgenic plant that expresses a nucleic acid segment encoding the novel PEAMT polypeptides of the present invention. The process of producing transgenic plants is well known in the art. In general, the method comprises transforming a suitable host cell with one or more nucleic acid segments that contain one or more promoters operatively linked to a coding region that encodes one or more of the disclosed PEAMT proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant PEAMT polypeptide expressed in a particular transgenic cell, the invention also provides for the expression of PEAMT antisense mRNA. The use of antisense mRNA as a means of controlling or decreasing the amount of a given protein of interest in a cell is well known in the art.

Another aspect of the invention comprises a transgenic plant that expresses a gene or gene segment encoding one or more of the novel PEAMT polypeptide compositions disclosed herein. As used herein, the term "transgenic plant" is intended to refer to a plant that has stably incorporated DNA sequences, including but not limited to genes that are perhaps not normally present, DNA sequences not normally transcribed into RNA or translated into a protein ("expressed"), or any other genes or DNA sequences that one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more PEAMT-encoding transgenes, either native, synthetically modified, or mutated. In some instances, more than one transgene will be incorporated into the genome of the transformed host plant cell. Such is the case when more than one PEAMT-encoding DNA segment is incorporated into the genome of such a plant. In certain situations, it may be desirable to have one, two, three, four, or even more PEAMT proteins (either native or recombinantly-engineered) incorporated and stably expressed in the transformed transgenic plant.

A preferred selected nucleic acid sequence that may be introduced into a target host plant includes, for example, a polynucleotide that encodes a PEAMT or ΔPEAMT polypeptide, and particularly one or more of those described in SEQ ID NO:2 and SEQ ID NO:4, respectively. Highly preferred nucleic acid sequences are those obtained from PEAMT- or ΔPEAMT-expressing plants, or any of those sequences that have been genetically engineered to decrease or increase the enzymatic activity of the PEAMT or ΔPEAMT polypeptide in such a transformed host cell.

Means for transforming a plant cell and the preparation of a transgenic cell line are well known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed PEAMT and ΔPEAMT polypeptides and proteins. These DNA constructs can further include structures such as promoters, enhancers, polylinkers, or even gene sequences that have positively- or negatively-regulating activity upon the particular genes of interest as desired. The DNA segment or gene may encode either a native or modified PEAMT or ΔPEAMT polypeptide or protein, which will be expressed in the resultant recombinant cells, and/or which will impart an improved phenotype to the regenerated plant.

Such transgenic plants may be desirable for increasing the biosynthesis of oils in a monocotyledonous or dicotyledonous plant, by incorporating into such a plant, a transgenic DNA segment encoding at least a first PEAMT or ΔPEAMT polypeptide. Particularly preferred plants include grains such as safflower, canola, sunflower, tobacco, corn, wheat, rye, millet, rice, barley, and oats; legumes such as beans, peas, soybeans; tubers such as potatoes and sugar beets; fiber crops such as kapok, flax and cotton; turf and pasture grasses; ornamental plants; shrubs; trees; vegetables, berries, citrus, fruits, cacti, succulents, and other commercially-important crops including garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PEAMT- or ΔPEAMT-encoding transgene(s) stably incorporated into its genome, and such progeny plants will inherit the traits afforded by the introduction of a stable transgene in Mendelian fashion. All such transgenic plants having incorporated into their genome transgenic DNA segments encoding one or more PEAMT or ΔPEAMT polypeptides are aspects of this invention. Particularly preferred transgenes for the practice of the invention include nucleic acid segments comprising one or more nucleic acid sequences that encode a PEAMT or a ΔPEAMT polypeptide.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

Figure 2A:
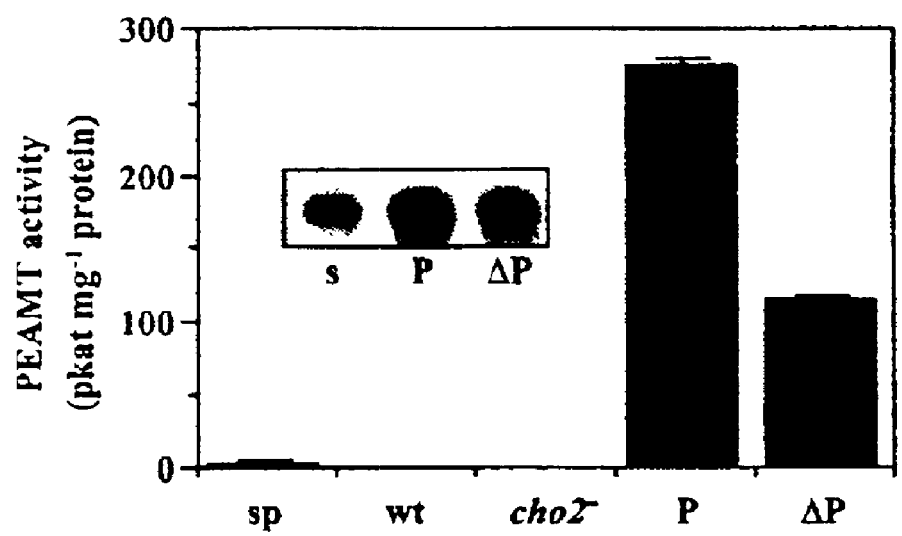

FIG. 2A illustrates expression of spinach PEAMT and ΔPEAMT cDNAs in extracts of S. pombe cho2⁻ mutant cells. Shown is PEAMT activity in desalted extracts from unsalinized spinach leaves (sp) and strains 972 ($h^{-s}$) (wt), Bx22 (cho2⁻), and Bx22 expressing PEAMT (P) or ΔPEAMT (ΔP). Assays contained 50 nmol P-EA, 44 nmol [methyl-$^{14}$C]AdoMet, and 15–710 g of protein. Data are means ±S.E. (n=2 or 3). P-MME is the principal product (>90%) formed in these assays, as shown in the inset, which is an autoradiograph of a TLC separation of a [$^{33}$P]P-MME standard (s) and the reaction product from representative assay mixtures.

Figure 2B:
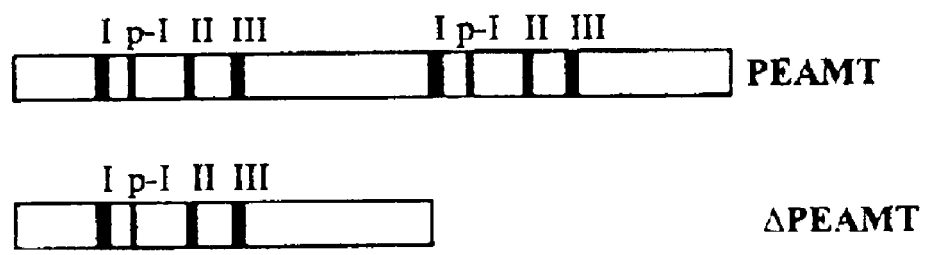

FIG. 2B shows a schematic representation of the complementing cDNAs. PEAMT is the full-length cDNA, containing two sets of the methyltransferase motifs I, post-I (p-I), II and III. ΔPEAMT is truncated after Gly-286.

Figure 3:
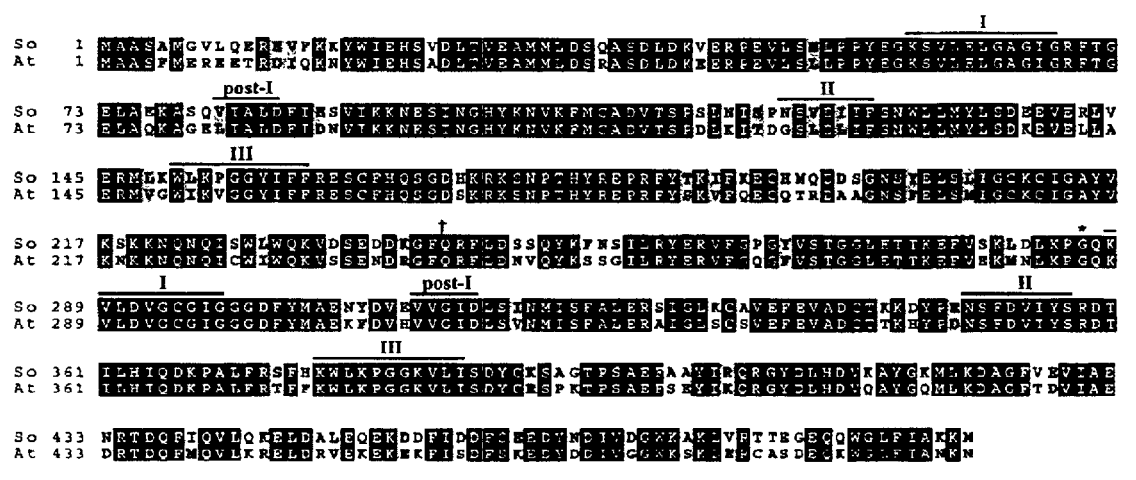

FIG. 3 illustrates alignment of the deduced amino acid sequence of the Spinacia oleracea (spinach) PEAMT (So) with an Arabidopsis homolog (At) deduced from nucleotides 65132–67885 of P1 clone MEB5 (GenBank Accession No. AB019230). The Arabidopsis genomic DNA has 13 exons and 12 introns; the identity of the region including amino acids 369494 is authenticated by alignment with an EST (GenBank Accession No. N65610). The asterisk marks the residue (Gly-286) at which ΔPEAMT is truncated.

Figure 4A:
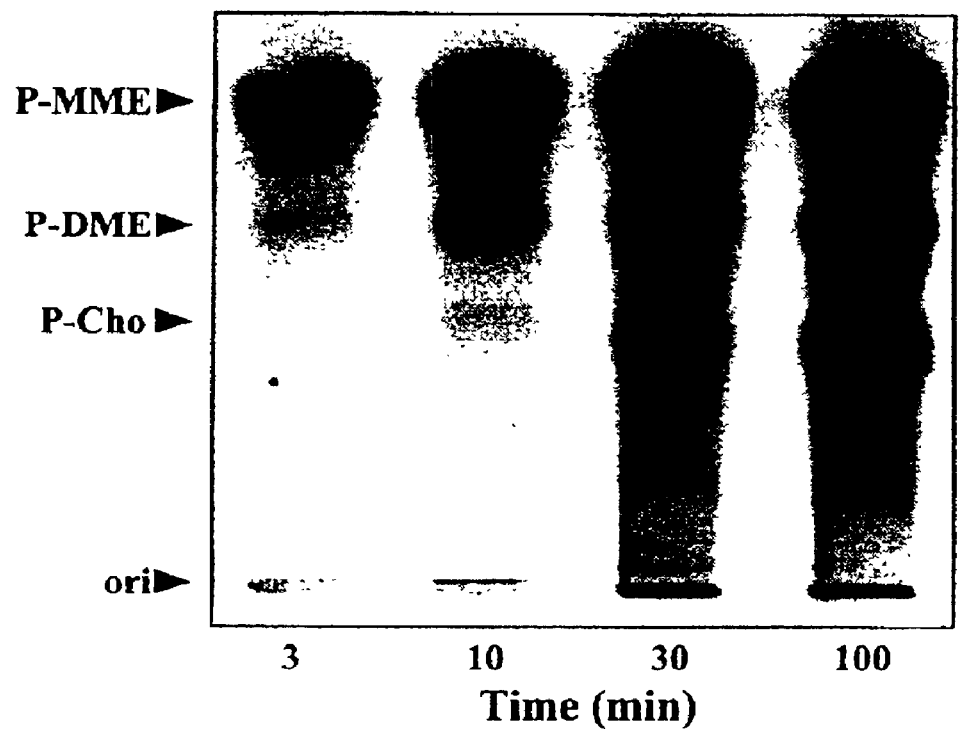

FIG. 4A illustrates evidence that PEAMT has three methyltransferase activities. Shown is an autoradiograph of a TLC separation of PEAMT reaction products. Extract (130 μg protein) from Bx22 expressing PEAMT was incubated with 2 nmol P-EA and 7 mmol (400 nCi) [methyl-$^{14}$C]AdoMet; samples were removed at intervals, stopped and de-proteinized with acetone, fractionated by ion exchange and separated in TLC system 1. The positions of P-MME, P-DME and P-Cho zones and the origin (ori) are indicated.

Figure 4B:
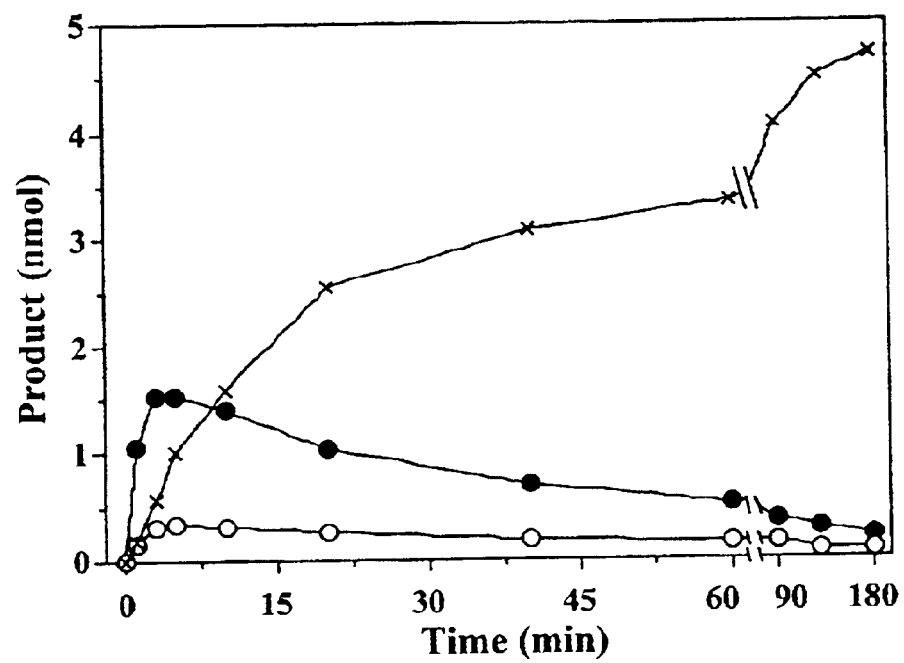

FIG. 4B shows the progress curve of the PEAMT reaction. Extract (15 μg protein) from Bx22 cells expressing PEAMT was incubated with 5 nmol P-EA and 27 nmol (400 nCi) [methyl-$^{14}$C]AdoMet. Samples were removes at the indicated times, stopped by freezing, fractionated by ion exchange and separated in TLC system 1. The P-MME, P-DME and P-Cho zones were located by autoradiography, scraped and counted. Radioactivity in P-DME and P-Cho zones was corrected for spillover from the P-MME zone. All data were adjusted for recovery from the TLC plate. , P-MME; , P-DME; X, P-Cho.

Figure 5A:
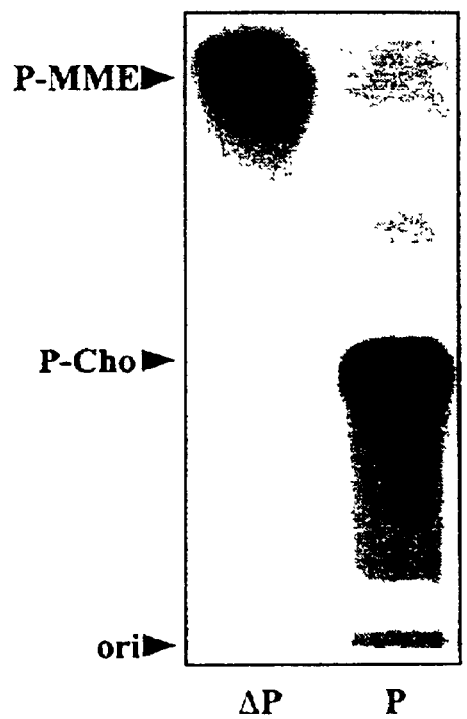

FIG. 5A illustrates evidence that PEAMT and ΔPEAMT have distinct methyltransferase activities. Shown is an autoradiograph of a TLC separation of the reaction products of wild type PEAMT (P) and the truncated enzyme ΔPEAMT (AP). Extracts (200 μg protein) from Bx22 cells expressing PEAMT or ΔPEAMT were incubated with 5 nmol P-EA and 27 nmol (100 nCi) [methyl-$^{14}$C]AdoMet for 3 hr. The positions of P-MME and P-Cho zones and the origin (ori) are indicated.

Figure 5B:
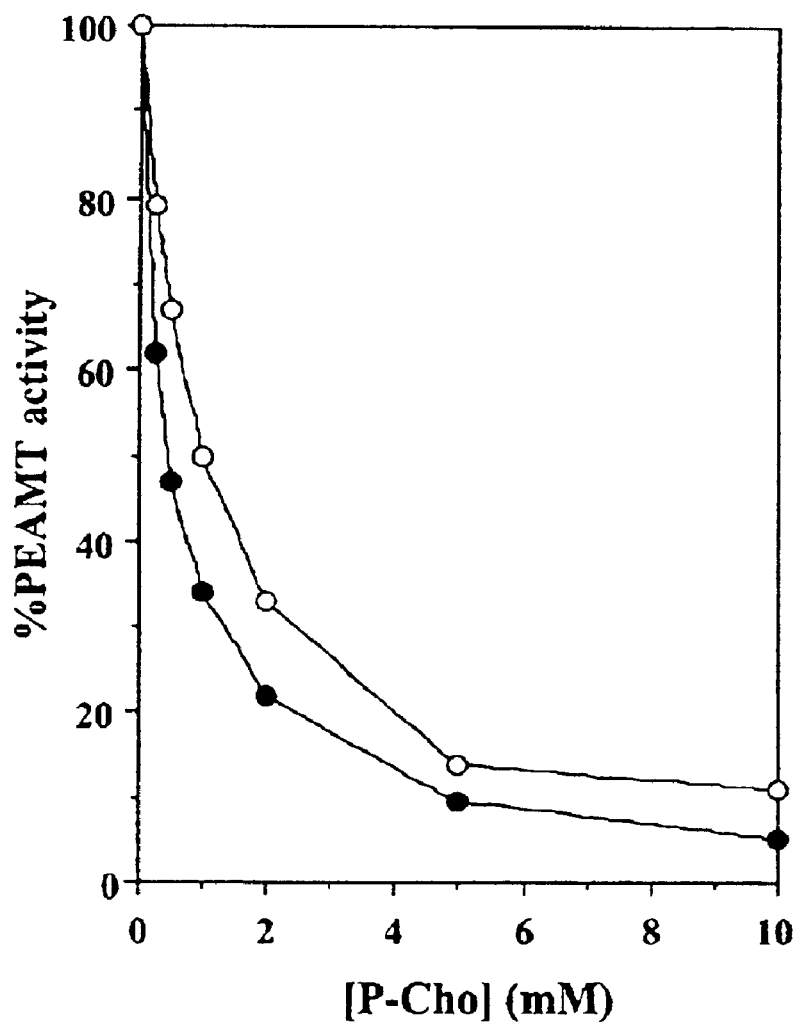

FIG. 5B illustrates that PEAMT AND ΔPEAMT enzyme activity is inhibited by P-Cho. Shown is the PEAMT activity assayed in the presence of increasing P-Cho concentration. Extracts from Bx22 cells expressing PEAMT (25 μg protein) or ΔPEAMT (50 μg protein) were incubated for 10 min with 50 nmol P-EA, 170 nmol [methyl-$^{14}$C]AdoMet and various concentrations of the disodium salt of P-Cho. Activities in the absence of P-Cho were 737±18 and 200±10 pkat mg$^{-1}$ protein for PEAMT and ΔPEAMT, respectively. Data are means of duplicates. ,PEAMT; ,ΔPEAMT.

Figure 6:
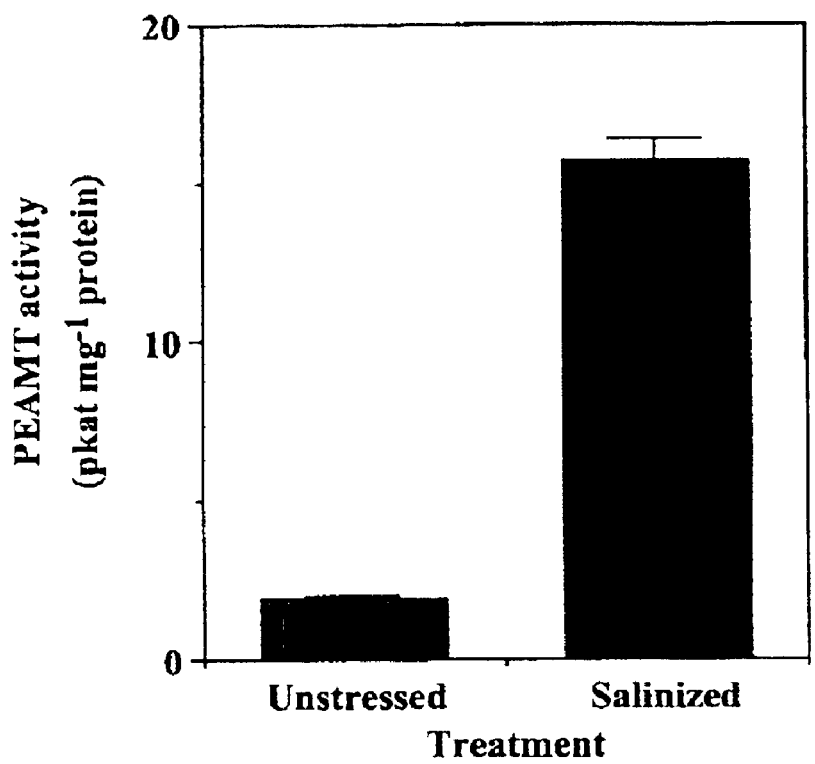

FIG. 6 illustrates the effect of salinization on PEAMT expression in spinach leaves. Shown is PEAMT activity, using assays that contained 50 nmol P-EA, 200 nmol [methyl-$^{14}$C]AdoMet and 100 μg of protein, and which were incubated for 30 min. Data are means ±S.E. (n 3).

4.0 DESCRIPTION OF ILLUSTRATIVE EMBODIMENTS

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a, polynucleotide sequence, wherein the polynucteotide sequence in the comparison window may comprise additions or deletions (i.e. gaps) compared to the reference sequence (which does not comprise additions or deletions) for optimal alignment of the two sequences. Generally, the comparison window is at least 20 contiguous nucleotides in length, and optionally can be 30, 40, 50, 60, 70, 80, 90, or 100 contiguous nucleotides, or even longer depending upon the particular analysis. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al., (1981); by the homology alignment algorithm of Needleman et al., (1970); by the search for similarity method of Pearson et al. (1988); by computerized implementations of these algorithms, including, but not limited to: CLUSTAL in the PC/Gene program by Intelligenetics (Mountain View, Calif.); GAP, BESTFIT, BLAST, FASTA, and TFASTA in the Wisconsin Genetics Software Package, Genetics Computer Group (Madison, Wis.); the CLUSTAL program is well described by Higgins et al. (1988); Higgins et al. (1989); Corpet et al. (1988); Huang et al. (1992), and Person et al. (1994); preferred computer alignment methods also include the BLASTP, BLASTN, and BLASTX algorithms (Altschul et al., 1990). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least about 70% sequence identity, preferably at least about 80%, more preferably at least about 90%, and most preferably at least about 95% to about 99%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least about 60%, more preferably at least about 70%, at least about 80%, at least about 90%, and most preferably at least about 95% to about 99%.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 M at pH 7 and the temperature is at least about 50° C., about 55° C., or even at least about 60° C., about 65° C., or at least about 70° C. or 75° C. so. However, nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least about 70% sequence identity to a reference sequence, preferably at least about 80%, more preferably at least about 85%, most preferably at least about 90% or at least about 95% to about 99% or so sequence identity to the reference sequence over a specified comparison window. Preferably, optimal alignment is conducted using the homology alignment algorithm of Needleman et al. (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The proteins of the invention may be altered in various ways including amino acid substitutions, deletions, truncations, and insertion. Methods for such manipulations are generally known in the art. For example, amino acid sequence variants of the proteins can be prepared by mutations in the DNA that encode them. Methods for mutagenesis and nucleotide sequence alterations are well known in the art (see e.g. Kunkel, 1985; Kunkel et al., 1987; U.S. Pat. No. 4,873,192; Walker and Gaastra, 1983, each of which is specifically incorporated herein by reference in its entirety).

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired PEAMT or ΔPEAMT activity. Obviously, the mutations that will be made in the DNA encoding the variant must not place the sequence out of reading frame and preferably will not create complementary regions that could produce secondary mRNA structure (see e.g., Eur. Pat. Appl. Publ. No. 75,444, specifically incorporated herein by reference in its entirety).

"Seed-specific" promoters of the invention may also include embryo-specific promoters. Such promoters may include, but are not limited to, globulin 1, cruciferin, napin, β-conglycinin, phaseolin, and the like, as well as other promoters associated with storage proteins or involved in fatty acid or lipid biosynthesis.

The polynucleotides of the invention may be provided in one or more expression cassettes or genetic constructs to facilitate introduction and stable integration into the plant genome. Such expression cassettes may comprise one or more transcriptional initiation regions linked to a coding sequence or antisense sequence of the particular PEAMT or ΔPEAMT sequence. Such an expression cassette is generally provided with a plurality of restriction sites for insertion of the sequence to be under the transcriptional regulation of the regulatory regions. The expression cassette may additionally contain one or more selectable marker genes.

The transcriptional initiation region, the promoter, may be native (i.e. analogous) or foreign (i.e. heterologous) to the plant host. Additionally, the promoter may be a synthetic sequence. By "foreign," it is intended that the transcriptional initiation region not be found in the native plant into which the transcriptional initiation region is introduced. For example, a spinach PEAMT gene would be consider a "foreign" gene if introduced into the genome of a non-spinach plant, such as corn or soybeans.

The transcriptional cassette may include in the 5' to 3' direction of transcription, a transcriptional and translational initiation region, a PEAMT or ΔPEAMT coding sequence, and a transcriptional and translational termination region functional in the particular plant species into which the construct is introduced. The termination region may be native with the transcriptional initiation region, may be native with the DNA sequence of interest, or may be derived from another source. Convenient termination regions are available from the Ti-plasmid of *A. tumefaciens* such as the octopine synthase and nopaline synthase termination regions (Guerineau et al., 1991; Proudfoot, 1991; Sanfacon et al., 1991; Mogen et al., 1990; Munroe et al., 1990; Ballas et al., 1989; Joshi et al., 1987, each of which is specifically incorporated herein by reference in its entirety).

In preparing the expression cassette, the various polynucleotide fragment(s) may be manipulated, so as to provide for the DNA sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For this purpose, in vitro mutagenesis, primer repair, restriction, annealing, resubstitutions (e.g., transitions and transversions), may be involved.

The modulation of lipid biosynthesis can be achieved in any plant of interest. Of particular interest are plants useful for human foodstuffs and domestic animal feedstock. Such plants include forage and seed crop plants, and preferably crops such as cereals and oilseed crops. Of particular interest are plants where the seed is produced in high amounts, or the seed or a seed part is edible. Seeds of interest include the oilseeds, such as from *Brassica*, cotton, soybean, safflower, canola, sunflower, coconut, palm, etc.; grain seeds such as wheat, rice, corn, etc.; other seeds including oats, pumpkin, squash, poppy, sesame, peanut, peas, beans and other legumes, cocoa, coffee, etc.; and tree nuts such as walnuts, pecans, almonds, etc. Especially preferred plants are corn, soybean, legumes, safflower, sunflower, canola, *Brassica*, wheat, rye, rice, millet, sorghum, alfalfa, and the like.

The modified plant may be grown into plants in accordance with conventional ways (McCorrnick et al., 1986). These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited into the progeny and subsequent generations of the transformed plant. Likewise, the seeds from the transformed plant or from a progeny or subsequent generation of the plant may be harvested and assayed to ensure the desired phenotype has been achieved in the progeny and the seeds from the transgenic plant and its offspring.

4.1 Transformed Host Cells and Transformation Methods

A bacterial cell, a yeast cell, or a plant cell transformed with a PEAMT-encoding gene-containing expression vector of the present invention also represents an important aspect of the present invention. Furthermore, transgenic plants and the progeny and seeds derived from such a transformed or transgenic plant are also important aspects of this invention.

Such transformed host cells are often desirable for use in the expression of the various DNA gene constructs disclosed herein. In some aspects of the invention, it is often desirable to modulate, regulate, or otherwise control the expression of the gene segments disclosed herein. Such methods are routine to those of skill in the molecular genetic arts. Typically, when increased or over-expression of a particular gene is desired, various manipulations may be employed for enhancing the expression of the messenger RNA, particularly by using an active promoter, as well as by employing sequences, which enhance the stability of the messenger RNA in the particular transformed host cell.

Typically, the initiation and translational termination region will involve stop codon(s), a terminator region, and optionally, a polyadenylation signal. In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

Where no functional replication system is present, the construct will also preferably include a sequence of at least about 40 or 50 basepairs (bp) or so, preferably at least about 90 to about 100 or so bp, and usually not more than about 500 to about 1000 or so bp of a sequence homologous with a sequence in the host. In this way, the probability of legitimate recombination is enhanced, so that the gene will be integrated into the host and stably maintained by the host. Desirably, the PEAMT- or ΔPEAMT-encoding gene-promoter construct will be in close proximity to the gene providing for complementation as well as the gene providing for the competitive advantage. Therefore, in the event that a PEAMT- or ΔPEAMT-encoding gene is lost, the resulting organism will be likely to also lose the PEAMT and ΔPEAMT gene and/or the gene providing for the competitive advantage, so that it will be unable to compete in the environment with the gene retaining the intact construct.

The PEAMT- or ΔPEAMT-encoding gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

Alternatively, the left and right T-DNA borders from the Ti plasmid may be used when integration is desired using *A. tumefaciens* vectors for plant transformation. The transformants can be isolated in accordance with conventional ways, usually employing a selection technique, which allows for selection of the desired organism as against unmodified organisms or transferring organisms, when present. The transformants then can be tested for presence of the genetic construct.

Genes or other nucleic acid segments, as disclosed herein, can be inserted into host cells using a variety of techniques that are well known in the art. Five general methods for delivering a nucleic segment into cells have been described: (1) chemical methods (Graham and VanDerEb, 1973); (2) physical methods such as microinjection (Capecchi, 1980), electroporation (U.S. Pat. No. 5,472,869; Wong and Neumann, 1982; Fromm et al., 1985), microprojectile bombardment (Wang et al., 1988; Tomes et al., 1990; Vain et al, 1993; U.S. Pat. No. 5,874,265, specifically incorporated herein by reference in its entirety), "gene gun" (Hilber et al., 1994; Yang et al., 1990); (3) viral vectors (Clapp, 1993; Danos and Heard, 1992; Eglitis and Anderson, 1988); (4) receptor-mediated mechanisms (Curiel et al., 1991; Wagner et al., 1992); and (5) bacterial-mediated delivery such as *A. tumefaciens* transformation (Smith and Hood, 1995).

For example, a large number of cloning vectors comprising a replication system in *E. coli* and a marker that permits selection of the transformed cells are available for preparation for the insertion of foreign genes into higher organisms, including plants. The vectors comprise, for example, plasmids (such as pBR322, pUC series, M13 mp series, pACYC184, etc), cosmids, phage, and/or phagemids and the like. Accordingly, the disclosed polynucleotides can be inserted into a given vector at a suitable restriction site. The resulting plasmid may be used, for example, to transform bacterial cells such as *E. coli* or *A. tumefaciens*. The bacterial cells are then cultivated in a suitable nutrient medium, harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary.

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well known to those of skill in the art, and described hereinbelow in detail. Likewise, a large number of techniques are available for inserting DNA into a plant host cell. Those techniques include transformation with T-DNA using *A. tumefaciens* or *A. rhizogenes* as transformation agent, fusion, injection, or electroporation as well as other possible methods. If *agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA.

Intermediate vectors cannot replicate themselves in *agrobacteria*. The intermediate vector can be transferred into *A. tumefaciens* by means of a helper plasmid (conjugation). Binary vectors can replicate themselves both in *E. coli* and in *agrobacteria*. They comprise a selection marker gene and a linker or polylinker that are framed by the right and left T-DNA border regions. They can be transformed directly into *agrobacteria* (Holsters et al., 1978). The *agrobacterium* used as host cell is to comprise a plasmid carrying a vir region. The vir region is necessary for the transfer of the T-DNA into the plant cell. Additional t-DNA may be contained. The bacterium so transformed is used for the transformation of plant cells. Plant explants can advantageously be cultivated with *A. tumefaciens* or *A. rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC, pRK, pBluescript, etc. and/or their derivatives. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in Eur. Pat. Appl. No. EP 120516; Hockema (1985); An et al., 1985, Herrera-Estrella et al., (1983), Bevan et al., (1983), and Klee et al., (1985).

A particularly useful Ti plasmid cassette vector for transformation of dicotyledonous plants consists of the enhanced CaMV35S promoter (EN-35S) and the 3' end including polyadenylation signals from a soybean gene encoding the α'-subunit of β-conglycinin. Between these two elements is a multilinker containing multiple restriction sites for the insertion of genes of interest.

The vector preferably contains a segment of pBR322 which provides an origin of replication in *E. coli* and a region for homologous recombination with the disarmed T-DNA in *Agrobacterium* strain ACO; the oriV region from the broad host range plasmid RK1; the streptomycin/spectinomycin resistance gene from Tn7; and a chimeric NPTII gene, containing the CaMV35S promoter and the nopaline synthase (NOS) 3'-end, which provides kanamycin resistance in transformed cells.

Optionally, the enhanced CaMV35S promoter may be replaced with the 1.5-kb mannopine synthase (MAS) promoter (Velten et al., 1984). After incorporation of a DNA construct into the vector, it is introduced into *A. tumefaciens* strain ACO that contains a disarmed Ti plasmid. Cointegrate Ti plasmid vectors are selected and subsequently may be used to transform a dicotyledonous plant.

*A. tumefaciens* ACO is a disarmed strain similar to pTiB6SE described by Fraley et al., (1985). For construction of ACO the starting *Agrobacterium* strain was the strain A208 that contains a nopaline-type Ti plasmid. The Ti plasmid was disarmed in a manner similar to that described by Fraley et al. (1985) so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to these segments and provide a region of homology for cointegrate formation.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

4.1.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by electroporation is well-known to those of skill in the art (see e.g., U.S. Pat. No. 5,324,253, specifically incorporated herein by reference in its entirety). In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells (U.S. Pat. No. 5,484,956; U.S. Pat. No. 5,886,244, each of which is specifically incorporated herein by reference in its entirety), or embryogenic callus (U.S. Pat. No. 5,405,765, each of which is specifically incorporated herein by reference in its entirety), or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be the recipient of DNA transfer by electroporation, which may be carried out at this stage, and transformed cells then identified by a suitable selection or screening protocol dependent on the nature of the newly incorporated DNA.

4.1.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 h post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust several of the bombardment parameters in small-scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.1.3 *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1988). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide-coding genes. The vectors described (Eichholtz et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods (see e.g., U.S. Pat. No. 5,610,042, specifically incorporated herein by reference in its entirety).

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e. a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two or more independently segregating added, exogenous genes. Selfing of appropriate progeny can produce plants that are homozygous for both added, exogenous genes that encode a polypeptide of interest. Backcrossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al, 1987; Marcotte et al., 1988).

Application of these systems to different plant strains depends upon the ability to regenerate that particular plant strain from protoplasts. Illustrative methods for the regeneration of cereals from protoplasts are described (Fujimura et al, 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology may also be utilized (Vasil, 1992).

Using that latter technology, DNA is carried through the cell wall and into the cytoplasm on the surface of small metal particles as described (Klein et al., 1987; Klein et al., 1988a; 1988b; McCabe et al, 1988). The metal particles penetrate through several layers of cells and thus allow the transformation of cells within tissue explants.

4.2 Expression Vectors

The present invention also provides an expression vector comprising at least one PEAMT- or ΔPEAMT-encoding gene-containing polynucleotide operably linked to an inducible promoter. Thus, in one embodiment an expression vector is an isolated and purified DNA molecule comprising a PEAMT or a ΔPEAMT coding region operably linked to a promoter that expresses the gene, which coding region is operatively linked to a transcription-terminating region, whereby the promoter drives the transcription of the coding region.

As used herein, the term "operatively linked" means that a promoter is connected to a nucleic acid region encoding functional RNA in such a way that the transcription of that functional RNA is controlled and regulated by that promoter. Means for operatively linking a promoter to a nucleic acid region encoding functional RNA are well known in the art.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive terminii or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.3 DNA Segments as Hybridization Probes and Primers

In another aspect, DNA sequence information provided by the invention allows for the preparation of relatively short DNA (or RNA) sequences having the ability to specifically hybridize to gene sequences of the selected polynucleotides disclosed herein. The ability of such nucleic acid probes to specifically hybridize to all or portions of one or more PEAMT- or ΔPEAMT-encoding genes lends them particular utility in a variety of embodiments. Most importantly, the probes may be used in a variety of assays for detecting the presence of complementary sequences in a given sample, and in the identification of new species or genera of ΔPEAMT- and PEAMT-encoding genes from a variety of host organisms.

In certain embodiments, it is advantageous to use oligonucleotide primers. The sequence of such primers is designed using a polynucleotide of the present invention for use in detecting, amplifying or mutating a defined segment of the disclosed PEAMT- and ΔPEAMT-encoding genes (e.g., SEQ ID NO:1 and SEQ ID NO:3, respectively) from a sample using PCR™ technology. Segments of related ΔPEAMT- and PEAMT-encoding genes from other species, and particularly from other related plant species may also be amplified by PCR™ using such primers.

To provide certain of the advantages in accordance with the present invention, a preferred nucleic acid sequence employed for hybridization studies or assays includes sequences that are complementary to at least about 31 to 50 or so long nucleotide stretch of a PEAMT-encoding gene sequence. A size of at least 31 nucleotides in length helps to ensure that the fragment will be of sufficient length to form a duplex molecule that is both stable and selective. Molecules having complementary sequences over stretches greater than 31 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 31 to about 40 or 50 or so nucleotides, or even longer where desired. Such fragments may be readily prepared by, for example, directly synthesizing the fragment by chemical means, by application of nucleic acid reproduction technology, such as the PCR™ technology of U.S. Pat. No. 4,683,195, and U.S. Pat. No. 4,683,202, (each specifically incorporated herein by reference in its entirety), or by excising selected DNA fragments from recombinant plasmids containing appropriate inserts and suitable restriction sites.

Of course, for some applications, for example, where one desires to prepare mutants employing a mutant primer strand hybridized to an underlying template or where one seeks to isolate ΔPEAMT- and PEAMT-encoding gene sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 25° C. to about 60° C. Naturally, these ranges would encompass hybridization conditions that employ temperatures of about 26° C., 27° C., 28° C., 29° C., 30° C., 31°

C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., or 74° C., and/or conditions that employ a salt concentration of about 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M or 0.85 M.

Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In addition to the use in directing the expression of functional RNA of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of one or more PEAMT-encoding genes will find particular utility. Longer contiguous identical or complementary sequences, e.g., those of about 20, 21, 22, 23, 24, etc., 30, 31, 32, 33, 34, etc., 40, 41, 42, 43, 44, etc., 50, 51, 52, 53, 54, etc., 100, 200, 300, 400, 500, 600, 700, 800, 900, 1000, 1100, 1300, 1500, 2000, etc. (including all intermediate lengths and up to and including full-length sequences will also be of use in certain embodiments.

While the ability of such nucleic acid probes to specifically hybridize to PEAMT-encoding gene sequences makes them ideal for use in detecting the presence of complementary sequences in a given sample, other uses are also envisioned, including the use of the sequence information for the preparation of mutant species primers, synthetic gene sequences, gene fusions, and/or primers for use in preparing other PEAMT-encoding genetic constructs.

The use of a hybridization probe of about 14 or so nucleotides in length allows the formation of a duplex molecule that is both stable and selective. Molecules having contiguous complementary sequences over stretches of about 15, 16, 17, 18, 19, 20, 21, 22, 23, 24, 25, 26, 27, 28, 29, or 30 or more contiguous bases in length are generally preferred, though, in order to increase stability and selectivity of the hybrid, and thereby improve the quality and degree of specific hybrid molecules obtained. One will generally prefer to design nucleic acid molecules having gene-complementary stretches of about 31, 32, 33, 34, 35, 36, 37, 38, 39, or 40 or more contiguous nucleotides in length where desired. When longer polynucleotides are desired, one may employ nucleic acid segments having gene-complementary stretches of about 41, 42, 43, 44, 45, 46, 47, 48, 49, or even 50, 60, 70, 80, 90, or 100 or more contiguous nucleotides in length where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,195 and U.S. Pat. No. 4,683,202 (each of which is specifically incorporated herein by reference in its entirety), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one may employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 75° C. Naturally, these ranges would encompass hybridization conditions that employ temperatures of about 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., or 74° C., and/or conditions that employ a salt concentration of about 0.03 M, 0.04 M, 0.05 M, 0.06 M, 0.07 M, 0.08 M, 0.09 M, 0.10 M, 0.11 M, 0.12 M, 0.13 M, or 0.14 M. Such selective conditions tolerate little, if any, mismatch between the probe and the template or target strand, and would be particularly suitable for isolating particular DNA segments that are highly homologous to one or more of the PEAMT sequences disclosed herein.

Detection of DNA segments via hybridization is well known to those of skill in the art, and the teachings of U.S. Pat. No. 4,965,188 and U.S. Pat. No. 5,176,995 (each of which is specifically incorporated herein by reference in its entirety) are exemplary of the methods of hybridization analyses. Teachings such as those found in the texts of Maloy et al, 1994; Segal 1976; Prokop and Bajpai, 1991; and Kuby, 1994, are also particularly relevant.

In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test nucleic acid (e.g., DNA, PNA, or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending upon, e.g., the G+C content, type of target nucleic acid, source of nucleic acid, size of the target sequence, length of the hybridization probe, etc.). Following washing of the hybridized surface so as to remove nonspecifically bound probe molecules, specific hybridization is detected, or even quantitated, by means of the label.

4.4 PEAMT and ΔPEAMT Polynucleotide Constructs

An important embodiment of the present invention concerns genetic constructs, such as plasmids, vectors, viruses, cosmids, and the like that comprise one or more of the PEAMT/ΔPEAMT-encoding polynucleotide sequences disclosed herein. Another important embodiment concerns genetic constructs that comprise one or more portions of a PEAMT- or ΔPEAMT-encoding polynucleotide or one or more regulatory regions of a PEAMT/ΔPEAMT-encoding polynucleotide sequence. Particularly important genetic constructs include those used for the preparation of oligonucleotide probes, polynucleotide primers, recombinant proteins, peptides, or peptide epitopes, and those used for sequencing PEAMT/ΔPEAMT-encoding gene sequences and homologous polynucleotides. Other important genetic constructs include transformation vectors, viruses and the like used for the introduction of the disclosed gene sequences into a host cell, plant tissue, or plant for the preparation of transgenic plants or transformed host cells that express the PEAMT/ΔPEAMT polypeptide when cultured under appropriate conditions.

A variety of genetic compositions may be used for preparation and delivery of the disclosed PEAMT/ΔPEAMT genetic constructs to selected recipient host cells, and particularly to selected plant host cells or tissues to ultimately produce transformed plants and plant cell lines in accordance with the present invention. For example, polynucleotides in the form of vectors and plasmids, or linear nucleic acid fragments, in some instances containing only the particular polynucleotide to be expressed in the cell, tissue or animal, and the like, may be employed.

Vectors, plasmids, phagemids, cosmids, viral vectors, shuttle vectors, baculovirus vectors, BACs (bacterial artificial chromosomes), PACs (plant artificial chromosomes), YACs (yeast artificial chromosomes) and DNA segments for use in transforming cells with a nucleic acid construct of interest, are well known to those of skill in the microbiological and plant molecular biology arts. Typically such constructs generally comprise at least one promoter or other regulatory region that is operably linked to at least one or more of the novel polynucleotides disclosed herein. These polynucleotide constructs may contain a cDNA, or one or more genes which one desires to introduce into a particular cell, cell line, tissue, or other suitable organism. Such polynucleotide constructs may also optionally include one or more structures such as inducible, constitutive, or tissue-specific promoters, one or more enhancers or enhancer elements, one or more polylinkers or multiple cloning sites, or one or more regulatory sequences as may be desired. The polynucleotide segment or gene chosen for cellular introduction may encode the entire PEAMT protein such that the protein may be expressed in the resultant recombinant cells, or, alternatively, the nucleic acid constructs may contain portions of the coding region, or a PEAMT gene regulatory region alone or in combination with other gene sequences, or may even comprise one or more antisense constructs, or ribozyme-encoding regions.

4.5 Methods for Preparing Mutagenized Polynucleotides

In certain circumstances, it may be desirable to modify or alter one or more nucleotides in one or more of the sequences disclosed herein for the purpose of altering or changing the transcriptional activity or other property of the sequence region. In general, the means and methods for mutagenizing a polynucleotide are well known to those of skill in the art. Modifications to such polynucleotides may be made by random, or site-specific mutagenesis procedures. The selected polynucleotide may be modified by altering its structure through the addition or deletion of one or more nucleotides within the sequence, or may be modified by the addition of a cloning site, a polylinkers region, or by the preparation of a gene fusion or a protein fusion encoding polynucleotide. Means for preparing mutagenized polynucleotides are exemplified in a number of U.S. patents and in the scientific literature. For example, U.S. Pat. No. 6,023,013 (specifically incorporated herein by reference in its entirety) provides a variety of methods for preparing mutagenized polynucleotides.

4.6 Expression of Transgenes in Plants

In many instances, the level of transcription of a particular transgene in a given host cell is not always indicative of the amount of protein being produced in the transformed host cell. This is often due to post-transcriptional processes, such as splicing, polyadenylation, appropriate translation initiation, and RNA stability that affect the ability of a transcript to produce protein. Such factors may also affect the stability and amount of mRNA produced from the given transgene. As such, it is often desirable to alter the post-translational events through particular molecular biology techniques. The inventors contemplate that in certain instances it may be desirable to alter the transcription and/or expression of the PEAMT/ΔPEAMT-encoding gene constructs of the present invention to increase, decrease, or otherwise regulate or control these constructs in particular host cells and/or transgenic plants.

4.6.1 Efficient Initiation of Protein Translation

The 5'-untranslated leader (5'-UTL) sequence of eukaryotic mRNA plays a major role in translational efficiency. Many early chimeric transgenes using a viral promoter used an arbitrary length of viral sequence after the transcription initiation site and fused this to the AUG of the coding region. More recently studies have shown that the 5'-UTL sequence and the sequences directly surrounding the AUG can have a large effect in translational efficiency in host cells and particularly certain plant species and that this effect can be different depending on the particular cells or tissues in which the message is expressed.

In most eukaryotic mRNAs, the point of translational initiation occurs at the AUG codon closest to the 5' cap of the transcript. Comparison of plant mRNA sequences and site directed mutagenesis experiments have demonstrated the existence of a consensus sequence surrounding the initiation codon in plants (Joshi, 1987; Lutcke et al., 1987). However, consensus sequences will be apparent amongst individual plant species. For example, a compilation of sequences surrounding the initiation codon from 85 maize genes yields a consensus of 5'-(C/G)AUGGCG-3' (Luehrsen et al., 1994). In tobacco protoplasts, transgenes encoding β-glucuronidase (GUS) and bacterial chitinase showed a 4-fold and an eight-fold increase in expression, respectively, when the native sequences of these genes were changed to encode 5'-ACCAUGG-3' (Gallie et al., 1987b; Jones et al., 1988).

When producing chimeric transgenes (i.e. transgenes comprising DNA segments from different sources operably linked together), often the 5'-UTL of plant viruses is used.

The alfalfa mosaic virus (AMV) coat protein and brome mosaic virus (BMV) coat protein 5'-UTLs have been shown to enhance mRNA translation 8-fold in electroporated tobacco protoplasts (Gallie et al., 1987a; 1987b). A 67-nucleotide derivative (Ω) of the 5'-UTL of tobacco mosaic virus RNA (TMV) fused to the chloramphenicol acetyltransferase (CAT) gene and GUS gene has been shown to enhance translation of reporter genes in vitro (Gallie et al., 1987a; 1987b; Sleat et al., 1987; Sleat et al., 1988). Electroporation of tobacco mesophyll protoplasts with transcripts containing the TMV leader fused to reporter genes CAT, GUS, and LUC produced a 33-, 21-, and 36-fold level of enhancement, respectively (Gallie et al., 1987a; 1987b; Gallie et al, 1991). Also in tobacco, an 83-nt 5'-UTL of potato virus X RNA was shown to enhance expression of the neomycin phosphotransferese II (NptII) 4-fold (Poogin and Skryabin, 1992).

The effect of a 5'-UTL may be different depending on the plant, particularly between dicots and monocots. The TMV 5'-UTL has been shown to be more effective in tobacco protoplasts (Gallie et al., 1989) than in maize protoplasts (Gallie and Young, 1994). Also, the 5'-UTLs from TMV-Ω (Gallie et al., 1988), AMV coat (Gehrke et al., 1983; Jobling and Gehrke, 1987), TMV-coat (Goelet et al., 1982), and BMV-coat (French et al., 1986) worked poorly in maize and inhibited expression of a luciferase gene in maize relative to its native leader (Koziel et al., 1996). However, the 5'-UTLs from the cauliflower mosaic virus (CaMV) 35S transcript and the maize genes glutelin (Boronat et al, 1986), PEP-carboxylase (Hudspeth and Grula, 1989) and ribulose biphosphate carboxylase showed a considerable increase in expression of the luciferase gene in maize relative to its native leader (Koziel et al., 1996).

These 5'-UTLs had different effects in tobacco. In contrast to maize, the TMV Ω 5'-UTL and the AMV coat protein 5'-UTL enhanced expression in tobacco, whereas the glutelin, maize PEP-carboxylase and maize ribulose-1,5-bisphosphate carboxylase 5'-UTLs did not show enhancement relative to the native luciferase 5'-UTL (Koziel et al., 1996). Only the CaMV 35S 5'-UTL region enhanced luciferase expression in both maize and tobacco (Koziel et al, 1996). Furthermore, the TMV and BMV coat protein 5'-UTLs were inhibitory in both maize and tobacco protoplasts (Koziel et al, 1996).

4.6.2 Use of Introns to Increase Expression

Including one or more introns in the transcribed portion of a gene has been found to increase heterologous gene expression in a variety of plant systems (Callis et al., 1987; Maas et al., 1991; Mascerenhas et al., 1990; McElroy et al., 1990; Vasil et al., 1989), although not all introns produce a stimulatory effect and the degree of stimulation varies. The enhancing effect of introns appears to be more apparent in monocots than in dicots. Tanaka et al. (1990) has shown that use of the catalase intron 1 isolated from castor beans increases gene expression in rice. Likewise, the first intron of the alcohol dehydrogenase 1 (Adh1) has been shown to increase expression of a genomic clone of Adh1 comprising the endogenous promoter in transformed maize cells (Callis et al., 1987; Dennis et al., 1984). Other introns that are also able to increase expression of transgenes which contain them include introns 2 and 6 of Adh1 (Luehrsen and Walbot, 1991), the catalase intron (Tanaka et al., 1990), intron 1 of the maize bronze 1 gene (Callis et al., 1987), the maize sucrose synthase intron 1 (Vasil et al., 1989), intron 3 of the rice actin gene (Luehrsen and Walbot, 1991), rice actin intron 1 (McElroy et al., 1990), and the heat shock protein HSP70 (U.S. Pat. No. 5,859,347, specifically incorporated herein by reference in its entirety). Similar results may also be obtained using sequences from certain exons, for example, the maize ubiquitin exon 1 (Christensen et al., 1992).

Generally, to achieve optimal expression, the selected intron(s) should be present in the selected 5' transcriptional unit in the correct orientation with respect to the splice junction sequences (Callis et al., 1987; Maas et al., 1991; Mascerenhas et al., 1990; Oard et al., 1989; Tanaka et al., 1990; Vasil et al., 1989). Intron 9 of Adh1 has been shown to increase expression of a heterologous gene when placed 3' (or downstream of) the gene of interest (Callis et al., 1987).

4.6.3 Use of Synthetic Genes to Increase Gene Expression

When introducing a prokaryotic gene into a eukaryotic host, or when expressing a eukaryotic gene in a non-native host, the sequence of the gene must often be altered or modified to allow efficient translation of the transcript(s) derived from the gene. Significant experience in using synthetic genes to increase expression of a desired protein has been achieved in the expression of B. thuringiensis-derived genes in plants. Native B. thuringiensis genes are expressed only at low levels in dicots and not at all in monocots (Koziel et al., 1996). Codon usage in the native genes is considerably different from that found in typical plant genes, which have a higher G+C content. Strategies to increase expression of these genes in plants generally alter the overall G+C content of the genes. For example, synthetic *B. thuringiensis* δ-endotoxin encoding genes have resulted in significant improvements in expression of the δ-endotoxins in various crops including cotton (Perlak et al., 1990; Wilson et al., 1992), tomato (Perlak et al., 1991), potato (Perlak et al., 1993), rice (Cheng et al., 1998), and maize (Koziel et al., 1993).

In a similar fashion the inventors contemplate that the PEAMT/ΔPEAMT-encoding sequences of the present invention, may in certain circumstances, be altered to increase or decrease the expression of the genes in particular eukaryotic host cells and/or transgenic plants that comprise such constructs. Using molecular biology techniques that are well known to those of skill in the art, one may alter the coding or non-coding sequences of the particular PEAMT/ΔPEAMT gene(s) to optimize or facilitate its expression in transformed plant cells at suitable levels.

4.6.4 Chloroplast Sequestering and Targeting

Methods of targeting proteins to the chloroplast have been developed utilizing the pea chloroplast transit peptide, to target the enzymes of the polyhydroxybutyrate synthesis pathway to the chloroplast (Nawrath et al., 1994). Also, this technique negated the necessity of modification of the coding region other than to add an appropriate targeting sequence.

U.S. Pat. No. 5,576,198 (specifically incorporated herein by reference in its entirety) discloses compositions and methods useful for genetic engineering of plant cells to provide a method of controlling the timing or tissue pattern of expression of foreign DNA sequences inserted into the plant plastid genome. Constructs include those for nuclear transformation that provide for expression of a viral single subunit RNA polymerase in plant tissues, and targeting of the expressed polymerase protein into plant cell plastids. Also included are plastid expression constructs comprising a viral gene promoter region which is specific to the RNA polymerase expressed from the nuclear expression constructs described above and a heterologous gene of interest to be expressed in the transformed plastid cells.

4.6.5 Effects of 3' Regions on Transgene Expression

The 3'-end regions of transgenes have been found to have a large effect on transgene expression in plants (Ingelbrecht et al., 1989). In this study, different 3' ends were operably linked to the neomycin phosphotransferase II (NptII) reporter gene and expressed in transgenic tobacco. The different 3' ends used were obtained from the octopine synthase gene, the 2S seed protein from *Arabidopsis*, the small subunit of rbcS from *Arabidopsis*, extension form carrot, and chalcone synthase from *Antirrhinum*. In stable tobacco transformants, there was about a 60-fold difference between the best-expressing construct (small subunit rbcS 3' end) and the lowest expressing construct (chalcone synthase 3' end).

TABLE 1

PLANT PROMOTERS

| Promoter | Reference[a] |
|---|---|
| Viral | |
| Figwort Mosaic Virus (FMV) | U.S. Pat. No. 5,378,619 |
| Cauliflower Mosaic Virus (CaMV) | U.S. Pat. No. 5,530,196 |
| | U.S. Pat. No. 5,097,025 |
| | U.S. Pat. No. 5,110,732 |
| Plant | |
| Elongation Factor | U.S. Pat. No. 5,177,011 |
| Tomato Polygalacturonase | U.S. Pat. No. 5,442,052 |
| *Arabidopsis* Histone H4 | U.S. Pat. No. 5,491,288 |
| Phaseolin | U.S. Pat. No. 5,504,200 |
| Group 2 | U.S. Pat. No. 5,608,144 |
| Ubiquitin | U.S. Pat. No. 5,614,399 |
| P119 | U.S. Pat. No. 5,633,440 |
| α-amylase | U.S. Pat. No. 5,712,112 |
| Wheat starch branching enzyme | U.S. Pat. No. 5,866,793 |
| Osmotin | U.S. Pat. No. 5,874,626 |
| Viral enhancer/Plant promoter | |
| CaMV 35S enhancer/mannopine synthase promoter | U.S. Pat. No. 5,106,739 |

[a]Each reference is specifically incorporated herein by reference in its entirety.

TABLE 2

TISSUE SPECIFIC PLANT PROMOTERS

| Tissue Specific Promoter | Tissue(s) | Reference[a] |
|---|---|---|
| Blec | Epidermis | U.S. Pat. No. 5,646,333 |
| Malate synthase | Seeds; seedlings | U.S. Pat. No. 5,689,040 |
| Isocitrate lyase | Seeds; seedlings | U.S. Pat. No. 5,689,040 |
| Patatin | Tuber | U.S. Pat. No. 5,436,393 |
| ZRP2 | Root | U.S. Pat. No. 5,633,363 |
| ZRP2(2.0) | Root | U.S. Pat. No. 5,633,363 |
| ZRP2(1.0) | Root | U.S. Pat. No. 5,633,363 |
| RB7 | Root | U.S. Pat. No. 5,459,252 |
| | Root | U.S. Pat. No. 5,401,836 |
| | Fruit | U.S. Pat. No. 4,943,674 |
| | Meristem | U.S. Pat. No. 5,589,583 |
| | Guard cell | U.S. Pat. No. 5,538,879 |
| | Stamen | U.S. Pat. No. 5,589,610 |
| SodA1 | Pollen; middle layer; stomium of anthers | Van Camp et al., 1996 |
| SodA2 | Vascular bundles; stomata; axillary buds; pericycle; stomium; pollen | Van Camp et al., 1996 |
| CHS15 | Flowers; root tips | Faktor et al., 1996 |
| Psam-1 | Phloem tissue; cortex; root tips | Vander et al., 1996 |
| ACT11 | Elongating tissues and organs; pollen; ovules | Huang et al., 1997 |
| ZmGBS | Pollen; endosperm | Russell and Fromm, 1997 |
| zmZ27 | Endosperm | Russell and Fromm, 1997 |
| OsAGP | Endosperm | Russell and Fromm, 1997 |
| osGT1 | Endosperm | Russell and Fromm, 1997 |
| RolC | Phloem tissue; bundle sheath; vascular parenchyma | Graham et al., 1997 |
| Sh | Phloem tissue | Graham et al., 1997 |
| CMd | Endosperm | Grosset et al., 1997 |
| Bnm1 | Pollen | Treacy et al., 1997 |
| rice tungro bacilliform virus | Phloem | Yin et al., 1997a; 1997b |
| S2-RNase | Pollen | Ficker et al., 1998 |
| LeB4 | Seeds | Baumlein et al., 1991 |
| gf-2.8 | Seeds; seedlings | Berna and Bernier, 1997 |

[a]Each reference is specifically incorporated herein by reference in its entirety.

The ability to express genes in a tissue specific manner in plants has led to the production of male and female sterile plants. Generally, the production of male sterile plants involves the use of anther-specific promoters operably linked to heterologous genes that disrupt pollen formation (U.S. Pat. No. 5,689,051; U.S. Pat. No. 5,689,049; and U.S. Pat. No. 5,659,124, each of which is specifically incorporated herein by reference in its entirety). U.S. Pat. No. 5,633,441 (specifically incorporated herein by reference in its entirety) discloses a method of producing plants with female genetic sterility. The method comprises the use of style-cell, stigma-cell, or style- and stigma-cell specific promoters that express polypeptides that, when produced in the cells of the plant kill or significantly disturbs the metabolism, functioning or development of the cells.

TABLE 3

INDUCIBLE PLANT PROMOTERS

| Promoter | Reference[a] |
|---|---|
| Heat shock promoter | U.S. Pat. No. 5,447,858 |
| Em | U.S. Pat. No. 5,139,954 |
| Adh1 | Kyozuka et al., 1991 |
| HMG2 | U.S. Pat. No. 5,689,056 |
| Cinnamyl alcohol dehydrogenase | U.S. Pat. No. 5,633,439 |
| Asparagine synthase | U.S. Pat. No. 5,595,896 |
| GST-II-27 | U.S. Pat. No. 5,589,614 |

[a]Each reference is specifically incorporated herein by reference in its entirety.

4.7 Gene Expression in Plants

Although great progress has been made in recent years with respect to preparation of transgenic plants that express PEAMT/ΔPEAMT-polypeptides and DNA binding proteins such as the lac operator, the results of expressing heterologous genes in particular plant species are often disappointing. Unlike microbial genetics, little was known by early plant geneticists about the factors that affected heterologous expression of foreign genes in plants. In recent years, however, several potential factors have been implicated as responsible in varying degrees for the level of protein expression from a particular coding sequence. For example, scientists now know that maintaining a significant level of a particular mRNA in the cell is indeed a critical factor. Unfortunately, the causes for low steady state levels of mRNA encoding foreign proteins are many. First, full length RNA synthesis may not occur at a high frequency. This could, for example, be caused by the premature termination of RNA during transcription or due to unexpected mRNA processing during transcription. Second, full length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half-lives (which are determined by their primary or secondary sequence) insufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure. It is likely that structure per se or particular structural features also have a role in determining RNA stability.

To overcome these limitations in heterologous gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so is by alteration of the native gene to remove sequences or motifs that decrease expression in a particular plant species. The process of engineering a coding sequence for optimal expression in plants is often referred to as "optimizing" a DNA sequence.

The present invention provides a method for preparing PEAMT- and ΔPEAMT-encoding genes that express their polypeptide product at sufficiently high levels in a heterologous transformed plant, so as to alter lipid content or alter lipid biosynthesis in the transformed plant.

4.8 Synthetic Oligonucleotides for Mutagenesis

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 5 below) so as to avoid codons which are rarely found in plant genomes, and efforts should be made to select codons to preferably adjust the G+C content to about 50%.

TABLE 5

PREFERRED CODON USAGE IN PLANTS

| Amino Acid | Codon | % Usage in Plants |
|---|---|---|
| ARG | CGA | 7 |
|  | CGC | 11 |
|  | CGG | 5 |
|  | CGU | 25 |
|  | AGA | 29 |
|  | AGG | 23 |
| LEU | CUA | 8 |
|  | CUC | 20 |
|  | CUG | 10 |
|  | CUU | 28 |
|  | UUA | 5 |
|  | UUG | 30 |
| SER | UCA | 14 |
|  | UCC | 26 |
|  | UCG | 3 |
|  | UCU | 21 |
|  | AGC | 21 |
|  | AGU | 15 |
| THR | ACA | 21 |
|  | ACC | 41 |
|  | ACG | 7 |
|  | ACU | 31 |
| PRO | CCA | 45 |
|  | CCC | 19 |
|  | CCG | 9 |
|  | CCU | 26 |
| ALA | GCA | 23 |
|  | GCC | 32 |
|  | GCG | 3 |
|  | GCU | 41 |
| GLY | GGA | 32 |
|  | GGC | 20 |
|  | GGG | 11 |
|  | GGU | 37 |
| ILE | AUA | 12 |
|  | AUC | 45 |
|  | AUU | 43 |
| VAL | GUA | 9 |
|  | GUC | 20 |
|  | GUG | 28 |
|  | GUU | 43 |
| LYS | AAA | 36 |
|  | AAG | 64 |
| ASN | AAC | 72 |
|  | AAU | 28 |
| GLN | CAA | 64 |
|  | CAG | 36 |
| HIS | CAC | 65 |
|  | CAU | 35 |
| GLU | GAA | 48 |
|  | GAG | 52 |
| ASP | GAC | 48 |
|  | GAU | 52 |
| TYR | UAC | 68 |
|  | UAU | 32 |
| CYS | UGC | 78 |
|  | UGU | 22 |
| PHE | UUC | 56 |
|  | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided.

Codons are selected avoiding the TA and CG doublets in codons whenever possible. Codon usage can be normalized against a plant preferred codon usage table (such as Table 5) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

4.9 Optimized Gene Constructs

The expression of a plant gene that exists in double-stranded DNA form involves transcription of messenger RNA (mRNA) from one strand of the DNA by RNA polymerase enzyme, and the subsequent processing of the mRNA primary transcript inside the nucleus. This processing may involve a 3' non-translated region that adds polyadenylated nucleotides to the 3' end of the RNA, or may also involve removal of introns and 5' capping. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters that are active in plant cells have been described in the literature. These include the nopaline synthase (NOS) and octopine synthase (OCS) promoters (which are carried on tumor-inducing plasmids of *A. tumefaciens*), the Cauliflower Mosaic Virus (CaMV) 19S and 35S promoters, the light-inducible promoter from the small subunit of ribulose bis-phosphate carboxylase (ssRUBISCO, a very abundant plant polypeptide) and the mannopine synthase (MAS) promoter (Velten et al., 1984 and Velten and Schell, 1985). All of these promoters have been used to create various types of DNA constructs that have been expressed in plants (see e.g., Int. Pat. Appl. Publ. No. WO 84/02913).

Promoters that are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of protein.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from RNAs, suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak (1984).

The DNA constructs of the present invention may also contain one or more modified or fully synthetic structural coding sequences which have been changed to enhance the performance of the gene in a particular species of plant. The structural genes of the present invention may optionally encode a fusion protein comprising an amino-terminal chloroplast transit peptide or secretory signal sequence.

The DNA construct also contains a 3' non-translated region. The 3' non-translated regions contain a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes like the soybean storage protein (7S) genes and the small subunit of the RuBP carboxylase (E9) gene.

4.10 Methods for Altering PEAMT Activity in Transgenic Plants

By transforming a suitable host cell, such as a plant cell, with a recombinant PEAMT/ΔPEAMT-encoding polynucleotide segment, the expression of the PEAMT/ΔPEAMT-encoding polynucleotide under the control of an inducible promoter can result in the formation of transgenic plants in which the alteration of PEAMT/ΔPEAMT activity and subsequent modulation of lipid content may be achieved.

By way of example, one may utilize an expression vector containing a coding region for a PEAMT or ΔPEAMT polynucleotide and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the encoded polypeptide.

The formation of transgenic plants may also be accomplished using other methods of cell transformation that are known in the art such as *Agrobacterium*-mediated DNA transfer (Fraley et al., 1983). Alternatively, DNA can be introduced into plants by direct DNA transfer into pollen (U.S. Pat. No. 5,629,183; Zhou et al, 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

Methods for the regeneration, development, and cultivation of plants from single plant protoplast transformants or from various transformed explants are well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

Such plants can form germ cells and transmit the transformed trait(s) to progeny plants. Likewise, transgenic plants can be grown in the normal manner and crossed with plants that have the same transformed hereditary factors or other hereditary factors. The resulting hybrid individuals have the corresponding phenotypic properties. A transgenic plant of this invention thus has an increased amount of a coding region that encodes the PEAMT or ΔPEAMT polypeptide of interest. A preferred transgenic plant is an independent segregant and can transmit that gene and its activity to its progeny. A more preferred transgenic plant is homozygous for that gene, and transmits that gene to each of its offspring on sexual mating.

Seed from a transgenic plant may be grown in the field or greenhouse, and resulting sexually mature transgenic plants are self-pollinated to generate true breeding plants. The progeny from these plants become true breeding lines that are evaluated for, by way of example, increased lipid biosynthesis, preferably in the field, under a range of environmental conditions. The inventors contemplate that the present invention will find particular utility in the creation of transgenic plants of commercial interest including various grains, grasses, fibers, tubers, legumes, ornamental plants, cacti, succulents, fruits, berries, and vegetables, as well as a number of nut- and fruit-bearing trees and plants.

4.12 Plant Cells and Transgenic Plants Expressing PEAMT

In one embodiment, the invention provides a transgenic plant having incorporated into its genome a transgene that encodes a PEAMT or ΔPEAMT polypeptide. A further aspect of the invention is a transgenic plant having incorporated into its genome a transgene that encodes such a polypeptide. Other embodiments of the invention also concern the progeny of such a transgenic plant, as well as its seed, the progeny from such seeds, and seeds arising from the second and subsequent generation plants derived from such a transgenic plant.

The invention also discloses and claims host cells, both native, and genetically engineered, which express one or more genes encoding all or substantially all of a PEAMT polypeptide to produce the encoded polypeptide(s) in a suitably transformed host cell, and in particular, in a transformed plant cell.

In yet another aspect, the present invention provides methods for producing a transgenic plant that expresses such a nucleic acid segment. The process of producing transgenic plants is well known in the art. In general, the method comprises transforming a suitable host cell with one or more DNA segments that contain a promoter operatively linked to a coding region that encodes one or more PEAMT polypeptides. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of an antisense oligonucleotide or other nucleic acid sequences that are complementary to the mRNA that encodes the expressed polypeptide. The use of antisense mRNA as a means of controlling or decreasing the amount of a given protein of interest in a cell is well known in the art.

As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more transgenes, either native, synthetically modified, or mutated. In some instances, more than one transgene will be incorporated into the genome of the transformed host plant cell. Such is the case when more than one DNA segment is incorporated into the genome of such a plant. In certain situations, it may be desirable to have one, two, three, four, or even more PEAMT proteins (either native or recombinantly-engineered) incorporated and stably expressed in the transformed transgenic plant.

A preferred gene that may be introduced includes, for example, a DNA sequence from a plant that encodes a PEAMT or a ΔPEAMT polypeptide, and particularly one or more of those described in SEQ ID NO:2 or SEQ ID NO:4.

Means for transforming a plant cell and the preparation of a transgenic cell line are well known in the art, and are discussed herein. Vectors, plasmids, cosmids, bacterial artificial chromosomes (BACs), plant artificial chromosomes (PACs), yeast artificial chromosomes (YACs), and DNA segments for use in transforming such cells will, of course, generally comprise either the operons, genes, or gene-derived sequences of the present invention, either native, or synthetically-derived, and particularly those encoding the disclosed PEAMT polypeptides. These nucleic acid constructs can further include structures such as promoters, enhancers, polylinkers, or even gene sequences that have positively- or negatively-regulating activity upon the particular genes of interest as desired. The nucleic acid segment or gene may encode either a native or modified protein, which will be expressed in the resultant recombinant cells, and/or which will impart an improved phenotype to the regenerated plant.

Such transgenic plants may be desirable for modulating lipid biosynthesis in a population of monocotyledonous or dicotyledonous plants. Particularly preferred plants include grains such as corn, wheat, rye, rice, barley, and oats; legumes such as beans, soybeans; tubers such as potatoes; fiber crops such as flax and cotton; turf and pasture grasses; ornamental plants; shrubs; trees; vegetables; berries; citrus crops, including oranges, tangerines, grapefruit, limes, lemons, and the like; fruits, cacti, succulents, and other commercially-important crops including greenhouse, garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PEAMT-encoding transgene(s) stably incorporated into its genome, and such progeny plants will inherit the traits afforded by the introduction of a stable transgene in Mendelian fashion. All such transgenic plants having incorporated into their genome transgenic DNA segments encoding one or more PEAMT polypeptides are aspects of this invention.

4.13 Isolating Homologous Gene and Gene Fragments Encoding PEAMT

The polynucleotide sequences of the subject invention include not only full-length sequences but also fragments of these sequences, (including e.g., fusion proteins), which retain the PEAMT or ΔPEAMT enzymatic activity of the sequences specifically exemplified herein in SEQ ID NO:2 and SEQ ID NO:4, respectively.

It should be apparent to a person skilled in this art that the various genetic constructs encoding PEAMT/ΔPEAMT polypeptides can be identified and obtained through several means. The PEAMT/ΔPEAMT-encoding genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes or gene fragments that encode biologically active polypeptides may be obtained using a variety of other restriction enzymes. Proteases may be used to directly obtain active fragments of these constructs.

Equivalent polypeptides and/or polynucleotides encoding these equivalent polypeptides can also be isolated from DNA libraries using the teachings provided herein. For example, antibodies to the polypeptides disclosed and claimed herein can be used to identify and isolate other similar or related polypeptides from a mixture of proteins. These antibodies can then be used to specifically identify equivalent polypeptides possessing the desired characteristics by a variety of methodologies including, e.g., immunoprecipitation, enzyme linked immunoassay (ELISA), and/or Western blotting.

A further method for identifying the polypeptides and polynucleotides of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying complementary genes of the subject invention.

The nucleotide segments that are used as probes according to the invention may be synthesized by use of nucleic acid synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{131}I$, $^{35}S$, $^{14}C$, $^{3}H$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest Mutations, insertions, and deletions can be produced in a given polynucleotide sequence in many ways, by methods currently known to an ordinarily skilled artisan, and perhaps by other methods which may become known in the future.

The potential variations in the probes listed are due, in part, to the redundancy of the genetic code. Because of the redundancy of the genetic code, i.e. more than one coding nucleotide triplet (codon) can be used for most of the amino acids used to make proteins. Therefore different nucleotide sequences can code for a particular amino acid. Thus, the amino acid sequences of the disclosed polypeptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein that do not alter the protein secondary structure, or if the structure is altered, the biological activity is substantially retained. Further, the invention also includes mutants of organisms hosting all or part of one or more of the DNA constructs of the invention. Such mutants can be made by techniques well known to persons skilled in the art. For example, UV irradiation can be used to prepare mutants of host organisms. Likewise, such mutants may include asporogenous host cells that also can be prepared by procedures well known in the art.

4.14 Peptide Nucleic Acid Compositions

In certain embodiments, the inventors contemplate the use of peptide nucleic acids (PNAs) in the practice of the methods of the invention. PNAs are DNA analogs that mimic the structure of the polynucleotide, in which the nucleobases are attached to a pseudopeptide backbone (Good and Nielsen, 1997). PNAs can be utilized in a number of methods that traditionally have used RNAs or DNAs (U.S. Pat. No. 5,786,461; U.S. Pat. No. 5,773,571, U.S. Pat. No. 5,766,855; U.S. Pat. No. 5,736,336; U.S. Pat. No. 5,719,262; and U.S. Pat. No. 5,539,082, each of which is specifically incorporated herein by reference in its entirety). Often PNA sequences perform better in techniques than the corresponding RNA or DNA sequences and have utilities that are not inherent to RNA or DNA. Methods of making, and using PNAs are also found in Corey (1997).

PNAs when delivered within cells have the potential to be general sequence-specific regulators of gene expression. Reviews of PNAs and their use as antisense and anti-gene agents exist (Nielsen et al., 1993; Hanvey et al., 1992; and Good and Nielsen, 1997). Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al, 1995), blocking of transcription factor binding (Vickers et al., 1995), genome cleavage (Veselkov et al., 1996), biosensors (Wang et al., 1996), in situ hybridization (Thisted et al., 1996), and in an alternative to Southern blotting (Perry-O'Keefe, 1996).

4.15 PEAMT-Specific Antibody Compositions and Formulations Thereof

Means for preparing and characterizing antibodies are well known in the art (see, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs that are specific for a PEAMT or ΔPEAMT peptide epitope, peptide, or polyepeptide may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody-producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody producing cells that are in the dividing plasmablast stage, and the latter because peripheral blood is easily accessible. Often, a panel of animals will have been immunized and the spleen of animal with the highest antibody titer removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B-lymphocytes from the immunized animal are then fused with cells of an immortal myeloma cell, generally one of the same species as the animal that was immunize Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, by Gefter et al. (1977). The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines may also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.16 Epitopic Core Sequences

The present invention is also directed to PEAMT/ΔPEAMT polypeptide compositions, free from total cells and other polypeptides, which comprise a purified PEAMT/ΔPEAMT polypeptide which incorporates an epitope that is immunologically cross-reactive with one or more of the PEAMT/ΔPEAMT-specific antibodies of the present invention.

As used herein, the term "incorporating an epitope(s) that is immunologically cross-reactive with one or more anti-PEAMT/ΔPEAMT antibodies" is intended to refer to a peptide or protein antigen which includes a primary, secondary or tertiary structure similar to an epitope located within a PEAMT/ΔPEAMT polypeptide. The level of similarity will generally be to such a degree that monoclonal or polyclonal antibodies directed against the PEAMT/ΔPEAMT polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of PEAMT/ΔPEAMT epitopes and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitope peptide directed to PEAMT/ΔPEAMT-related sequences. It is proposed that these regions represent those that are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen-binding sites on PEAMT/ΔPEAMT epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide or peptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar™ software, DNAStar, Inc., Madison, Wis.) may also be useful in designing synthetic epitopes and epitope analogs in accordance with the present disclosure.

In certain embodiments, particular advantages may be realized through the preparation of synthetic PEAMT/ΔPEAMT peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

To confirm that a polypeptide is immunologically cross-reactive with, or a biological functional equivalent of, one or more epitopes of the disclosed PEAMT/ΔPEAMT peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e. based upon competition for binding sites between antibodies and antigens.

Suitable competition assays that may be employed include protocols based upon immunohistochemical assays, ELISAs, RIAS, Western or dot blotting and the like. In any of the competitive assays, one of the binding components, generally the known element, such as a PEAMT or PEAMT-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between PEAMT/ΔPEAMT and any test antigen, one would first label PEAMT/ΔPEAMT with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to a known antibody. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label.

The reactivity of the labeled antigen, e.g., a PEAMT/ΔPEAMT-derived peptide, in the absence of any test antigen would be the control high value. The control low value would be obtained by incubating the labeled antigen with an excess of unlabeled antigen, when competition would occur and reduce binding. A significant reduction in labeled antigen reactivity in the presence of a test antigen is indicative of a test antigen that is "cross-reactive," i.e. that has binding affinity for the same antibody. "A significant reduction," in terms of the present application, may be defined as a reproducible (i.e. consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents that will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.18 Antisense Oligonucleotides Targeted to mRNA

In certain embodiments, the inventors contemplate the use of antisense compositions to negatively regulate the expression of a gene encoding PEAMT or ΔPEAMT in a host cell. The end result of the flow of genetic information is the synthesis of protein. DNA is transcribed by polymerases into messenger RNA and translated on the ribosome to yield a folded, functional protein. Thus, even from this simplistic description of an extremely complex set of reactions, it is obvious that there are several steps along the route where protein synthesis can be inhibited. The native DNA segment encoding PEAMT or ΔPEAMT has two strands: a sense strand and an antisense strand held together by hydrogen bonding. The messenger RNA encoding PEAMT or ΔPEAMT has the same nucleotide sequence as the sense DNA strand except that the DNA thymidine is replaced by uridine. Thus, antisense nucleotide sequences will bind to the mRNA encoding the PEAMT or ΔPEAMT polypeptides and inhibit production of the corresponding protein.

The targeting of antisense oligonucleotides to bind mRNA is one mechanism to shut down protein synthesis. For example, the synthesis of polygalactauronase and the muscarine type-2 acetylcholine receptor are inhibited by antisense oligonucleotides directed to their respective mRNA sequences (U.S. Pat. No. 5,739,119 and U.S. Pat. No. 5,759,829, U.S. Pat. No. 5,801,154; U.S. Pat. No. 5,789,573; U.S. Pat. No. 5,718,709 and U.S. Pat. No. 5,610,288, each specifically incorporated herein by reference in its entirety).

In illustrative embodiments, antisense oligonucleotides may be prepared which are complementary nucleic acid sequences that can recognize and bind to target genes or the transcribed mRNA, resulting in the arrest and/or inhibition of deoxyribonucleic acid (DNA) transcription or translation of the messenger ribonucleic acid (mRNA). These oligonucleotides can be expressed within a host cell that normally expresses PEAMT-specific mRNA to reduce or inhibit the expression of this mRNA. Thus, the oligonucleotides may be useful for reducing the level of PEAMT polypeptide in a suitably transformed host cell or transgenic plant.

The native nucleic acid segment encoding PEAMT has, as do all such plant DNAs, two strands: a sense strand and an antisense strand held together in a duplex formation by hydrogen bonding. The messenger RNA (mRNA) encoding PEAMT has the same nucleotide sequence as the sense DNA strand except that the thymidine in DNA is replaced by uridine in DNA. Thus, preferred antisense oligonucleotide compositions for use in the practice of the present invention are those sequences that specifically bind to the mRNA coding for PEAMT and that inhibit or reduce the expression of the PEAMT polypeptide encoding by that mRNA.

The present invention provides a composition comprising at least a first oligonucleotide of at least about 9 to about 45 or so bases in length, wherein the oligonucleotide specifically binds to a portion of mRNA expressed from a gene encoding a plant PEAMT polypeptide, and further wherein binding of the oligonucleotide to the mRNA is effective in decreasing the activity of or reducing the quantity of the PEAMT enzyme in a host plant cell expressing the mRNA.

In certain aspects of the invention, the oligonucleotide comprises deoxyribonucleic acid, ribonucleic acid, or peptide-nucleic acid. In particular embodiments, the oligonucleotide comprises a sequence of at least nine, at least ten, at least eleven, at least twelve, at least thirteen, or at least fourteen, up to and including the full-length contiguous sequences from SEQ ID NO: 1 or SEQ ID NO:3. When longer antisense molecules are required, one may employ an oligonucleotide that comprises a sequence of at least fifteen, at least sixteen, at least seventeen, at least eighteen, at least nineteen, or at least twenty, up to and including the full-length contiguous sequences from SEQ ID NO:1 or SEQ ID NO:3. Such antisense molecules may comprise even longer contiguous nucleotide sequences, such as those comprising about 21, about 22, about 23, about 24, about 25, about 26, about 27, about 28, about 29, or about 30 or so contiguous nucleotides from SEQ ID NO:1 or SEQ ID NO:3.

4.19 Definitions

In accordance with the present invention, nucleic acid sequences include and are not limited to DNA (including and not limited to genomic or extragenomic DNA), genes, RNA (including and not limited to mRNA and tRNA), nucleosides, and suitable nucleic acid segments either obtained from native sources, chemically synthesized, modified, or otherwise prepared by the hand of man. The following words and phrases have the meanings set forth below.

A, an: In accordance with long standing patent law convention, the words "a" and "an" when used in this application, including the claims, denotes "one or more".

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g. plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Cloning and Characterization of PEAMT 5.1.1 Experimental Procedures 5.1.1.1 Chemicals

[$^{32}$P]dCTP (3000 mCi mmol$^{-1}$) and [methyl-$^{14}$C]AdoMet (59 mCi mmol$^{-1}$) were purchased from NEN; the specific activity of AdoMet was adjusted to the desired value with unlabeled compound (Sigma, St. Louis, Mo.). Chiral HPLC (Beaudouin et al., 1993) showed that [methyl-$^{14}$C]AdoMet was >99% in the S,S (biologically active) form. Unlabeled AdoMet was 85% in the S,S form and 15% in the R,S (inactive) form; specific activities were calculated using the S,S-AdoMet content. [$^{33}$P]P-MME and [$^{14}$C]P-Cho were made as described (McNeil et al., 2000). Restriction and modification enzymes, and oligonucleotides were from Gibco-BRL, NEB or Boehringer Mannheim. P-Cho (Na$_2$ salt) was from TCI America (Portland, Oreg.). P-EA and all other biochemicals were from Sigma. AG-50 (HR$^+$) ion exchange resin was from BioRad. Silica gel G (0.25-mm) TLC plates were from Merck.

5.1.1.2 Plant Materials

*Spinacia oleracea* L. plants (cv. Savoy Hybrid 612, Harris Moran Seeds) were grown in coarse vermiculite with an 8-hr day at 24° C. (photosynthetic photon flux density 325 µmol m$^{-2}$s$^{-1}$) and 16-hr night at 19° C. Plants were irrigated daily with 0.5X Hoagland's solution. Prior to harvest, plants were held at nighttime conditions for 40 hr and then placed under day conditions for 8 hr; salinized plants were irrigated with 200 mM NaCl at the onset of the 8-hr day period (Smith et al., 1999). Harvested leaves were frozen in liquid N$_2$ and stored at –80° C.

5.1.1.3 Yeast Strains and Growth Conditions

The *S. pombe* strains used were 972h- (h$^{-s}$) and Bx22 (h$^{-s}$ cho2-20 ade6-M210 leu1-32) (Kanipes, 1997). Both were maintained on YEA medium (Kanipes et al., 1998) supplemented with 40 µM myo-inositol. SD medium was as described (Kanipes et al., 1998) except that it contained 110 µM myo-inositol, 1 g 1$^{-t}$ of CSM-leu (Bio101, Vista, Calif.), plus 250 mg 1$^{-1}$ each of lysine, adenine, uracil, and histidine, 1 mM EA and, for plates only, 20 mg 1$^{-1}$ phloxine B. All liquid media also contained 0.5 g 1$^{-1}$ asparagine.

5.1.1.4 cDNA Library Construction

A salinized spinach cDNA expression library was constructed in the *S. pombe* vector pREP3, which contains a thiamine-repressible expression cassette driven by the nmt promoter (Maundrell, 1993). To prepare pREP3 for library construction, it was digested with MscI and SalI, dephosphorylated with shrimp alkaline phosphatase, ligated to an adapter made by hybridizing the oligonucleotides 5'-CTCGAGATCTG-3' (SEQ ID NO:5) and 5'-TCGACAGATCTCGAG-3' (SEQ ID NO:6), digested with XhoI, gel-purified and religated. This replaced the MscI site with XhoI and BglII sites in the polylinker, creating pREP3A. The cDNA library was directionally cloned in the BglII/SalI sites; to ensure these sites were accessible, a 2.2-kb BglII/SalI fragment from pJD301 (Luehrsen et al., 1992) was ligated to pREP3A creating pREP3B. Total RNA was isolated from salinized spinach leaves as described (Rathinasabapathi et al., 1997). Poly(A)+ RNA was isolated on poly-U Sephadex (Hondred et al., 1987) and used to construct cDNA with the Stratagene ZAP-cDNA synthesis kit, replacing the kit's EcoRI adapter with a BglII adapter made by hybridizing the oligonucleotides 5'-CTCGTGCCA-3' (SEQ ID NO:7) and 5'-GATCTGGCACGAG-3 (SEQ ID NO:8). Size-selected cDNAs (average length 1.2 kb) were ligated to pREP3B BglII/SalI under optimized conditions and transformed into XL1-Blue MRF cells by electroporation. The expression library (3.2×10$^6$ colony forming units) was amplified as described (Alexander, 1987).

5.1.1.5 Complementation of a Cho2$^-$ Mutant

Plasmid DNA from the spinach expression library was prepared and transformed into Bx22 cells by standard procedures (Kanipes et al., 1998). Transformants were selected on SSD medium and then replica-plated onto SD medium containing 1 mM EA to select for colonies displaying the complemented phenotype. Complementing plasmids were rescued and transformed into *E. coli* DH10B cells for analysis. Sequencing was carried out using the ABI Prism dye terminator cycle sequencing Ready Reaction (PE Applied Biosystems, Foster City, Calif.) and an ABI model 373 sequencer.

5.1.1.6 Construction of ΔPEAMT

The plasmid encoding PEAMT, designated pREP3-PEAMT, was digested with BamHI and end-polished with T4 DNA polymerase. The 3'-sequence of PEAMT was removed by digestion with MscI; the remaining sequence plus vector was gel-purified and religated to give ΔPEAMT. In ΔPEAMT the native coding sequence terminates at Gly-286, and the pREP3 polylinker adds the sequence Ile Pro Gly to the carboxyl-terminus.

5.1.1.7 RNA Gel Blot Analysis

Total RNA was prepared from unstressed and salinized spinach leaves using the RNAeasy plant mini kit (Qiagen, Valencia, Calif.). Ten-µg samples of RNA were separated in formaldehyde/1.5% agarose gels and transferred to supported nitrocellulose membrane (NitroPure, MSI, Westborough, Mass.), hybridized and washed according to the manufacturer's protocols. The PEAMT probe template was a 1.2-kb BamHI/BglII fragment of pREP3-PEAMT. The rRNA probe template was a 0.9-kb SmaI fragment of a *Zamia pumila* rRNA clone (Nairn and Ferl, 1988). Probes were labeled with [$^{32}$P]dCTP by the random primer method. Hybridization was detected by autoradiography.

5.1.1.8 Enzyme Isolation and Molecular Mass Determination

Cells were grosn to an OD$_{600}$ of ≈1 in 50 ml of medium at 30° C., shaking at 250 rpm. The media were SD containing 250 mgl$^{-1}$ leucine for Bx22 cells, and SSD for wild type cells and Bx22 cells harboring pREP3-PEAMT or pREP3-ΔPEAMT. Subsequent operations were at 0–4° C. Cells were harvested by centrifugation (5000×g, 10 min), washed twice with water and once with 100 mM HEPES-KOH, pH 7.8, resuspended in 0.5 ml of lysis buffer (100 mM HEPES-KOH, pH 7.8, 2 mM Na$_2$EDTA, 5 mM dithiothreitol, 10% glycerol) and transferred to 2-ml microfuge tubes containing ≈1.5 g of acid-washed glass beads (425–600 µm). Cells were broken by vortexing at maximum speed for 2 min. The brei was centrifuged (16,000×g, 2 min), the supernatant was removed and the beads were washed with 3×1 ml of lysis buffer. The combined supernatants were clarified by centrifugation (16,000×g, 15 min) and desalted on a PD-10 column (Amersham Pharmacia Biotech, Piscataway, N.J.) equilibrated with storage buffer (10 mM HEPES-KOH, pH 7.8, 2 mM Na$_2$EDTA, 5 mM dithiotreitol, 10% glycerol). The extract was aliquotted, frozen in liquid N$_2$ and stored at –80° C. Spinach leaf extracts were prepared as described (Summers and Weretilnyk, 1993). Protein was determined using the Bio-Rad dye reagent (Hercules, Calif.). Native molecular mass was estimated using a Waters 626 HPLC system (Milford, Mass.) equipped with a Superdex 200 HR 10/30 column (Amersham Pharmacia Biotech) as described (Weretilnyk et al., 1995).

5.1.1.9 Enzyme Assays

PEAMT activity was measured by a modification of published methods (Datko and Mudd, 1988b; Summers and Weretilnyk, 1993), under conditions in which product formation was proportional to enzyme concentration and time. Unless otherwise indicated, assays (final volume 100 µl) contained 10 µl 10X assay buffer (1 M HEPES-KOH, 20 mM $Na_2EDTA$, pH 8.6), 10% glycerol, 100 nCi [methyl-$^{14}C$]AdoMet, P-EA and enzyme extract as specified in the text, and were incubated at 30° C. for 15 min. The final pH in the assays was 8.1. Reactions were stopped by adding 1 ml of ice-cold water; each was applied to a 1-ml AG-50 ($HR^+$) column held at 4° C. and the assay tube was rinsed with 1 ml of water, which was also applied to the column. Products were eluted with 10 ml of 0.1 N HCl, and 2 ml of the eluate was mixed with 3 ml of Ready Gel scintillation fluid (Beckman, Palo Alto, Calif.) and counted. For assay blanks, enzyme was omitted during incubation and added just before the ion exchange step. Product recovery was determined to be 84% by spiking unlabeled reaction mixtures with [$^{14}C$]P-Cho, and experimental values were corrected accordingly. Reaction products were separated by TLC on silica gel G plates developed in methanol:acetone::concentrated HCl (90:10:4, vol./vol./vol.) (TLC system 1), and detected by autoradiography.

AdoMet:EA N-methyltransferase activity was assayed as above except that reactions contained 200 nmol EA and 160 nmol (40 nCi) of [methyl-$^{14}C$]AdoMet. The [methyl-$^{14}C$]AdoMet was removed by treating with activated charcoal and centrifuging (Cook and Wagner, 1984), and $^{14}C$-incorporation into freebase products was measured by counting a sample of the supernatant. TLC tests confirmed that the charcoal did not bind free bases. For assay blanks, EA was omitted. AdoMet:Ptd-EA N-methyltransferase activity was measured essentially as described (Datko and Mudd, 1988b). Assays (final volume 100 µl) contained 9 µl 10X assay buffer, 0.8 nmol (47 nCi) [methyl-$^{14}C$]AdoMet, 10 µl of a Ptd-EA emulsion in 1× assay buffer (10 mg $ml^{-1}$, sonicated for 3×30 sec), and enzyme extract; incubation was for 30 min at 30° C. The phospholipid fraction was isolated for $^{14}C$ quantification as described (Datko and Mudd, 1988b) except that the methanol:chloroform:water proportions were 12:5:1 (vol./vol./vol.). Data were corrected for the $^{14}C$ incorporation in control assays containing extract from Bx22 cells.

5.1.2 Results

5.1.2.1 PEAMT Cloning by Complementation of a S. POMBE Cho2 Mutation

Figure 1A:
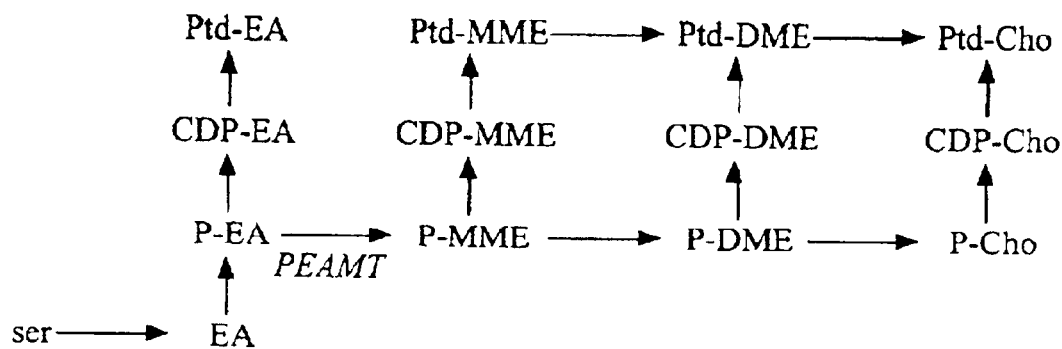
FIG. 1A illustrates the biogenesis of choline moieties in plants, and the complementation strategy used to identify PEAMT. Shown are the pathways found in leaves and other vegetative tissues of higher plants.
Figure 1B:
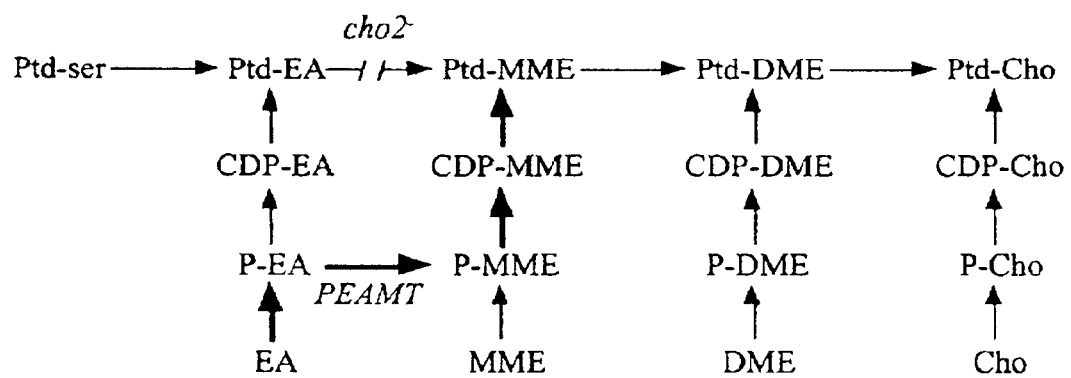
FIG. 1B illustrates the biogenesis of choline moieties in S. pombe, and the complementation strategy used to identify PEAMT. Shown is the native pathway in S. pombe (light arrows) and the bypass route (heavy arrows) that allows PEAMT to substitute for the defective cho2 gene product.

Cho moieties are synthesized de novo in *S. pombe* via three sequential methylations of Ptd-EA. The cho2 gene product mediates the first of these, Ptd-EA→Ptd-MME (FIG. 1B), and cho2⁻ mutants require MME, DME or Cho for growth (Kanipes and Henry, 1997). *S. pombe* incorporates pre-formed Cho or other free bases into phospholipids via the CDP-base or Kennedy pathway, i.e. base→P-base→CDP-base→Ptd-base (FIG. 1B) (Kanipes and Henry, 1997). These features of Cho metabolism in *S. pombe* suggested that PEAMT could be cloned by complementation of a cho2⁻ mutant, because expression of PEAMT would restore Cho prototrophy by installing a bypass to the blocked Ptd-EA methylation step (FIG. 1B).

A cDNA expression library was therefore constructed in the *S. pombe* expression vector pREP3 using mRNA from salinized spinach leaves, salinization being known to increase PEAMT activity (Weretilnyk et al., 1995). The pREP3 plasmid contains the leu2 gene for selection and a thiamine-repressible expression cassette (Maundrell, 1993). The amplified library was transformed into *S. pombe* strain Bx22, a leu1 cho2⁻ mutant (Kanipes and Henry, 1997). Transformants were selected first for leucine prototrophy on medium containing thiamine and Cho, then replica plated onto medium without thiamine and with EA in place of Cho. Screening ≈30,000 transformants in this way identified 24 complemented colonies that harbored plasmids with the same 2.2-kb insert, as judged by restriction analysis and sequencing. No complementation was obtained with the vector alone and retransformation of Bx22 with rescued plasmid conferred Cho prototrophy, establishing that the complementation is due to the encoded plant protein. The complemented strain lacked detectable activity with Ptd-EA or EA as substrates (<1 pkat $mg^{-1}$ protein) but had high PEAMT activity (FIG. 2A). TLC analysis of the PEAMT reaction mixtures confirmed that P-MME was formed (FIG. 2A, inset). The specific activity of PEAMT in extracts of complemented cells was up to 80-fold greater than that in salinized spinach leaves (FIG. 2A).

Because sequence analysis showed that PEAMT has two methyltransferase domains (see below), a convenient MscI site was used to remove almost all of the C-terminal domain (FIG. 2B). The truncated construct (ΔPEAMT) remained able to complement the cho2 mutation and specified a protein with PEAMT activity (FIG. 2A).

5.1.2.2 Analysis of the PEAMT cDNA Sequence

The PEAMT cDNA comprises a 494-residue open reading frame (FIG. 3) flanked by long 5'- and 3'-untranslated regions (253 and 496 bp, respectively). The deduced polypeptide (56.4 kDa) can be divided in the center (FIG. 3, arrowhead) into two sequences that share significant homology (21% identity, 53% similarity), each of which contains the consensus sequences (Kagan and Clarke, 1994; Gary et al., 1996) for methyltransferase motifs I, post-I, II and III (FIG. 2B and FIG. 3). PEAMT thus appears to contain two distinct but related methyltransferase domains. This is consistent with its size, which is roughly double that typical of small molecule methyltransferases (Fujioka, 1992). The deduced PEAMT sequence has no recognizable N-terminal signal sequence, consistent with biochemical evidence that the spinach enzyme is cytosolic (Weretilnyk et al., 1995).

The novel, bipartite structure of PEAMT prompted a search for homologous sequences in GenBank™, to determine whether similar proteins occur in other plants. PEAMT homologs were found in species representing three other families: *Malvaceae* (e.g., cotton), *Brassicaceae* (e.g., *Arabidopsis* and canola) and *Gramineae* (e.g., barley and rice). The *Arabidopsis* protein was predicted from genomic DNA sequence and was complete (FIG. 3); those for other species were fragments deduced from expressed sequence tags (ESTs) spanning the junction between the domains.

5.1.2.3 Properties of Recombinant PEAMT

The native molecular mass was estimated by size exclusion chromatography to be 57 kDa, indicating that the enzyme exists as a monomer. PEAMT activity showed a broad pH optimum in the region 8.1–8.5; the $K_m$ values for P-EA and AdoMet were 96 and 140 µM, respectively. In view of the bipartite structure of PEAMT and the finding that highly purified (but not homogenous) PEAMT preparations from spinach catalyze the methylation of P-MME and P-DME as well as of P-EA (Smith et al., 1999), it was of interest to determine whether the recombinant enzyme mediates more than the first methylation of P-EA. The products formed when PEAMT is incubated for long periods with a small amount of P-EA and >3.5-fold excess of [methyl-$^{14}$C]AdoMet were analyzed. In these conditions, $^{14}$C appears successively in P-MME, P-DME and P-Cho, as shown qualitatively in FIG. 4A. As incubation proceeds, the molar quantities of P-MME and P-DME peak and then decline while P-Cho continues to accumulate (FIG. 4B). These results establish that PEAMT catalyzes all three methylations required to convert P-EA to P-Cho, and also show that the intermediates P-MME and P-DME do not invariably remain bound to the enzyme because both accumulate transiently during the reaction.

5.1.2.4 Products of the Reaction Catalyzed by the N-Terminal PEAMT Domain

Deleting the C-terminal domain of PEAMT did not abolish complementation or enzyme activity (FIG. 2A). The N-terminal domain thus catalyzes the first methylation of EA—but not necessarily the others. The reaction products of the truncated (ΔPEAMT) and wild type enzymes were therefore compared. After a 3-hr incubation with a small quantity of P-EA and a 5-fold excess of [methyl-$^{14}$C] AdoMet, ΔPEAMT yields only [$^{14}$C]P-MME whereas the wild type enzyme yields, as expected, almost solely [$^{14}$C] P-Cho (FIG. 5A). This result demonstrates that the N-terminal methyltransferase domain mediates only the first N-methylation of P-EA, and strongly implies that the C-terminal domain mediates the other two. In this connection it is noteworthy that the kinetics of product formation for the wild type enzyme (FIG. 4B) show that P-MME accumulates to a higher level than P-DME. This is consistent with the second and third methylation steps occurring at the same catalytic site, from which the intermediate P-DME does not exit very freely.

5.1.2.5 Sensitivity to P-Cho and Other Metabolites

Recombinant wild type PEAMT was strongly inhibited by its product P-Cho (FIG. 5B), as reported for the activity extracted from spinach or Lemna plants (Smith et al., 1999; Mudd and Datko, 1989a). Activity was reduced by 80% at 2 mM and by 95% at 10 mM P-Cho, 10 mM being approximately the P-Cho concentration in the cytosol of spinach leaves (Bligny et al., 1990; Winter et al., 1994). This effect appeared specific inasmuch as Cho, GlyBet, MME and DME were not inhibitory at 2 mM. The truncated ΔPEAMT enzyme remained sensitive to P-Cho, although significantly (P=0.05) less so than the wild-type enzyme, retaining twice as much of its initial activity at the physiological P-Cho concentration of 10 mM (FIG. 5B).

5.1.2.6 Effect of Salinization on PEAMT mRNA Level

RNA gel blot analyses revealed an approximately 2.5-kb PEAMT mRNA in spinach leaves, which was consistent with the size of the cDNAs that were isolated. Upon salinization, there was an approximately 10-fold increase in PEAMT mRNA abundance, and this was accompanied by an 8-fold rise in enzyme activity (FIG. 6). This indicates that the salt-induction of PEAMT activity reported previously (Summers and Weretilnyk, 1993; Weretilnyk et al., 1995) results principally, if not solely, from increased gene expression.

5.1.3 Discussion

The complementation strategy used to clone PEAMT was not narrowly specific because in principle the cho2 mutation (in Ptd-EA N-methyltransferase) could have been complemented by plant genes encoding N-methyltransferases acting on Ptd-EA or free EA as well as on P-EA. It is therefore significant that all 24 complemented S. pombe strains that were recovered harbored a plasmid encoding PEAMT, for this implies that N-methyltransferases acting on Ptd-EA or EA are either absent or expressed at far lower levels. This evidence reinforces the conclusion from in vivo radiolabeling studies (Rhodes and Hanson, 1993; Hanson and Rhodes, 1983; Summers and Weretilnyk, 1993; Datko and Mudd, 1988a) and enzyme assays (Datko and Mudd, 1988b; Summers and Weretilnyk, 1993; Weretilnyk et al., 1995) that in plant leaves the first methylation in the synthesis of Cho moieties takes place exclusively at the phosphobase level.

The large size and tandem-domain structure of PEAMT indicate that it is the product of a fusion between two related methyltransferase genes. That this fusion is an ancient one that predates the radiation of the Angiosperms is shown by the occurrence of PEAMT homologs in species from four diverse families (Chenopodiaceae, Malvaceae, Brassicaceae and Gramineae) whose progenitors diverged >125 million years (Myr) ago (Crane et al, 1995). In view of the probable evolutionary age of the fused enzyme it is particularly interesting that at least one of its domains retains what is presumably its ancestral activity (conversion of P-EA to P-MME) when expressed separately.

Spinach PEAMT is a novel protein, and there is no precedent for the synthesis of Cho moieties via an enzyme composed of two fused N-methyltransferases. Three separate enzymes are required to convert P-EA to P-Cho in nerve tissues (Mukherjee et al., 1995), and two separate enzymes carry out the Ptd-EA→Ptd-MME and Ptd-MME→→Ptd-Cho steps in fungi (Kanipes and Henry, 1997). R. sphaeroides and liver have enzymes that mediate all three methylations in Ptd-Cho synthesis, but these are small (22–23 kDa) proteins that appear to have only one methyltransferase domain (Vance et al., 1997; Arondel et al., 1993). It is, however, noteworthy that the genome of the nematode Caenorhabditis elegans includes a hypothetical protein (GenBank Accession No. AAB04824, 437 residues) that shares homology throughout its length with PEAMT and has two methyltransferase domains. Other organisms may therefore have two-domain phosphobase N-methyltransferases that remain to be discovered. It is also noteworthy that soybean cell extracts mediate only the first methylation of P-EA (Datko and Mudd, 1988b; Rhodes and Hanson, 1993; Hanson and Rhodes, 1983; Summers and Weretilnyk, 1993; Datko and Mudd, 1988a) and that spinach leaves have P-MME and P-DME N-methyltransferase activities that appear to be independent of PEAMT activity (Smith et al, 1999; Weretilnyk et al., 1995). Plants may therefore have other phosphobase N-methyltransferases besides PEAMT.

These data show for the first time that PEAMT is regulated at the gene level, because the mRNA is strongly induced in leaves by salinization. They also confirm that PEAMT is regulated at the enzyme level, because the activity is sensitive to the reaction product P-Cho. The activity was 95% inhibited at a P-Cho concentration of 10 mM, the physiological level in spinach leaf cytosol (Bligny et at, 1990). As this inhibition was measured in the presence of a saturating P-EA concentration, the degree of inhibition in vivo is probably greater. Together, these findings support the view that PEAMT is the committing step in the synthesis of Cho moieties in plants and that it exerts major control over the flux to P-Cho and its metabolites (Datko and Mudd, 1988a; Mudd and Datko, 1989a; Mudd and Datko, 1989b). Specifically in spinach, the salt-induction of PEAMT fits with the increased demand for Cho to support GlyBet accumulation, for which the two biosynthetic enzymes are also induced at the gene level by salinity (Rhodes and Hanson, 1993; Rathinasabapathi et al, 1997).

The cloning and characterization of PEAMT was driven by the need to understand the pathway and regulation of Cho synthesis in plants, in order to engineer an enhanced Cho supply to support GlyBet synthesis (Nuccio et al., 1998; Nuccio et at, 1999). In this context, it is convenient that a single gene encodes all three N-methyltransferase activities needed to produce P-Cho. However, the strong feedback inhibition of native PEAMT by P-Cho could render raising the level of PEAMT relatively ineffective in increasing the flux to P-Cho. The fact that the N-terminal domain expressed separately is less sensitive to feedback control may therefore be valuable in engineering. Since most if not all plants have the capacity to carry out the second and third methylations of Cho synthesis at the phosphatidylbase level (Datko and Mudd, 1988b; Rhodes and Hanson, 1993), and there may also be phosphobase N-methyltransferases specific for these steps (Smith et al., 1999; Weretilnyk et al., 1995), a partially desensitized enzyme able to carry out just the first methylation could prove more effective than native PEAMT in enhancing Cho biogenesis.

5.2 Example 2

Sequence of PEAMT Polypeptides and Polynucleotides 5.2.1 Sequence of Spinach PEAMT-Encoding DNA (SEQ ID NO:1)

CATTCATTTGAAGCGTGGAAGTAGTAGTTTTGT
GGTAGAGTGAATTTGATACTCCTACTGCTCA
TGCGGCAGAGAGGCAGGGCTTCGAACCGTAG
ATCCAGGACTTTTTCTCGTTCTCGCATTGCCA
TTGAGGGTCACTAATACTTTTAACTATCTCCTT
CTTTTTCTTTCCCACAATTTCTGCGTTTTCAC
GCACATTAATCTCACCTATTTTCTAGCTTC
TTCATTTTCTCAATCAATCTCTCGTGTTATTATGG
CCGCTTCAGCTATGGGAGTGTTGCAAGAGAG
AGAGGTGTTCAAGAAATACTGGATTGAACAC
TCTGTTGATTTGACTGTTGAGGCTATGATGC
TTGATTCACAAGCTTCAGATCTTGACAAAGT
GGAGCGACCTGAGGTACTTTCCATGCTTCCACC
TTATGAAGGAAAGTCTGTCTTAGAACTCGGTGC
TGGTATTGGTCGTTTTACTGGTGAATTGGCCG
AGAAAGCTAGCCAGGTCATCGCTCTGGATTT
CATTGAGAGTGTTATAAAGAAGAATGAAAGCAT
AAATGGGCATTACAAAAATGTGAAGTTTAT
GTGTGCTGATGTGACATCTCCAAGTCTCA
ACATTTCACCAAATTCCGTGGATATCATATTCTC
CAATTGGCTACTCATGTATCTTTCTGATGAAGAG
GTTGAGCGTCTGGTTGAAAGGATGTTGAAATG
GTTGAAGCCAGGAGGATACATTTTCTTCAG
AGAATCTTGTTTTCATCAATCAGGAGATC
ACAAGCGCAAAAGCAATCCAACCCACTACCGT
GAACCTAGGTTCTACACCAAGATCTTCAAA
GAATGCCATATGCAAGATGATTCTGGGAACTC
CTATGAGCTCTCCCTAACTGGCTGCAAATGTAT
TGGAGCTTATGTCAAAAGCAAGAAGAAT
CAGAACCAGATAAGCTGGTTATGGCAGAAAGTT
GATTCAGAGGATGACAAGGGGTTCCAGCGAT
TCTTGGATTCTAGTCAATACAAGTTTAACAGCAT
ACTGCGTTATGAGCGTGTATTTGGTCCTGGTTAT
GTTAGTACCGGAGGACTCGAAACAACCAAG
GAGTTTGTATCAAAGCTTGACTTGAAGCCTG
GCCAGAAGGTCCTAGATGTGGGTTGTGGCATAG
GTGGAGGTGATTTTACATGGCAGAGAACTATG
ATGTTGAGGTTGTTGGAATTGATCTCTCCATTA
ATATGATTTCTTTTGCCCTTGAGCGCTCAATTGG
CCTCAAATGTGCTGTTGAGTTTGAGGTGGCAGA
TTGCACCAAGAAAGATTACCCTGAAAACTCTTTT
GATGTCATCTACAGCCGTGATACCATTCTGCA
TATTCAGGACAAACCTGCTTTATTTAGATCCT
TCCACAAATGGTTGAAACCTGGAGGCAAAGTT
CTTATTAGTGACTACTGTAAGAGTGCTGGTACAC
CTTCAGCTGAATTTGCTGCATACATCAGGCA
GAGGGGATATGATCTCCACGATGTGAAGGC
ATATGGCAAGATGCTTAAAGATGCTGGATTC
GTTGAGGTTATTGCTGAGAATAGGACTGACC
AGTTCATTCAAGTTCTGCAGAAGGAACTAGAT
GCTCTTGAACAGGAGAAGGATGACTTCATTGAT
GATTTCTCTGAGGAGGATTATAACGACATA
GTTGATGGTTGGAAGGCCAAGTTGGTGAGG
ACTACAGAGGGTGAGCAACAATGGGGTTTGTT
CATTGCCAAGAAAATGTGAAGAATGAGCTGGT
GAAAGCAGCACGGTGCCTTT TTCTAGTATTAGTT
TATCAATGTATTTTCAGTTCATGGACTGTATATG
CAAAATCTACCAATAAGCTGTGAGTTGCAAACT
GAAAGATGATTTCTTATAGTCACTTCTGAATTAG
CACAAGCAGTGAAGTTCGCATAAGAAACT
GAAGGGAACTCATGGAGTTGCAGACGAAATCAT
CAAAACGGCAGAACCCACTCTCTATATGA
GATCTAGTGGTTAAGTTATGTGTTTTGTACA
TTTTCCGTTCCAAGTTCACTCAATCTTACCA
TCATAATATCACCGCTTTTACTTCTTTATATGG
TGGATTGAAGTCGAAACTCTTTGTTAGTAATGT
GTATTAGTTTGTTGAAAGTGGAACTTGCAA
CACACTTATTCACAAGTGTGTAGGGAAATATG
GATTTTGTATTAGTATGTACTGCACTTAGTTGT
TAAAAGGATACTTCCTACGTTTTCTTCTGTTGCA 5.2.2 Sequence of Spinach PEAMT Polypeptide (SEQ ID NO:2)

MAASAMGVLQEREVFKKYWIERSVDLTVEAMMLD
SQASDLDKVERPEVLSMLPPYEGKSVLELGAGI
GRFTGELAEKASQVIALDFIESVIKKNESINGH
YKNVKFMCADVTSPSLNISPNSVDIIFSNWLL
MYLSDEEVERLVERMLKWLKPGGYIFFRESCF
HQSGDHKRKSNPTHYREPRFYTKIFKECH
MQDDSGNSYELSLIGCKKCIGAYVKSKKNQNQI
SWLWQKVDSEDDKGFQRFLDSSQYKFNSILRYE
RVFGPGYVSTGGLETTKEPVSKLDLKPGQKVLD
VGCGIGGGDFYMAENYDVEVVGIDLSINMISFAL
ERSIGLKCAVEFEVADCTKKDYPENSFDVIY
SRDTILHIQDKPALFRSFHKWLKPGGKVLISDYCK
SAGTPSAEFAAYIRQRGYDLHDVKAYGKMLKD
AGFVEVIAENRTDQFIQVLQKELDALEQEK
DDFIDDFSEEDYNDIVDGWKAKLVRTTEGE
QQWGLFIAKKM 5.2.3 Sequence of Gene Encoding Spinach ΔPEAMT Polypeptide (SEQ ID NO:3)

CATTCATTTGAAGCGTGGAAGTAGTAGTTTTGT
GGTAGAGTGAATTTGATACTCCTACTGCTC
ATGCGGCAGAGAGGCAGGGCTTCGAACCGTAG
ATCCAGGACTTTTTCTCGTTCTCGCATTGCCA
TTGAGGGTCACTAATACTTTTAACTATCTCCT
TCTTTTTCTTTCCCACAATTTCTGCGTTTTCACG
CACATTAATCTCACCTATTTTCTAGCTTCTT
CATTTTCTCAATCAATCTCTCGTGTTATTATGGC
CGCTTCAGCTATGGGAGTGTTGCAAGAGAG
AGAGGTGTTCAAGAAATACTGGATTGAAC
ACTCTGTTGATTTGACTGTTGAGGCTATGATGCT
TGATTCACAAGCTTCAGATCTTGACAAAGTGGAG
CGACCTGAGGTACTTTCCATGCTTCCACCTTA
TGAAGGAAACTCTGTCTTAGAACTCGGTGCTGG
TATTGGTCGTTTTACTGGTGAATTGGCCGA
GAAAGCTAGCCAGGTCATCGCTCTGGATTTC
ATTGAGAGTGTTATAAAGAAGAATGAAAGCAT
AAATGGGCATTACAAAAATGTGAAGTTTATGT
GTGCTGATGTGACATCTCCAAGTCTCAACA
TTTCACCAAAT TCCGTGGATATCATATTCTCCAAT

TGGCTACTCATGTATCTTTCTGATGAAGAGGT
TGAGCGTCTGGTTGAAAGGATGTTGAAATGGT
TGAAGCCAGGAGGATACATTTTCTTCAGA
GAATCTTGTTTTCATCAATCAGGAGATCAC
AAGCGCAAAAGCAATCCAACCCACTACCGT
GAACCTAGGTTCTACACCAAGATCTTCAA
AGAATGCCATATGCAAGATGATTCTGGGAACTC
CTATGAGCTCTCCCTAATTGGCTGCAAATGTAT
TGGAGCTTATGTCAAAAGCAAGAAGAAT
CAGAACCAGATAAGCTGGTTATGGCAGAAAGT
TGATTCAGAGGATGACAAGGGGTTCCAGCGAT
TCTTGGATTCTAGTCAATACAAGTTTAACAGCAT
ACTGCGTTATGAGCGTGTATTTGGTCCTGGTTAT
GTTAGTACCGGAGGACTCGAAACAACCAAG
GAGTTTGTATCAAAGCTTGACTTGAAGCCTG
GGATCCCCGGG 5.2.4 Sequence of Spinach ΔPEAMT Polypeptide (SEQ ID NO:4)

MAASAMGVLQEREVFKKYWIEHSVDLTVEAMMLD
SQASDLDKVERPEVLSMLPPYEGKSVLELGAGI
GRFTGELAEKASQVIALDFIESVIKKNESING
HYKNVKFMCADVTSPSLNISPNSVDIIFSNW
LLMYLSDEEVERLVERMLKWLKPGGYIFFRESCF
HQSGDHKRKSNPTHYREPRFYTKIFKECH
MQDDSGNSYELSLIGCKCIGAYVKSKKNQNQ
ISWLWQKVDSKDDKGFQRFLDSSQYKFNSILRY
ERVFGPGYVSTGGLETTKEFVSKLDLKPGIPG

6.0 REFERENCES

The following literature citations as well as those cited above are incorporated in pertinent part by reference herein for the reasons cited in the above text:

U.S. Pat. No. 4,196,265, issued Apr. 1, 1980.
U.S. Pat. No. 4,342,832, issued Aug. 3, 1982.
U.S. Pat. No. 4,356,270, issued Oct. 26, 1982.
U.S. Pat. No. 4,362,817, issued Dec. 7, 1982.
U.S. Pat. No. 4,371,625, issued Feb. 1, 1983.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,873,192, issued Oct. 10, 1989.
U.S. Pat. No. 4,943,674, issued Jul. 24, 1990.
U.S. Pat. No. 4,965,188, issued Oct. 23, 1990.
U.S. Pat. No. 5,097,025, issued Mar. 17, 1992.
U.S. Pat. No. 5,106,739, issued Apr. 21, 1992.
U.S. Pat. No. 5,110,732, issued May 5, 1992.
U.S. Pat. No. 5,139,954, issued Aug. 19, 1992.
U.S. Pat. No. 5,176,995, issued Oct. 15, 1991.
U.S. Pat. No. 5,177,011, issued Jan. 5, 1993.
U.S. Pat. No. 5,324,253, issued Jun. 28, 1994.
U.S. Pat. No. 5,378,619, issued Jan. 3, 1995.
U.S. Pat. No. 5,399,680, issued Mar. 21, 1995.
U.S. Pat. No. 5,401,836, issued Mar. 28, 1995.
U.S. Pat. No. 5,405,765, issued Apr. 11, 1995.
U.S. Pat. No. 5,436,393, issued Jul. 25, 1995.
U.S. Pat. No. 5,441,884, issued Aug. 15, 1995.
U.S. Pat. No. 5,442,052, issued Aug. 15, 1995.
U.S. Pat. No. 5,447,858, issued Sep. 5, 1995.
U.S. Pat. No. 5,459,252, issued Oct. 17, 1995.
U.S. Pat. No. 5,472,869, issued Dec. 5, 1995.
U.S. Pat. No. 5,484,956, issued Jan. 16, 1996.
U.S. Pat. No. 5,491,288, issued Feb. 13, 1996.
U.S. Pat. No. 5,504,200, issued Apr. 2, 1996.
U.S. Pat. No. 5,530,196, issued Jun. 25, 1996.
U.S. Pat. No. 5,538,879, issued Jul. 23, 1996.
U.S. Pat. No. 5,539,082, issued Jul. 23, 1996.
U.S. Pat. No. 5,576,198, issued Nov. 19, 1996.
U.S. Pat. No. 5,589,583, issued Dec. 31, 1996.
U.S. Pat. No. 5,589,610, issued Dec. 31, 1996.
U.S. Pat. No. 5,589,614, issued Dec. 31, 1996.
U.S. Pat. No. 5,595,896, issued Jan. 21, 1997.
U.S. Pat. No. 5,608,144, issued Mar. 4, 1997.
U.S. Pat. No. 5,610,042, issued Mar. 11, 1997.
U.S. Pat. No. 5,610,288, issued Mar. 11, 1997.
U.S. Pat. No. 5,614,399, issued Mar. 25, 1997.
U.S. Pat. No. 5,629,183, issued May 13, 1997.
U.S. Pat. No. 5,633,363, issued May 27, 1997.
U.S. Pat. No. 5,633,439, issued May 27, 1997.
U.S. Pat. No. 5,633,440, issued May 27, 1997.
U.S. Pat. No. 5,633,441, issued May 27, 1997.
U.S. Pat. No. 5,646,333, issued Jul. 8, 1997.
U.S. Pat. No. 5,659,124, issued Aug. 19, 1997.
U.S. Pat. No. 5,689,040, issued Nov. 18, 1997.
U.S. Pat. No. 5,689,049, issued Nov. 18, 1997.
U.S. Pat. No. 5,689,051, issued Nov. 18, 1997.
U.S. Pat. No. 5,689,056, issued Nov. 18, 1997.
U.S. Pat. No. 5,712,112, issued Jan. 27, 1998.
U.S. Pat. No. 5,718,709, issued Feb. 17, 1998.
U.S. Pat. No. 5,719,262, issued Feb. 17, 1998.
U.S. Pat. No. 5,736,336, issued Apr. 17, 1998.
U.S. Pat. No. 5,739,119, issued Apr. 14, 1998.
U.S. Pat. No. 5,759,829, issued Jun. 2, 1998.
U.S. Pat. No. 5,766,855, issued Jun. 16, 1998.
U.S. Pat. No. 5,773,571, issued Jun. 30, 1998.
U.S. Pat. No. 5,786,461, issued Jul. 28, 1998.
U.S. Pat. No. 5,789,573, issued Aug. 4, 1998.
U.S. Pat. No. 5,801,154, issued Sep. 1, 1998.
U.S. Pat. No. 5,859,347, issued Jan. 12, 1999.
U.S. Pat. No. 5,866,793, issued Feb. 2, 1999.
U.S. Pat. No. 5,874,265, issued Feb. 23, 1999.
U.S. Pat. No. 5,874,626, issued Feb. 23, 1999.
U.S. Pat. No. 5,886,244, issued Mar. 23, 1999.
U.S. Pat. No. 6,023,013, issued Feb. 8, 2000.
Eur. Pat. Appl. Publ. No. EP 0120516.
Eur. Pat. Appl. Publ. No. EP 75444.
Int. Pat. Appl. Publ. No. WO 84/02913.
Abdullah et al., *Biotechnology*, 4:1087, 1986.
Alexander, *Methods Enzymol.*, 154:41–64, 1987.
Altschul et al., "Basic local alignment search tool," *J. Mol. Biol.*, 215:403–410, 1990.
An et al., *EMBO J.*, 4:277–287, 1985.
Andriamampanry, Freysz, Kanfer, Dreyfus and Massarelli, *J. Neurochem.*, 56:1845–1850, 1991.
Arondel, Benning and Somerville, *J. Biol. Chem.*, 268:16002–16008, 1993.
Arz et al., *Biochim. Biophys. Acta*, 1218(3):447–452, 1994.
Bagdasarian, Lurz, Ruckert, Franklin, Bagdasarian, Frey, Timmis, "Specific-purpose plasmid cloning vectors. II. Broad host range, high copy number, RSF 1010-derived vectors, and a host-vector system for gene cloning in Pseudomonas," *Gene*, 16(1–3):237–247, 1981.
Ballas et al., *Nucl. Acids Res.*, 17:7991–7903, 1989.
Baum et al., *Appl. Environ. Microbiol.*, 56:3420–3428, 1990.
Baumlein, Boerjan, Nagy, Panitz, Inze, Wobus, "Upstream sequences regulating legumin gene expression in heterologous transgenic plants," *Mol. Gen. Genet.*, 225(1): 121–128, 1991.
Beaudouin, Haurat, Lafitte and Renaud, *J. Neurochem.*, 61:928–935, 1993.
Benbrook et al., In: *Proceedings Bio Expo 1986*, Butterworth, Stoneham, Mass., pp. 27–54, 1986.
Berna and Bernier, "Regulated expression of a wheat germin gene in tobacco: oxalate oxidase activity and apoplastic localization of the heterologous protein," *Plant Mol. Biol.*, 33(3):417429, 1997.

Bevan et al., *Nature*, 304:184, 1983.

Bligny, Gardestrom, Roby and Douce, *J. Biol. Chem.*, 265:1319–1326, 1990.

Boffa, Carpaneto, Allfrey, *Proc. Natl. Acad. Sci. USA*, 92:1901–1905, 1995.

Boronat, Martinez, Reina, Puigdomenech, Palau, "Isolation and sequencing of a 28 kd gluteline-2 gene from maize: Common elements in the 5' flanking regions among zein and glutelin genes," *Plant Sci.*, 47:95–102, 1986.

Bytebier et al., "t-DNA organization in tumor cultures and transgenic plants of the monocotyledon apsparagus-officinalis," *Proc. Natl. Acad. Sci. USA*, 84(15): 5345–5349, 1987.

Callis, Fromm, Walbot, "Introns increase gene expression in cultured maize cells," *Genes Devel.*, 1:1183–1200, 1987.

Campbell, In: *Monoclonal Antibody Technology, Laboratory Techniques in Biochemistry and Molecular Biology*, Burden and Von Knippenberg (Eds.), Vol. 13, pp. 75–83, Elsevier, Amsterdam, 1984.

Capecchi, "High efficiency transformation by direct microinjection of DNA into cultured mammalian cells," *Cell*, 22(2):479–488, 1980.

Cheng et al., *Proc. Natl. Acad. Sci. USA*, 95(6):2767–2772, 1998.

Christensen, Sharrock, Quail, "Maize polyubiquitin genes: Structure, thermal perturbation of expression and transcript splicing, and promoter activity following transfer to protoplasts by electroporation," *Plant Mol. Biol.*, 18:675–689, 1992.

Clapp, "Somatic gene therapy into hematopoietic cells. Current status and future implications," *Clin. Perinatol.*, 20(1):155–168, 1993.

Conway and Wickens, In: RNA Processing, Cold Spring Harbor Laboratory, Cold Spring Harbor, N.Y., p. 40, 1988.

Cook and Wagner, *Proc. Natl. Acad. Sci. USA*, 81:3631–3634, 1984.

Corey, *Trends Biotechnol.*, 15(6):224–229, 1997.

Corpet, *Nucleic Acids Res.*, 16:10881–10890, 1988.

Crane, Friis and Pedersen, *Nature*, 374:27–33, 1995.

Cristou et al., *Plant Physiol*, 87:671–674, 1988.

Curiel, Agarwal, Wagner, Cotten, "Adenovirus enhancement of transferrin-polylysine-mediated gene delivery," *Proc. Natl. Acad. Sci. USA*, 88(19):8850–8854, 1991.

Danos and Heard, "Recombinant retroviruses as tools for gene transfer to somatic cells," *Bone Marrow Transplant*, 9(Suppl. 1):131–138, 1992.

Datko and Mudd, *Plant Physiol.*, 88:1338–1348, 1988b.

Datko and Mudd, *Plant Physiol.*, 88:854–861, 1988a.

Dean et al., *Nucl. Acids Res.*, 14(5):2229–2240, 1986.

Dennis, Gerlach, Pryor, Bennetzen, Inglis, Llewellyn, Sachs, Ferl, Peackocock, "Molecular analysis of the alcohol dehydrogenase (Adh1) gene of maize," *Nucl Acids Res.*, 12:3983–4000, 1984.

Eglitis and Anderson, "Retroviral vectors for introduction of genes into mammalian cells," *Biotechniques*, 6(7):608–614, 1988.

Eichholtz et al., "Expression of mouse dihydrofolate reductase gene confers methotrexate resistance in transgenic petunia plants," *Somat. Cell Mol. Genet.*, 13(1):67–76, 1987.

Faktor, Kooter, Dixon, Lamb, "Functional dissection of a bean chalcone synthase gene promoter in transgenic tobacco plants reveals sequence motifs essential for floral expression," *Plant Mol. Biol.*, 32(5):849–859, 1996.

Ficker, Kirch, Eijlander, Jacobsen, Thompson, "Multiple elements of the S2-RNase promoter from potato (*Solanum tuberosum* L.) are required for cell type-specific expression in transgenic potato and tobacco," *Mol. Gen. Genet.*, 257(2):132–142, 1998.

Fraley et al., *Biotechnology*, 3:629–635, 1985.

Fraley, Rogers, Horsch, Sanders, Flick, Adams, Bittner, Brand, Fink, Fry, Galluppi, Goldberg, Hoffmann, Woo, "Expression of bacterial genes in plant cells," *Proc. Natl. Acad. Sci. USA*, 80(15):4803–4087, 1983.

French, Janda, Ahlquist, "Bacterial gene inserted in an engineered RNA virus: efficient expression in monocotyledonous plant cells," *Science*, 231:1294–1297, 1986.

Fromm, Taylor, Walbot, "Expression of genes transferred into monocot and dicot plant cells by electroporation," *Proc. Natl. Acad Sci. USA*, 82(17):5824–5828, 1985.

Fujimura et al., *Plant Tissue Cult. Lett.*, 2:74, 1985.

Fujioka, *Int J. Biochem.*, 24:1917–1924, 1992.

Gallie and Young, "The regulation of expression in transformed maize aleurone and endosperm protoplasts," *Plant Physiol.*, 106:929–939, 1994.

Gallie, Feder, Schimke, Walbot, "Post-transcriptional regulation in higher eukaryotes: the role of the reporter gene in controlling expression," *Mol. Gen. Genet.*, 228:258–264, 1991.

Gallie, Lucas, Walbot, "Visualizing mRNA expression in plant protoplasts: factors influencing efficient mRNA uptake and translation," *Plant Cell*, 1:301–311, 1989.

Gallie, Sleat, Turner, Wilson, "Mutational analysis of the tobacco mosaic virus 5'-leader for altered ability to enhance translation," *Nucl. Acids Res.*, 16:883–893, 1988.

Gallie, Sleat, Watts, Turner, Wilson, "A comparison of eukaryotic viral 5'-leader sequences as enhancers of mRNA expression in vivo," *Nucl. Acids Res.*, 15:8693–8711, 1987b.

Gallie, Sleat, Watts, Turner, Wilson, "The 5'-leader sequence of tobacco mosaic virus RNA enhances the expression of foreign gene transcripts in vitro and in vivo," *Nucl. Acids Res.*, 15:3257–3273, 1987a.

GAP, BESTFIT, BLAST, FASTA, and TFASTA in the Wisconsin Genetics Software Package, Genetics Computer Group (GCG), 575 Science Drive, Madison, Wis., USA.

Gary, Lin, Yang, Herschman and Clarke, *J. Biol. Chem.*, 271:12585–12594, 1996.

Gefter, Margulies, Scharff, "A simple method for polyethylene glycol-promoted hybridization of mouse myeloma cells," *Somat. Cell Genet.*, 3(2):231–236, 1977.

Gehrke, Auron, Quigley, Rich, Sonenberg, "5'-Conformation of capped alfalfa mosaic virus ribonucleic acid 4 may reflect its independence of the cap structure or of cap-binding protein for efficient translation," *Biochemistry*, 22:5157–5164, 1983.

Gil and Proudfoot, "A sequence downstream of AAUAAA is required for rabbit beta-globin mRNA 3'-end formation," *Nature*, 312(5993):473–474, 1984.

Goding, "Monoclonal Antibodies: Principles and Practice," pp. 60–74, 2nd Edition, Academic Press, Orlando, Fla., 1986.

Goelet, Lomonossoff, Butler, Akam, Gait, Karn, "Nucleotide sequence of tobacco mosaic virus RNA," *Proc. Natl. Acad. Sci. USA*, 79:5818–5822, 1982.

Good and Nielsen, *Antisense Nucleic Acid Drug Dev.*, 7(4):431437, 1997.

Gothel et al., *Eur. J. Biochem.*, 244(1):59–65, 1997.

Graham and van der Eb, "Transformation of rat cells by DNA of human adenovirus 5," *Virology*, 54(2):536–539, 1973.

Graham, Craig, Waterhouse, "Expression patterns of vascular-specific promoters ROlC and Sh in transgenic potatoes and their use in engineering PLRV-resistant plants," *Plant Mol. Biol.,* 33(4):729–735, 1997.

Grosset, Alary, Gautier, Menossi, Martinez-Izquierdo, Joudrier, "Characterization of a barley gene coding for an alpha-amylase inhibitor subunit (Cmd protein) and analysis of its promoter in transgenic tobacco plants and in maize kernels by microprojectile bombardment," *Plant Mol. Biol.,* 34(2):331–338, 1997.

Guerineau et al., *Mol. Gen Genet.,* 262:141–144, 1991.

Hanson and Rhodes, *Plant Physiol.,* 71:692–700, 1983.

Hanvey et al., *Science,* 258:1481–1485, 1992.

Harlow and Lane, In: *Antibodies: A Laboratory Manual,* Cold Spring Harbor Laboratory, Cold Spring Harbor, N.Y., 1988.

Herrera-Estrella et al., *Nature,* 303:209, 1983.

Hess, *Intern Rev. Cytol.,* 107:367, 1987.

Higgins et al., *Gene,* 73:237–244, 1988.

Higgins et al., *CABIOS,* 5:151–153, 1989.

Hilber et al., "Biolistic transformation of *Botryotinia fuckeliana,*" *Curr. Genet.,* 25(2):124–127, 1994.

Hockema, In: *The Binary Plant Vector System,* Offsetdurkkerij, Kanters B. V., Alblasserdam, Chapter 5, 1985.

Holsters et al., *Mol. Gen. Genet.,* 163:181–187, 1978.

Hondred, Wadle, Titus and Becker, *Plant Mol. Biol.,* 9:259–275, 1987.

Horsch et al., *Science,* 227:1229–1231, 1985.

Huang et al., *Computer Applications in the Biosciences,* 8:155–165, 1992.

Huang, An, McDowell, McKinney, Meagher, "The *Arabidopsis* ACT11 action gene is strongly expressed in tissues of the emerging inflorescence, pollen and developing ovules," *Plant Mol. Biol.,* 33(1):125–139, 1997.

Huang, Hirji, Adam, Rozwadowski, Hammerlindl, Keller and Selvaraj, *Plant Physiol,* in press, 2000.

Hudspeth and Grula, "Structure and expression of the maize gene encoding the phosphoenolpyruvate carboxylase isozyme involved in C4 photosynthesis," *Plant Mol. Biol.,* 12:579–589, 1989.

Ingelbrecht, Herman, Dekeyser, Van Montagu, Depicker, "Different 3' end regions strongly influence the level of gene expression in plant cells," *Plant Cell,* 1:671–680, 1989.

Jameson and Wolf, "The Antigenic Index: A Novel Algorithm for Predicting Antigenic Determinants", *Compu. Appl. Biosci.,* 4(1):181–6, 1988.

Jobling and Gehrke, "Enhanced translation of chimaeric messenger RNAs containing a plant viral untranslated leader sequence," *Nature,* 325:622–625, 1987.

Jones, Dean, Gidoni, Gilbert, Bond-Nutter, Lee, Bedbrook, Dunsmuir, "Expression of bacterial chitinase protein in tobacco leaves using two photosynthetic gene promoters," *Mol. Gen. Genet.,* 212:536–542, 1988.

Jorgensen et al., *Mol. Gen. Genet.,* 207:471, 1987.

Joshi et al., *Nucleic Acids Res.,* 15:9627–9639, 1987.

Kagan and Clarke, *Arch. Biochem. Biophys.,* 310:417–427, 1994.

Kaiser and Kezdy, *Science,* 223:249–255, 1984.

Kanipes and Henry, *Biochim. Biophys. Acta,* 1348:134–141, 1997.

Kanipes, Hill and Henry, *Genetics,* 150:553–562, 1998.

Kanipes, Ph.D Thesis. Carnegie Mellon University, 1997.

Klee et al., *Biotechnology,* 3:637–642, 1985.

Klein et al., "Factors influencing gene delivery into *Zea mays* cells by high velocity microprojectiles," *Bio/Tech.,* 6:559–563, 1988a.

Klein et al., *Nature,* 327:70, 1987.

Klein et al., *Plant Physiol.,* 91:440–444, 1988b.

Klein et al., *Proc. Natl. Acad. Sci. USA,* 85:4305–4309, 1988c.

Klein et al, *Proc. Natl. Acad. Sci. USA,* 85:8502–8505, 1988d.

Kohler and Milstein, "Continuous cultures of fused cells secreting antibody of predefined specificity," *Nature,* 256 (5517):495–497, 1975.

Kohler and Milstein, "Derivation of specific antibody-producing tissue culture and tumor lines by cell fusion," *Eur. J. Immunol.,* 6(7):511–519, 1976.

Kozak, *Nature,* 308:241–246, 1984.

Koziel et al., *Plant Mot Biol.,* 32:393–405, 1996.

Koziel, Beland, Bowman, Carozzi, Crenshaw, Crossland, Dawson, Desai, Hill, Kadwell, Launis, Lewis, Maddox, McPherson, Meghji, Merlin, Rhodes, Warren, Wright, Evola, "Field performance of elite transgenic maize plants expressing an insecticidal protein derived from *Bacillus thuringiensis,*" *Bio/technology,* 11:194–200, 1993.

Kuby, *Immunology* 2nd Edition, W. H. Freeman & Company, NY, 1994.

Kunkel, *Proc. Natl. Acad. Sci. USA,* 82:488–492, 1985.

Kunkel, Roberts, Zabour, *Methods Enzymol.,* 154:367–382, 1987.

Kyozuka et al., "Anaerobic induction and tissue-specific expression of maize Adh1 promoter in transgenic rice plants and their progeny," *Mol. Gen. Genet.,* 228(1–2): 4048, 1991.

Lorz et al., *Mol. Gen. Genet.,* 199:178, 1985.

Luehrsen and Walbot, "Intron enhancement of gene expression and the splicing efficiency of introns in maize cells," *Mol Gen. Genet.,* 225:81–93, 1991.

Luehrsen, De Wit and Walbot, *Methods Enzymol.,* 216:397–414, 1992.

Luehrsen, In: *The Maize Handbook,* Springer-Verlag New York, Inc., New York, N.Y., 1994.

Luo et al., *Plant Mol. Biol Report.,* 6:165, 1988.

Lutcke, Chow, Mickel, Moss, Kern, Scheele, "Selection of AUG initiation codons differs in plants and animals," *EMBO J.,* 6:43–48, 1987.

Maas, Laufs, Grant, Korfhage, Werr, "The combination of a novel stimulatory element in the first exon of the maize shrunken-1 gene with the following intron enhances reporter gene expression 1000-fold," *Plant Mol. Biol.,* 16:199–207, 1991.

Maddock et al., *Third International Congress of Plant Molecular Biology,* Abstract 372, 1991.

Maloy et al, In: *Microbial Genetics,* 2nd Ed., Jones and Bartlett Publishers, Boston, Mass., 1994.

Marcotte et al., *Nature,* 335:454, 1988.

Mascerenhas, Mettler, Pierce, Lowe, "Intron mediated enhancement of heterologous gene expression in maize," *Plant Mol. Biol.,* 15:913–920, 1990.

Maundrell, *Gene,* 123:127–130, 1993.

McCabe et al., *Biotechnology,* 6:923–926, 1988.

McCormick et al., *Plant Cell Reports,* 5:81–84, 1986.

McDevitt, Imperiale, Ali, Nevins, "Requirement of a downstream sequence for generation of a poly(A) addition site," *Cell,* 37(3):993–999, 1984.

McElroy, Zhang, Cao, Wu, "Isolation of an efficient promoter for use in rice transformation," *Plant Cell,* 2(2): 163–171, 1990.

McNeil, Rhodes, Nuccio and Hanson, *Plant Physiol.,* submitted, 2000.

Mogen et al., *Plant Cell,* 2:1261–1272, 1990.

Mollegaard, Buchardt, Egholm, Nielsen, "Peptide nucleic acid. DNA strand displacement loops as artificial transcription promoters," *Proc. Natl. Acad. Sci. USA,* 91(9): 3892–3895, 1994.

Mudd and Datko, *Plant Physiol.,* 90:296–305, 1989.

Mudd and Datko, *Plant Physiol.,* 90:306–310, 1989b.

Mudd et al., *Plant Physiol.,* 93:623–630, 1990.

Mukherjee, Freysz and Kanfer, *Neurochem Res.,* 20:1233–1237, 1995.

Munroe et al., *Gene,* 91:151–158, 1990.

Nairn and Ferl, *J. Mol. Evol.,* 27:133–141, 1988.

Nawrath, Poirier, Somerville, "Targeting of the polyhydroxybutyrate biosynthetic pathway to the plastids of *Arabidopsis thaliana* results in high levels of polymer accumulation," *Proc. Natl. Acad. Sci. USA,* 91:12760–12764, 1994.

Needleman et al., *J. Mol. Biol.,* 48:443, 1970.

Neuhaus et al., *Theor. Appl. Genet.,* 75:30, 1987.

Nielsen et al., "Peptide nucleic acids (PNAs): potential antisense and anti-gene agents," *Anticancer Drug Des.,* 8(1):53–63, 1993.

Nielsen, Egholm, Berg, Buchardt "Sequence-selective recognition of DNA by strand displacement with a thymine-substituted polyamide," *Science,* 254(5037):1497–1500, 1991.

Nuccio, Rhodes, McNeil and Hanson, *Curr. Opin. Plant Biol.,* 2:128–134, 1999.

Nuccio, Russell. Nolte, Rathinasabapathi, Gage and Hanson, *Plant J.,* 16:487–496, 1998.

Oard, Paige, Dvorak, "Chimeric gene expression using maize intron in cultured cells of breadwheat," *Plant Cell. Rep.,* 8:156–160, 1989.

Olson, Porter, Rubinstein, Silver, "Mercuric reductase enzyme from a mercury-volatilizing strain of Thiobacillus ferrooxidans," *J. Bacteriol.,* 151(3):1230–1236, 1982.

Omirulleh, Abraham, Golovkin, Stefanov, Karabaev, Mustardy, Morocz, Dudits, "Activity of a chimeric promoter with the doubled CaMV 35S enhancer element in protoplast-derived cells and transgenic plants in maize," *Plant Molecular Biology,* 21(3):415–428, 1993.

Orum, Nielsen, Egholm, Berg, Buchardt, Stanley, "Single base pair mutation analysis by PNA directed PCR™ clamping," *Nucl Acids Res.,* 21(23):5332–5336, 1993.

Orum, Nielsen, Jorgensen, Larsson, Stanley, Koch, "Sequence-specific purification of nucleic acids by PNA-controlled hybrid selection," *BioTechniques,* 19(3): 472–480, 1995.

Pearson et al., *Proc. Natl. Acad. Sci. USA,* 85:2444, 1988.

Pena et al., *Nature,* 325:274, 1987.

Perlak, Deaton, Armstrong, Fuchs, Sims, Greenplate, Fischhoff, "Insect resistant cotton plants," *Bio/technology,* 8:939–943, 1990.

Perlak, Fuchs, Dean, McPherson, Fischhoff, "Modification of the coding sequence enhances plant expression of insect control protein genes," *Proc. Natl. Acad. Sci. USA,* 88:3324–3328, 1991.

Perlak, Stone, Muskopf, Peterson, Parker, McPherson, Wyman, Love, Reed, Biever, Fischhoff, "Genetically improved potatoes: protection from damage by Colorado potato beetles,"*Plant Mol. Biol.,* 22:313–321, 1993.

Perry-O'Keefe, Yao, Coull, Fuchs, Egholm, "Peptide nucleic acid pre-gel hybridization: an alternative to southern hybridization," *Proc. Natl. Acad. Sci. USA,* 93(25): 14670–14675, 1996.

Person et al., *Methods of Molecular Biology,* 24:307–331, 1994.

Poogin and Skryabin, "The 5' untranslated leader sequence of potato virus X RNA enhances the expression of the heterologous gene in vivo," *Mol. Gen Genet.,* 234:329–331, 1992.

Potrykus, Paszkowski, Saul, Petruska, Shillito, "Molecular and general genetics of a hybrid foreign gene introduced into tobacco by direct gene transfer," *Mol. Gen. Genet.,* 199(2):169–177, 1985.

Prokop and Bajpai, "Recombinant DNA Technology I," *Ann. N. Y. Acad. Sci., Vol.* 646, 1991.

Proudfoot, *Cell,* 64:671–674, 1991.

Rathinasabapathi, Burnet, Russell, Gage, Liao, Nye, Scott, Golbeck and Hanson, *Proc. Natl. Acad. Sci. USA,* 94:3454–3458, 1997.

Rhodes and Hanson, *Annu. Rev. Plant Physiol. Plant Mol. Biol.,* 44:357–384, 1993.

Rogers et al., In: *Methods For Plant Molecular Biology,* Weissbach and Weissbach, Eds., Academic Press Inc., San Diego, Calif., 1988.

Russell and Fromm, "Tissue-specific expression in transgenic maize for four endosperm promoters from maize and rice," *Transgenic Res.,* 6(2):157–168, 1997.

Sadofsky and Alwine, "Sequences on the 3' side of hexanucleotide AAUAAA affect efficiency of cleavage at the polyadenylation site," *Molec. Cell. Biol.,* 4(8): 1460–1468, 1984.

Sambrook et al., In: *Molecular Cloning: A Laboratory Manual,* 2nd Ed.; Cold Spring Harbor Laboratory Press, Plainview, N.Y., 1989.

Sanfacon et al., *Genes Dev.,* 5:141–149, 1991.

Segal, "Biochemical Calculations" 2nd Edition, John Wiley & Sons, New York, 1976.

Shaw and Kamen, "A conserved AU sequence from the 3' untranslated region of GM-CSF mRNA mediates selective mRNA degradation," *Cell,* 46(5):659–667, 1986.

Shaw and Kamen, *In: RNA Processing, Cold Spring Harbor Laboratory, Cold Spring Harbor, N.Y., p.* 220, 1987.

Sleat, Gallie, Jefferson Bevan, Turner, Wilson, "Characterization of the 5'-leader sequence of tobacco mosaic virus RNA as a general enhancer of translation in vitro," *Gene,* 217:217–225, 1987.

Sleat, Hull, Turner, Wilson, "Studies on the mechanism of translational enhancement by the 5'-leader sequence of tobacco mosaic virus RNA," *Eur. J. Biochem.,* 175:75–86, 1988.

Smith and Hood, "*Agrobacterium tumefaciens* transformation of monocotyledons," *Crop Science,* 35:301–309, 1995.

Smith et al., *Adv. Appl. Math,* 2:482, 1981.

Smith, Summers and Weretilnyk, *Physiol. Plant.,* in press, 1999.

Speich et al., *Microbiol.,* 140(Pt6):1273–1284, 1994.

Spielmann et al., *Mol. Gen. Genet,* 205:34, 1986.

Summers and Weretilnyk, Plant Physiol., 103:1269–1276, 1993.

Tanaka, Mita, Ohta, Kyozuka, Shimamoto, Nakamura, "Enhancement of foreign gene expression by a dicot intron in rice but not in tobacco is correlated with an increased level of mRNA and an efficient splicing of the intron," *Nucl. Acids Res.,* 18:6767–6770, 1990.

Thisted, Just, Petersen, Hyldig-Nielsen, Godtfredsen, *Cell Vision,* 3:358–363, 1996.

Tomes et al, "Transgenic tobacco plants and their progeny derived by microprojectile bombardment of tobacco leaves," *Plant Mol. Biol.,* 14:261–268, 1990.

Toriyama et al., *Theor. Appl. Genet.,* 73:16, 1986.

Treacy, Hattori, Prud'homme, Barbour, Boutilier, Baszczynski, Huang, Johnson, Miki, "Bnml, a *Brassica* pollen-specific gene," *Plant Mol. Biol.,* 34(4):603–611, 1997.

Uchimiya et al., *Mol. Gen. Genet.,* 204:204, 1986.

Vain et al., "Osmotic pretreatment enhances particle bombardment-mediated transient and stable transformation of maize," *Plant Cell Rep.*, 12:84–88, 1993.

Van Camp, Herouart, Willekens, Takahashi, Saito, Van Montagu, Inze, "Tissue-specific activity of two manganese superoxide dismutase promoters in transgenic tobacco," *Plant Physiol.*, 112(2):525–535, 1996.

Vance, Walkey and Cui, *Biochim. Biophys. Acta*, 1348:142–150, 1997.

Vander, Van Montagu, Inze, Boerjan, "Tissue-specific expression conferred by the S-adenosyl-L-methionine synthetase promoter of *Arabidopsis thaliana* in transgenic poplar," *Plant Cell Physiol.*, 37(8):1108–1115, 1996.

Vasil et al., "Herbicide-resistant fertile transgenic wheat plants obtained by microprojectile bombardment of regenerable embryogenic callus," *Biotechnology*, 10:667–674, 1992.

Vasil, *Biotechnology*, 6:397, 1988.

Vasil, Clancy, Ferl, Vasil, Hannah, "Increased gene expression by the first intron of maize shrunken-1 locus in grass species," *Plant Physiol.*, 91:1575–1579, 1989.

Velten and Schell, "Selection-expression plasmid vectors for use in genetic transformation of higher plants," *Nucl. Acids Res.*, 13(19):6981–6998, 1985.

Velten et al., *EMBO J.*, 3:2723–2730, 1984.

Veselkov, Demidov, Nielsen, Frank-Kamenetskii, "A new class of genome rare cutters," *Nucl. Acids Res.*, 24(13):2483–2487, 1996.

Vickers, Griffith, Ramasamy, Risen, Freier, "Inhibition of NF-kappa B specific transcriptional activation by PNA strand invasion," *Nucl. Acids Res.*, 23(15):3003–3008, 1995.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.

Walker and Gaastra, Eds., *Techniques in Molecular Biology*, MacMillan Publishing Company, New York, 1983.

Wang et al., "Transient expression of foreign genes in rice, wheat and soybean cells following particle bombardment," *Plant Mol. Biol.*, 11:433–439, 1988.

Wang, *J. Am. Chem. Soc.*, 118:7667–7670, 1996.

Weissbach and Weissbach, Eds., *Methods for Plant Molecular Biology*, Academic Press, Inc., San Diego, Calif., 1988.

Weretilnyk, Smith, Wilch and Summers, *Plant Physiol.*, 109:1085–1091, 1995.

Wickens and Stephenson, "Role of the conserved AAUAAA sequence: four AAUAAA point mutants prevent messenger RNA 3' end formation," *Science*, 226(4678):1045–1051, 1984.

Wickens et al., In: *RNA Processing*, Cold Spring Harbor Laboratory, Cold Spring Harbor, N.Y., p. 9, 1987.

Wilson, Flint, Deaton, Fischhoff, Perlak, Armstrong, Fuchs, Berberich, Parks, Stapp, "Resistance of cotton lines containing a *Bacillus thuringiensis* toxin to pink bollworm (Lepidopteran: Gelechiidae) and other insects," *J. Econ. Entomol.*, 4:1516–1521, 1992.

Winter, Robinson and Heldt, *Planta*, 193:530–535, 1994.

Wolf et al, "An Integrated Family of Amino Acid Sequence Analysis Programs," *Compu Appl. Biosci.*, 4(1):187–91, 1988.

Wong and Neumann, "Electric field mediated gene transfer," *Biochim. Biophys. Res. Commun.*, 107(2):584–587, 1982.

Yamada et al., *Plant Cell Rep.*, 4:85, 1986.

Yang et al., *Proc. Natl. Acad. Sci. USA*, 87:4144–4148, 1990.

Yin, Chen, Beachy, "Promoter elements required for phloem-specific gene expression from the RTBV promoter in rice," *Plant J.*, 12(5):1179–1188, 1997a.

Yin, Zhu, Dai, Lamb, Beachy, "RF2a, a bZIP transcriptional activator of the phloem-specific rice tungro bacilliform virus promoter, functions in vascular development," *EMBO J.*, 16(17):5247–5259, 1997b.

Zhou et al., "Introduction of exogenous DNA into cotton embryos," *Methods Enzymol*, 101:433–481, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated polynucleotide that encodes a polypeptide having S-adenosyl-L-methionine:phosphoethanolamine N-methyltransferase activity and having at least about 95% sequence identity with the amino acid sequence of SEQ ID NO:2 or SEQ ID NO:4.

2. An isolated polynucleotide comprising a sequence region that encodes a polypeptide comprising the sequence of SEQ ID NO:2.

3. The isolated polynucleotide of claim 1 comprising a sequence region that encodes a polypeptide having S-adenosyl-L-methionine:phosphoethanolamine N-methyltransferase activity and and at least about 96% sequence identity with the amino acid sequence of SEQ ID NO:2 or SEQ ID NO:4.

4. The isolated polynucleotide of claim 3, comprising a sequence region that encodes a polypeptide having S-adenosyl-L-methionine:phosphoethanolamine N-methyltransferase activity and having at least about 98% sequence identity with the amino acid sequence of SEQ ID NO:2 or SEQ ID NO:4.

5. A virus comprising the polynucleotide of claim 1.

6. A host cell comprising the polynucleotide of claim 1 or the virus of claim 5.

7. The host cell of claim 6, wherein said host cell is a bacterial cell.

8. The host cell of claim 7, wherein said host cell is an *Escherichia*, *Salmonella* or *Agrobacterium* cell.

9. An isolated polynucleotide comprising a sequence region that encodes a polypeptide comprising the sequence of SEQ ID NO:4.

10. The isolated polynucleotide of claim 4, comprising a sequence region that encodes a polypeptide having S-adenosyl-L-methionine:phosphoethanolamine N-methyltransferase activity and having at least about 99% sequence identity with the amino acid sequence of SEQ ID NO:2 or SEQ ID NO:4.

11. The isolated polynucleotide of claim 10, comprising a sequence region that encodes a polypeptide that comprises the amino acid sequence of SEQ ID NO:2 or SEQ ID NO:4.

12. The isolated polynucleotide of claim 1 comprised within a vector.

13. The host cell of claim 6, wherein said host cell is a eukaryotic cell.

14. A composition comprising the polynucleotide of claim 1 or claim 2.

15. A kit comprising, in suitable container means, (a) the polynucleotide of claim 1 or the polynucleotide of claim 2; and (b) instructions for using said kit.

16. A kit comprising, in suitable container means, (a) the virus of claim 5 or the host cell of claim 15; and (b) instructions for using said kit.

\* \* \* \* \*